(12) United States Patent
Yu et al.

(10) Patent No.: US 9,504,753 B2
(45) Date of Patent: Nov. 29, 2016

(54) NANOMETER-SIZED PRODRUGS OF NSAIDS

(71) Applicant: Cedars-Sinai Medical Center, Los Angeles, CA (US)

(72) Inventors: John S. Yu, Los Angeles, CA (US); Bong Seop Lee, Torrance, CA (US)

(73) Assignee: Cedars-Sinai Medical Center, Los Angeles, CA (US)

( * ) Notice: Subject to any disclaimer, the term of this patent is extended or adjusted under 35 U.S.C. 154(b) by 57 days.

(21) Appl. No.: 14/069,001

(22) Filed: Oct. 31, 2013

(65) Prior Publication Data

US 2014/0127272 A1    May 8, 2014

Related U.S. Application Data

(60) Division of application No. 12/995,125, filed as application No. PCT/US2009/039956 on Apr. 8, 2009, now Pat. No. 8,603,531, and a continuation-in-part of application No. PCT/US2008/088541, filed on Dec. 30, 2008.

(60) Provisional application No. 61/058,190, filed on Jun. 2, 2008, provisional application No. 61/058,189, filed on Jun. 2, 2008.

(51) Int. Cl.
*A61K 47/48* (2006.01)
*A61K 9/14* (2006.01)
*C07D 339/04* (2006.01)

(52) U.S. Cl.
CPC ........... *A61K 47/48061* (2013.01); *A61K 9/14* (2013.01); *C07D 339/04* (2013.01)

(58) Field of Classification Search
None
See application file for complete search history.

(56) References Cited

U.S. PATENT DOCUMENTS

| | | | |
|---|---|---|---|
| 3,963,771 A | 6/1976 | Robson et al. | |
| 5,122,526 A | 6/1992 | Wall et al. | |
| 5,393,527 A | 2/1995 | Malick et al. | |
| 5,543,158 A | 8/1996 | Gref et al. | |
| 5,681,964 A * | 10/1997 | Ashton et al. | 548/491 |
| 5,883,128 A | 3/1999 | Yu et al. | |
| 5,962,520 A | 10/1999 | Smith et al. | |
| 6,013,663 A | 1/2000 | Fujita et al. | |
| 6,090,842 A | 7/2000 | Packer et al. | |
| 6,117,899 A | 9/2000 | Wessel et al. | |
| 6,123,956 A | 9/2000 | Baker et al. | |
| 6,127,394 A | 10/2000 | Pershadsingh et al. | |
| 6,150,358 A | 11/2000 | Goldstein et al. | |
| 6,204,288 B1 | 3/2001 | Pershadsingh et al. | |
| 6,235,772 B1 | 5/2001 | Packer et al. | |
| 6,265,180 B1 | 7/2001 | Zuelli et al. | |
| 6,288,106 B1 | 9/2001 | Pearson et al. | |
| 6,353,011 B1 | 3/2002 | Pershadsingh et al. | |
| 6,369,098 B1 | 4/2002 | Pershadsingh et al. | |
| 6,380,405 B1 | 4/2002 | Ekwuribe et al. | |
| 6,387,945 B2 | 5/2002 | Packer et al. | |
| 6,572,888 B2 | 6/2003 | Byrd | |
| 6,605,637 B1 | 8/2003 | Harnett et al. | |
| 6,629,995 B1 | 10/2003 | Wrenn et al. | |
| 6,664,287 B2 | 12/2003 | Avery et al. | |
| 6,667,048 B1 | 12/2003 | Quay et al. | |
| 6,821,529 B2 | 11/2004 | Nelson | |
| 6,878,374 B2 | 4/2005 | Yu et al. | |
| 6,887,891 B2 | 5/2005 | Harnett et al. | |
| 6,900,337 B2 | 5/2005 | Manzer et al. | |
| 6,900,338 B1 | 5/2005 | Haj-Yehia | |
| 6,936,715 B2 | 8/2005 | Harnett et al. | |
| 6,998,115 B2 | 2/2006 | Langer et al. | |
| 7,048,925 B2 | 5/2006 | Van et al. | |
| 7,056,901 B2 | 6/2006 | Frechet et al. | |
| 7,157,444 B2 | 1/2007 | Nelson | |
| 7,220,414 B2 | 5/2007 | Brocchini et al. | |
| 7,713,544 B2 | 5/2010 | Chaikof et al. | |
| 8,318,795 B2 | 11/2012 | Yu et al. | |
| 8,603,531 B2 | 12/2013 | Yu et al. | |
| 8,697,743 B2 | 4/2014 | Yu et al. | |
| 9,028,874 B2 | 5/2015 | Yu et al. | |
| 2002/0193419 A1 | 12/2002 | Dai et al. | |
| 2004/0053989 A1 | 3/2004 | Prendergast et al. | |
| 2005/0043493 A1 | 2/2005 | Smith et al. | |
| 2005/0065194 A1 | 3/2005 | Shankar et al. | |
| 2006/0013882 A1 | 1/2006 | Kohn et al. | |
| 2007/0104714 A1 | 5/2007 | Agus et al. | |
| 2007/0148196 A1 | 6/2007 | Haas et al. | |
| 2007/0208134 A1 | 9/2007 | Hunter et al. | |

(Continued)

FOREIGN PATENT DOCUMENTS

| | | |
|---|---|---|
| CN | 103841961 A | 6/2014 |
| EP | 2125775 | 12/2009 |

(Continued)

OTHER PUBLICATIONS

International Preliminary Report on Patentability dated Sep. 1, 2009 for PCT/US2008/055465.
International PCT Search Report and Written Opinion dated Jul. 1, 2008 for PCF/US2008/0554.
European publication No. 2125775 published Dec. 2, 2009, abstract corresponds to WO/2008/106640.
International PCT Search Report and Written Opinion dated Feb. 27, 2009 for PCT/US2008/088541.
International Preliminary Report on Patentability dated Jul. 6, 2010 for PCT/US2008/088541.
International Preliminary Report on Patentability date Dec. 6, 2010 for PCT/US2009/039956.
International PCT Search Reportand Written Opinion dated Jan. 21, 2010 for PCT/US2009/065776.
International Preliminary Report on Patentability dated May 24, 2011 for PCT/US52009/065776.

(Continued)

*Primary Examiner* — Jessica Worsham
(74) *Attorney, Agent, or Firm* — Nixon Peabody LLP; Linda B. Huber

(57) ABSTRACT

The present invention describes nanoprodrugs of non-steroidal anti-inflammatory drug (NSAIDs) and nanoprodrugs of α-lipoic acid-containing and NSAIDs. These nanoprodrugs have antioxidant properties and stimuli-responsiveness, which can be used to treat various disease conditions.

17 Claims, 19 Drawing Sheets

(56) References Cited

U.S. PATENT DOCUMENTS

| | | |
|---|---|---|
| 2007/0281047 A1 | 12/2007 | Henry et al. |
| 2010/0098653 A1 | 4/2010 | Yu |
| 2010/0291222 A1 | 11/2010 | Yu |
| 2010/0310498 A1 | 12/2010 | Kanamathareddy |
| 2011/0086073 A1 | 4/2011 | Yu et al. |
| 2011/0123456 A1 | 5/2011 | Pandit et al. |
| 2011/0176994 A1 | 7/2011 | Pratt et al. |
| 2011/0300187 A1 | 12/2011 | Yu et al. |
| 2012/0183475 A1 | 7/2012 | Michel et al. |
| 2012/0252740 A1 | 10/2012 | Kozikowski et al. |
| 2012/0294960 A1 | 11/2012 | Frondoza et al. |
| 2014/0105822 A1 | 4/2014 | Yu et al. |
| 2014/0140931 A1 | 5/2014 | Yu et al. |

FOREIGN PATENT DOCUMENTS

| | | |
|---|---|---|
| EP | 2736493 A0 | 6/2014 |
| EP | 2370435 B1 | 1/2015 |
| JP | 2010-520333 | 6/2010 |
| JP | 2012-509901 A | 4/2012 |
| JP | 5564512 | 6/2014 |
| JP | 2014-523924 A | 9/2014 |
| WO | WO 9743274 A1 | 11/1997 |
| WO | WO 9801440 A2 | 1/1998 |
| WO | WO 99/38881 | 8/1999 |
| WO | WO 01/29221 | 4/2001 |
| WO | WO01/53312 | 7/2001 |
| WO | WO 02/046465 A3 | 6/2002 |
| WO | WO 2004/050795 | 6/2004 |
| WO | 2006102768 A1 | 10/2006 |
| WO | 2007027559 A2 | 3/2007 |
| WO | WO 2008/012365 A2 | 1/2008 |
| WO | WO 2008/106640 A1 | 9/2008 |
| WO | WO 2009/086547 | 7/2009 |
| WO | WO 2009148698 A1 | 12/2009 |
| WO | WO 2010/060098 A1 | 5/2010 |
| WO | 2013016696 A1 | 1/2013 |
| WO | 2014172663 A1 | 10/2014 |
| WO | 2014201026 A2 | 12/2014 |

OTHER PUBLICATIONS

U.S. Appl. No. 12/528,067 Non Final Office Action dated Jan. 4, 2012.
U.S. Appl. No. 12/528,067 Notice of Allowance dated Jul. 16, 2012.
U.S. Appl. No. 12/811,197 Restriction Requirement dated Jul. 17, 2012.
U.S. Appl. No. 12/811,197 Non-Final Office Action dated Dec. 5, 2012.
U.S. Appl. No. 13/114,539 Restriction Requirement dated May 25, 2012.
U.S. Appl. No. 13/114,539 Non-Final Office Action dated Oct. 2, 2012.
European Application No. 08731097.5 Extended Search Report dated Jun. 15, 2011.
EP Application No. 09828387.2 Supplemental Search Report dated Aug. 10, 2012.
Japanese Application No. 2009-551871 Official Action dated Dec. 21, 2011.
Abaza et al., Effects of amino acid substitutions outside and antigenic site on protein binding to monoclonal antibodies of predetermined specificity obtained by peptide immunization: demonstration with region 94-100 (antigenic site 3) of myoglobin, Journal of Protein Chemistry, vol. 11, No. 5, 1992, pp. 433-444.
Colman, P.M., Effects of amino acid sequence changes on antibody-antigen interactions, Biomolecular Research Institute, 343 Royale Parade, Parkville, 3052 (Australia), Research in Immunology, No. 1, vol. 145, 1994, pp. 33-35.
Conklin. Cancer chemotherapy and antioxidants, J. Nutri., 2004, vol. 134, pp. 3201A-3204A.
Casolaro et al. Redox-active Polymers: Sythesis and Exchange Reaction of Amino Compounds Containing a Cyclic Disulfide. Polymer (1994). 35(2): pp. 360-366.
Fujimoto et al. Synthesis of a Polymer Containing the Cyclic Disulfide (1, 2-Dithiolane) Structure. Die Makromolekulare Chemie (1974). 175: pp. 3597-3602.
Hus et al. Synthesis of functionalized 1,3-propanedithiols as derivatizing reagent for organoarsenic (III) compounds. Proceed. ERDEC Sci. Conf. Clin. Biol. Defense Res., Aberdeen Proving Ground. Nov. 17-20, 1998. Abstract.
Kalyuzhny et al. Ligand effects on optical properties of CdSe nanocrystals. Journal of Physical Chemistry B. (2005). 109(15): pp. 7012-7021. Abstract.
Kieller et al. The Five-membered Disulfide Ring System. III. Antineoplastic Potentialities. Acta Biochimica Polonica (1964). 11(2-3): pp. 279-291.
Kunii et al. Preparation and antitumor characteristics of PLA/(PEG-PPG-PEG) nanoparticles loaded with camptothecin. European Journal of Pharmaceuticals and Biopharmaceuticals. (2007) 67(1):9-17.
Lederman et al., A single amino acid substitution in a common african allele of the CD4 molecule ablates binding of the monoclonal antibody, OKT4, Molecur Immunology, vol. 28, No. 11, pp. 1171-1181, 1991.
Lee et al. Nereistoxin and Cartap Neurotoxicity Attributable to Direct Block of the Insect Nicotinic Receptor/Channel. Journal of Agricultrual and Food Chemistry. (2003). 51(9): pp. 2646-2652. Abstract.
Moon et al. Antibody Conjugates of 7-Ethyl-10-hydroxycamptothecin (SN-38) for Targeted Cancer Chemotherapy. J. Med. Chem (2008). 51(21):6916-6926.
Pham et al., Thermodynamic and strutural characterization of 2-nitrogen-modified RNA duplexes, Nucleic Acids Research, 2004, vol. 32, No. 11, pp. 3446-3455.
Povalyaeva et al. Synthesis and Properties of N-substituted 4-amino-1, 2, dithiolanes and Related Compounds. Zhurnal Organicheskoi Khimii. (2004). 20(4): pp. 849-860.
Rice et al. Inhibition of multiple phases of human immunodeficiency virus type I replication by a dithiane compound that attacks the conserved zinc fingers of retroviral nucleocapsid proteins. Antimicrob Agents Chemother. (1997). 41(2): pp. 419-426.
Schotte et al. Five-membered Disulfide Ring System. I. General Chemistry and Therapeutic Aspects. Biochemical Pharmacology. (1962). 11. Abstract.
Sieczkowska et al. Sythesis and Characterization of Photolabile Aminoterpolymers for Covalent Attachment onto Gold Substrates. Designed Monomers and Polymers (2005). 8(6): pp. 629-644.
Sun et al. Ultrathin Self-Assembled Polymeric Films on Solid Surfaces. I. Synthesis and Characterization of Acrylate Copolymers Containing Alkyl Disulfide Side Chains. Journal of Polymer Science: Part A: Polymer Chemistry. (1993). 31: pp. 1729-1740.
Sun et al. Ultrathin Self-Assembled Polymeric Films on Solid Surfaces. III. Influence of Acrylate Dithioalkyl Side Chain Length on Polymeric Monolayer Formation of Gold. J. Vac. Sci. Technol. A (1994). 12(4): pp. 2499-2506.
Thomas et al. Campthotecin: Current Perspectives. Bioorg Med Chem. (2004): 12: pp. 1585-1604. Abstract.
Van Regenmortel et al. Mapping epitope structure and activity: from one-dimensional prediction to four-dimensional description of antigenic specifity, Methods: A Companion to Methods in Enzymology 9, (1996), pp. 465-472.
PCT/US2012/048703 International Search Report dated Dec. 7, 2012; 4 pages.
PCT/US2012/048703 Written Opinion dated Dec. 7, 2012; 5 pages.
PCT/US2012/048703 International Preliminary Report on Patentability dated Jan. 28, 2014; 6 pages.
Gruzman et al. Synthesis and characterization of new and potent a-lipoic acid derivatives. Bioorganic & Medicinal Chemistry (2004). 12:1183-1190.
Lee et al. Oxidative stimuli-responsive nanoprodrug of camptothecin kills glioblastoma cells. Bioorganic & Medicinal Chemistry Letters (2010). 20:5262-5268.
Zhang et al. Folate-decorated poly(lactide-co-glycolide)-vitamin E TPGS nanoparticles for targeted drug delivery. Biomaterials (2007)/ 28:1889-1899.
EP Application No. 12818061.9 Partial Search Report dated Mar. 6, 2015.
PCT/US2014/034691 International Search Report and Written Opinion dated Sep. 2, 2014.
PCT/US2014/041752 International Search Report and Written Opinion dated Dec. 4, 2014; 10 pages.
PCT/US2014/041752 International Preliminary Report on Patentability dated Dec. 23, 2015; 7 pages.

* cited by examiner

FIG. 1C
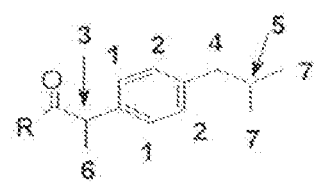
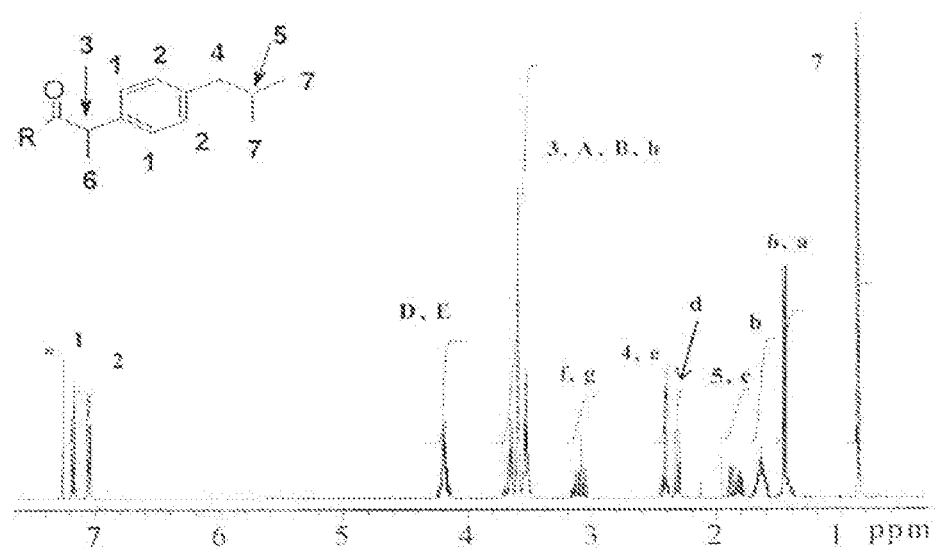
FIG. 1D
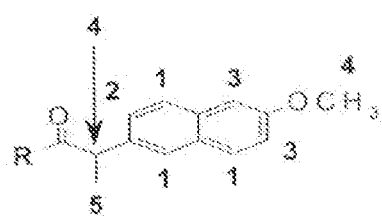
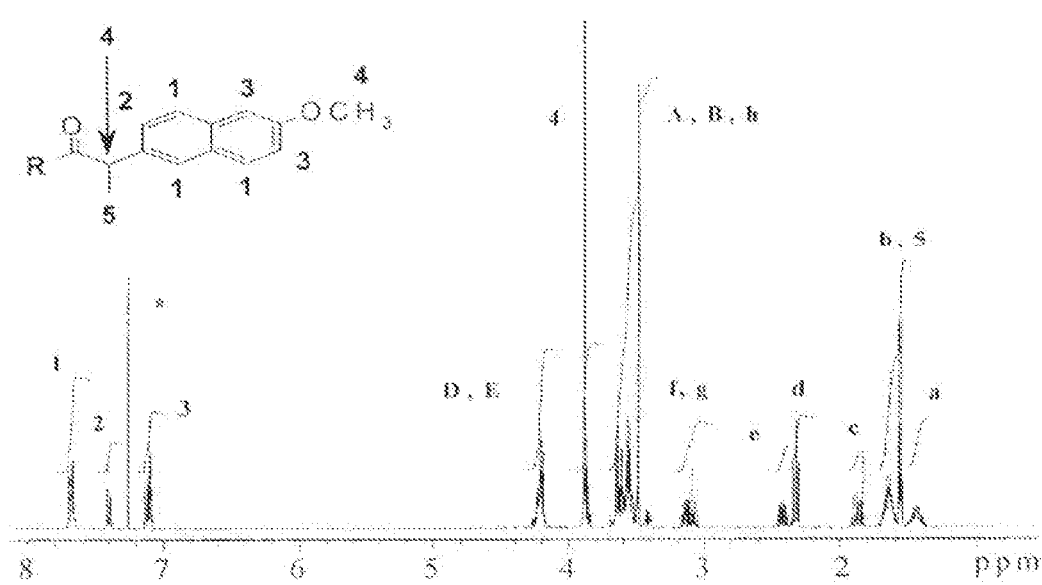

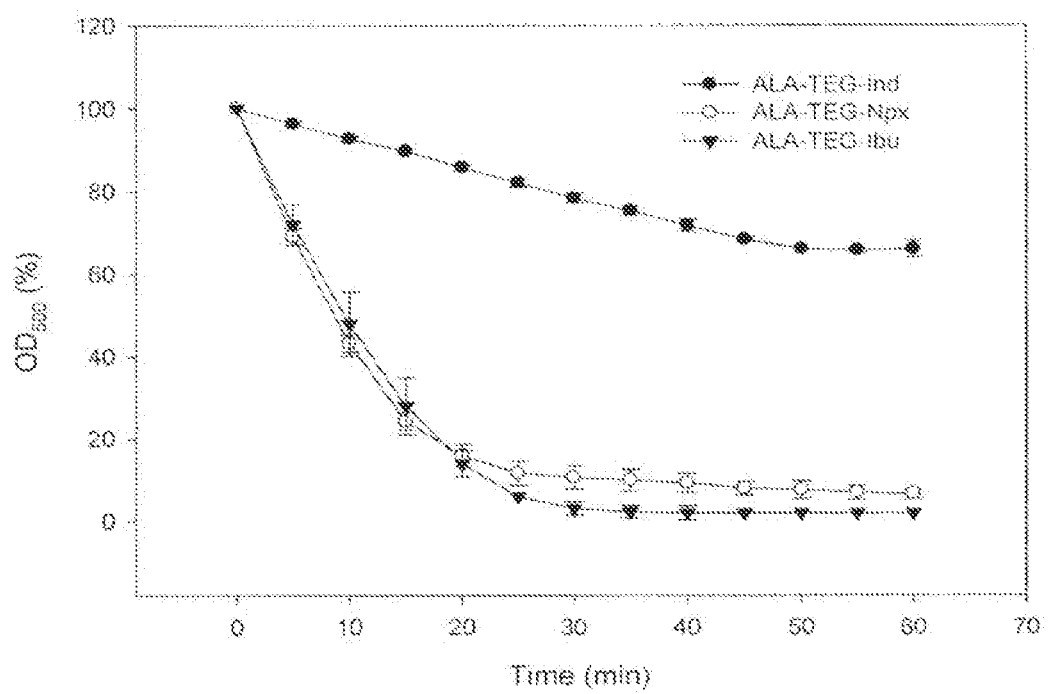
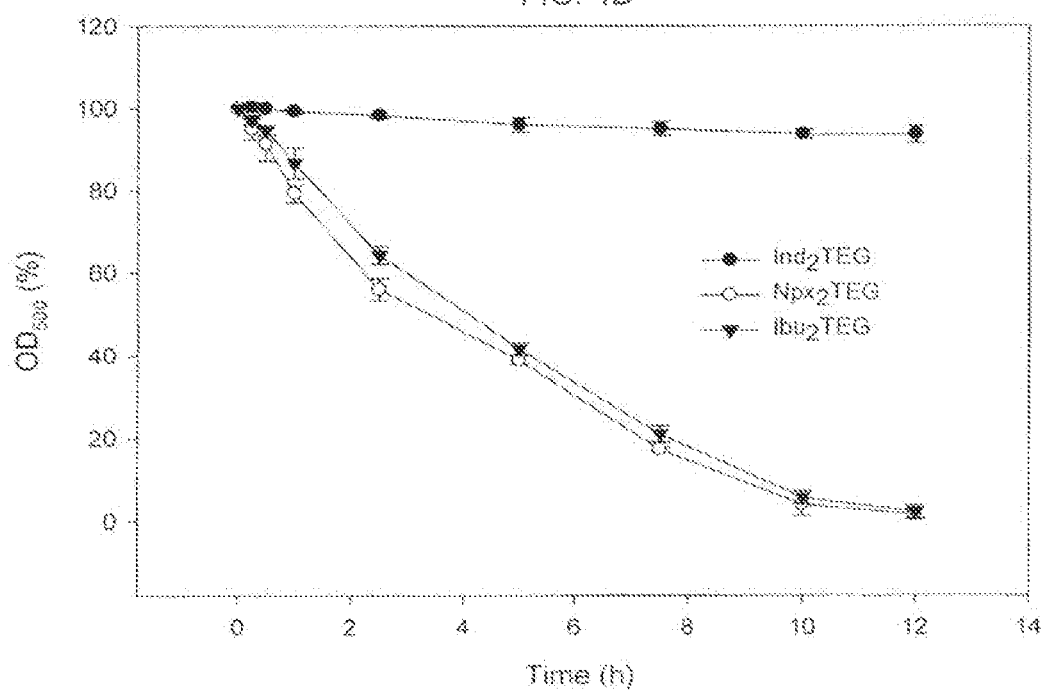

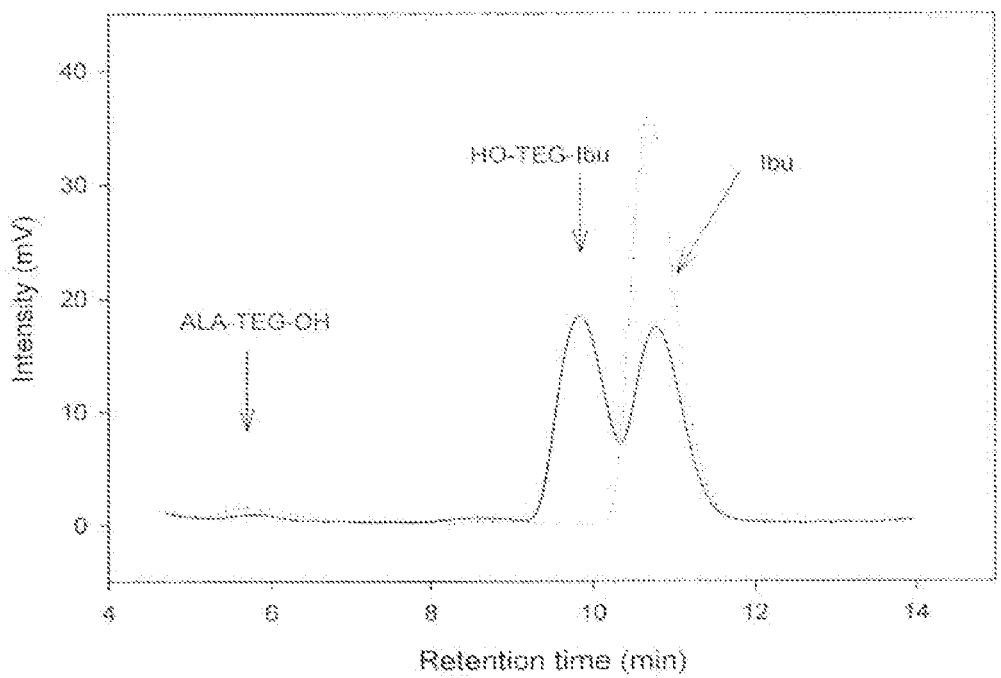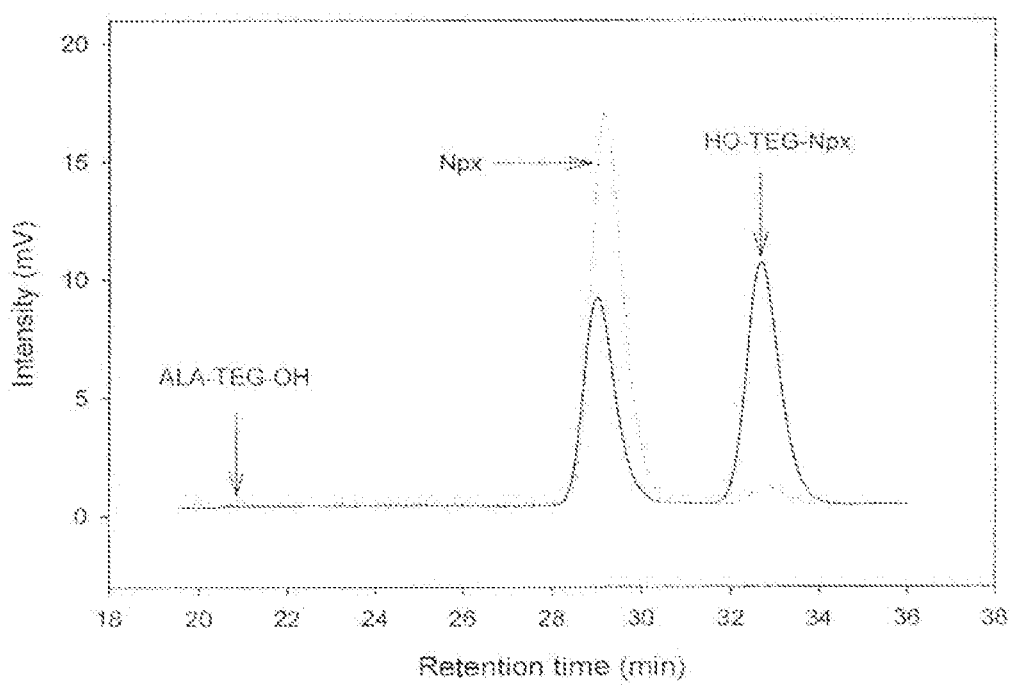

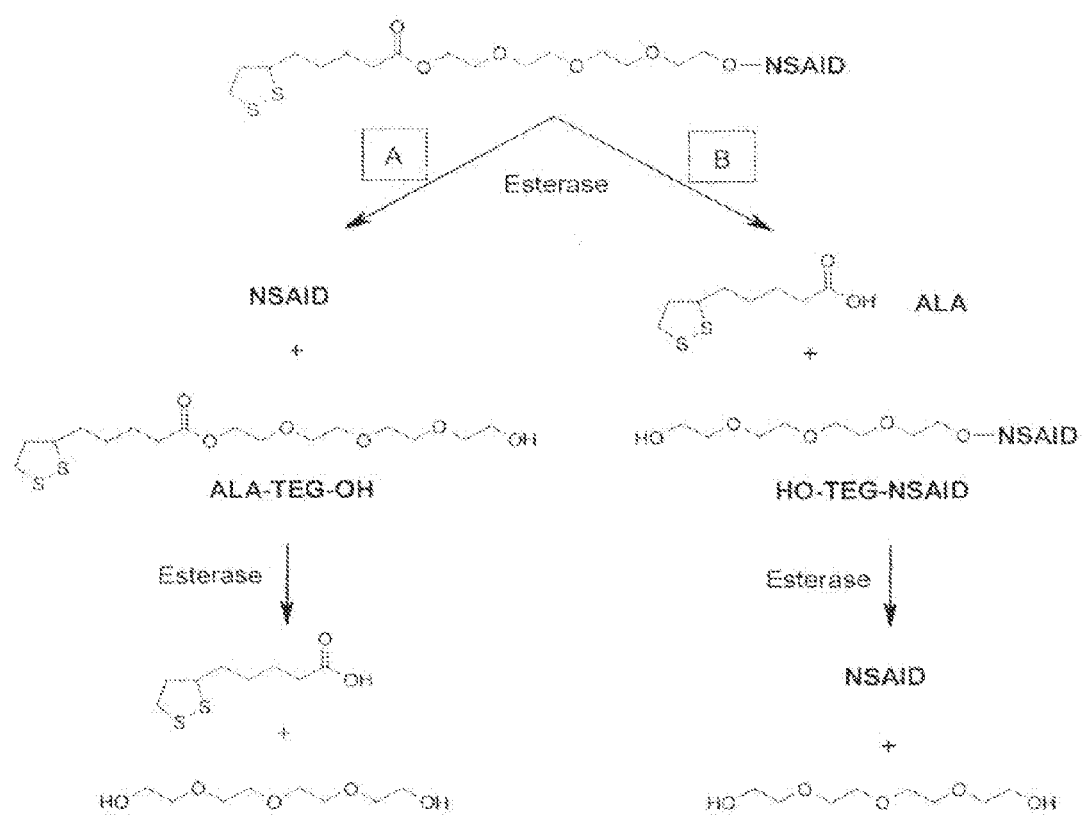

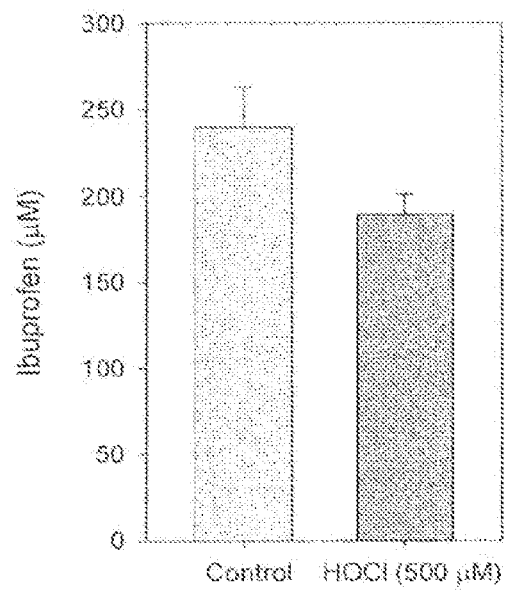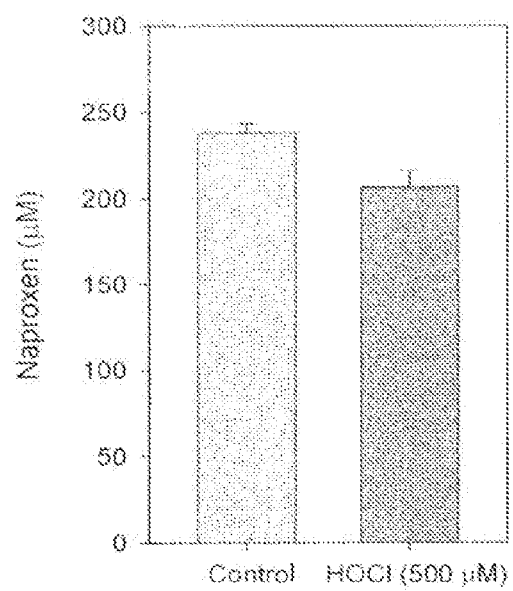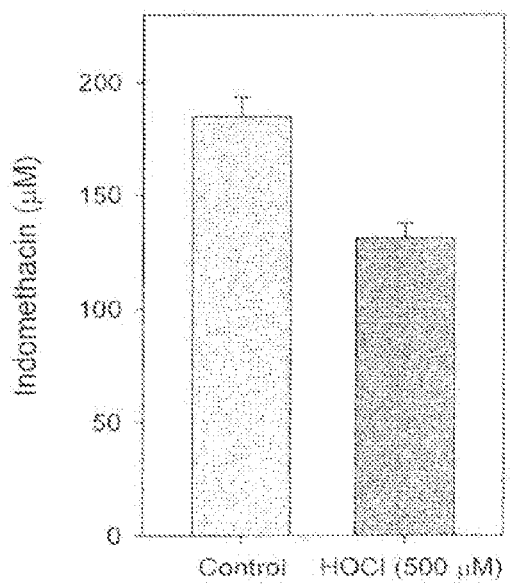

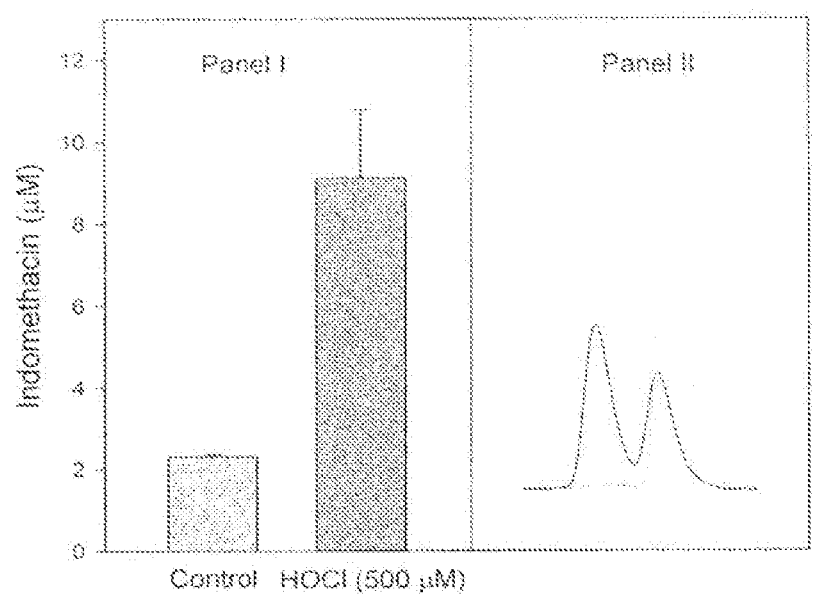

FIG. 16
A
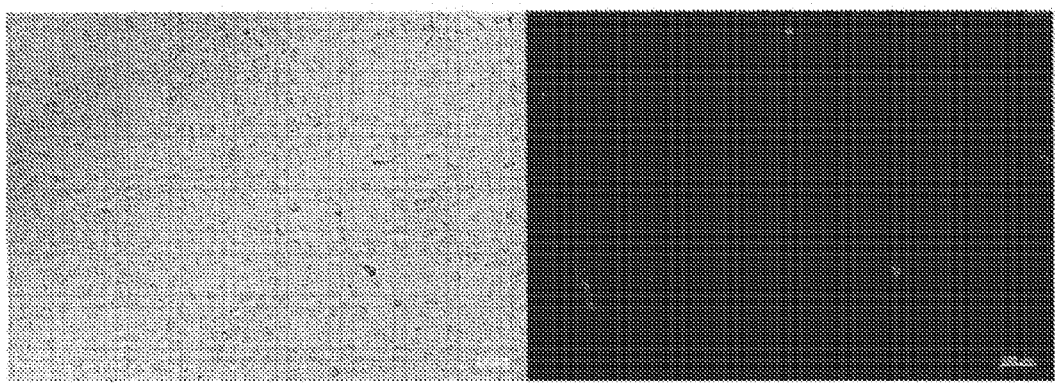
B
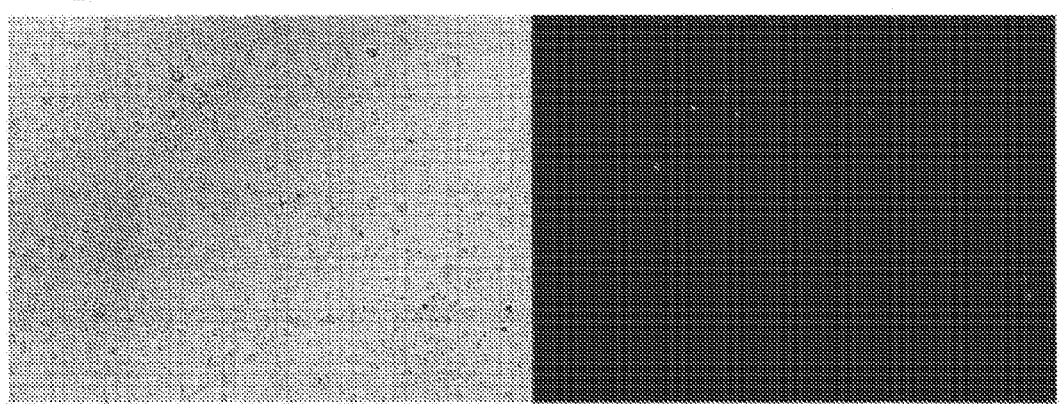
C
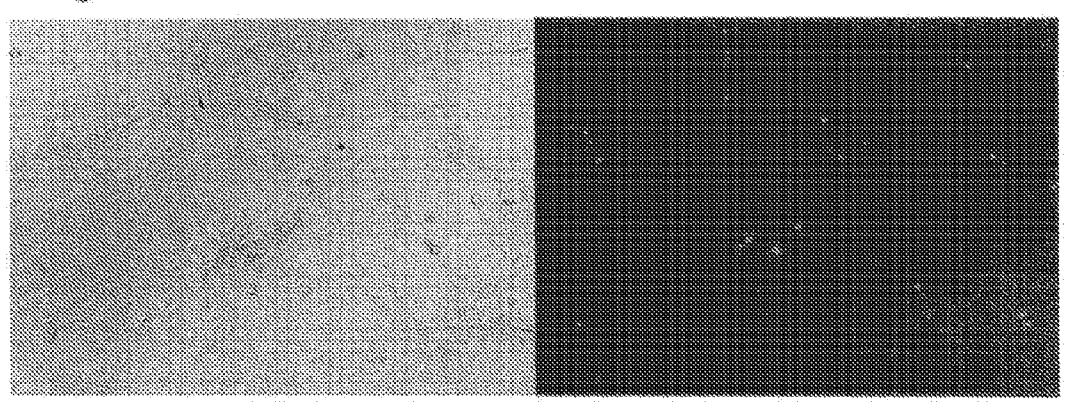

FIG. 16
D
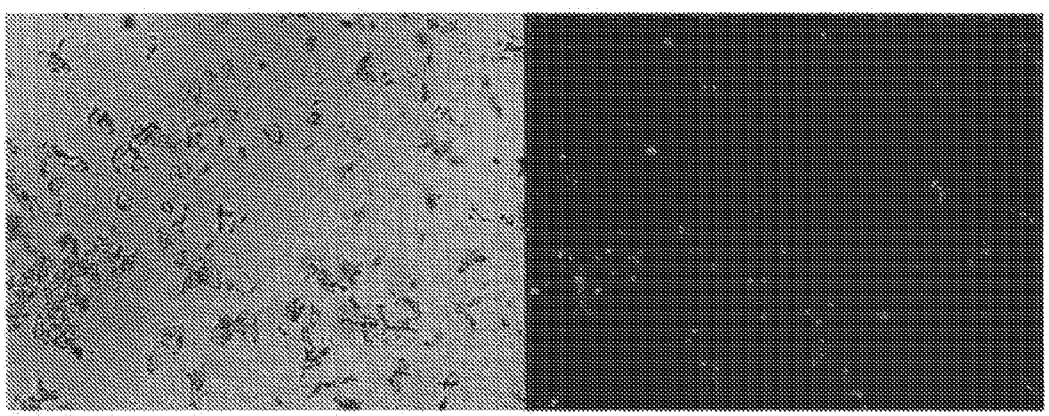
E
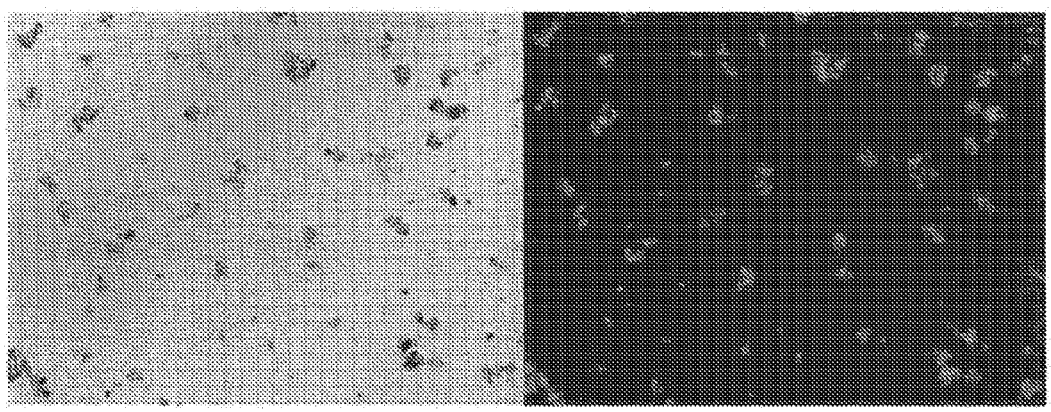

NANOMETER-SIZED PRODRUGS OF NSAIDS

FIELD OF INVENTION

This invention relates to derivatives of non-steroidal anti-inflammatory drugs (NSAIDs) and nanospheres thereof.

BACKGROUND

All publications herein are incorporated by reference to the same extent as if each individual publication or patent application was specifically and individually indicated to be incorporated by reference. The following description includes information that may be useful in understanding the present invention. It is not an admission that any of the information provided herein is prior art or relevant to the presently claimed invention, or that any publication specifically or implicitly referenced is prior art.

Non-Steroidal Anti-Inflammatory Drugs

Non-steroidal anti-inflammatory drugs (NSAIDs) are widely used in the treatment of pain, fever, and inflammation. The major mechanism by which NSAIDs exert their anti-inflammatory activity is the inhibition of cyclooxygenase-derived prostaglandin synthesis, which is also responsible for adverse side effects, such as irritation and ulceration of the gastrointestinal (GI) mucosa (Whittle, 2003). There are two types of COX enzymes, namely COX-1 and COX-2. COX-1 is expressed constitutively in many tissues, whereas COX-2 is expressed only at the site of inflammation (S. Kargan et al. GASTROENTEROL., 111: 445-454, 1996). The prostaglandins whose production is mediated by COX-1 are responsible for the maintenance of gastric mucosal integrity. Thus, the GI side effects are generally believed to result from the combined effect of the irritation caused by the free carboxylic groups in NSAIDs and blockage of prostaglandin biosynthesis in the GI tract (Dannhardt and Kiefer, 2001). In addition to the side effect which is attributed to their inhibitory effect on the activity of cyclooxygenase, the acidic moiety of these NSAIDs also contributes to the gastrointestinal side effect observed in response to these drugs (Tammara et al., 1993).

Epidemiologic studies have documented that a subset of NSAIDs decrease the risk for Alzheimer's disease (AD). The efficacy of NSAIDs in AD might be attributable to either anti-inflammatory or anti-amyloidogenic activities. It has been reported that ibuprofen, indomethacin and sulindac sulphide decrease the highly amyloidogenic Aβ42 peptide independently of COX activity (NATURE, 414:212-216 (2001)).

NSAIDs have also been shown to inhibit angiogenesis through direct effects on endothelial cells.

Although inflammatory oxidant hypochlorous acid (HOCl) generated by the myeloperoxidase (MPO)—$H_2O_2$/$Cl^-$ system comprises an important mechanism of host defense against infection, the overproduction and extracellularly generated HOCl is cytotoxic and is believed to be implicated in the pathogenesis of numerous diseases including neurodegenerative disorders, atherosclerosis, chronic inflammatory conditions, and cancer (Malle et al., BR J PHARMACOL 2007: 1-17).

Hypochlorous acid is a powerful oxidizing agent that can react with many biological molecules. In the presence of physiological concentration of chloride ions, $H_2O_2$ is efficiently halogenated by the heme enzyme MPO to yield hypochlorous acid, by far the most abundant oxidant generated by activated phagocyte cells (Krasowska et al., BRAIN RES. 997:176-184 (2004)). Hypochlorous acid can chlorinate cytosolic proteins and nuclear DNA bases and induce lipid peroxidation in phospholipid and lipoprotein (Spickett C M., PHARMACOL THERAPEUTICS 115:400-409 (2007)). Importantly, the damages caused by HOCl to the intracellular glutathione and protein thiols are irreversible and can be replaced only by resynthesis (Dalle-Donne et al., FREE RADIC BIOL MED 32(9):927-937 (2002)). Furthermore, HOCl can be converted into damaging hydroxyl radicals (Candeias et al., FEBS LETT 333(1,2):151-153 (1993)). Most NSAIDs are able to scavenge hypochlorous acid in the aqueous environment and some NSAIDs inhibit the MPO by direct interaction with the enzyme (Neve et al., EUROPEAN J PHARMACOL 417:37-43 (2001)).

Anticancer Effects of NSAIDs

A number of epidemiologic studies, clinical trials, and animal studies have shown that NSAIDs may be effective in the prevention and treatment of certain cancers. (Keller et al., *Chemoprevention strategies using NSAIDs and COX-2 inhibitors*. CANCER BIOL THER (2003) 2:S140-9; Gupta et al., *Colorectal cancer prevention and treatment by inhibition of cyclooxygenase-2*. NAT REV CANCER (2001) 1:11-21; Umar et al., *Development of COX inhibitors in cancer prevention and therapy*. AM J CLIN ONCOL (2003) 26:S48-57; Harris et al., *Aspirin, ibuprofen, and other non-steroidal anti-inflammatory drugs in cancer prevention: a critical review of non-selective COX-2 blockade [review]*. ONCOL REP 2005; 13: 559-83). It has also been suggested that the long term use of certain NSAIDs reduces the risk of colorectal, breast, and ovarian cancer. Taketo et al., *Cyclooxygenase-2 inhibitors in tumorigenesis*. J NATO CANCER INST (1998) 90:1529-36; Sandler et al. *A randomized trial of aspirin to prevent colorectal adenomas*. N ENGL J MED (2003) 348:891-9; Saji et al. *Novel sensitizing agents: potential contribution of COX-2 inhibitor for endocrine therapy of breast cancer*. BREAST CANCER (2004) 11:129-33.

The molecular mechanisms by which NSAIDs exhibit antineoplastic effects are poorly understood and a matter of intensive investigation. The chemopreventive and antitumorigenic effects of NSAIDs are partially attributed to the induction of apoptosis followed by inhibition of COX-2. Lin et al., *The role of cyclooxygenase-2 inhibition for the prevention and treatment of prostate carcinoma*. CLIN PROSTATE CANCER (2003) 2:119-26; Mann et al., *Cyclooxygenase-2 and gastrointestinal cancer*. CANCER J (2004) 10:145-52; Basler et al., *Nonsteroidal anti-inflammatory drugs and cyclooxygenase-2 selective inhibitors for prostate cancer chemoprevention*. J UROL 2004; 171: S59-62; discussion S62-53; Sabichi et al., *COX-2 inhibitors and other nonsteroidal anti-inflammatory drugs in genitourinary cancer*. SEMIN ONCOL 2004; 31:36-44.

Various studies have also suggested that a COX-2-independent mechanism may also be involved because apoptosis induction by NSAIDs does not always correlate with their ability to inhibit COX-2. Chuang et al., *COX-2 inhibition is neither necessary nor sufficient for celecoxib to suppress tumor cell proliferation and focus formation in vitro*. MOL CANCER (2008) 7:38; Marx et al., J. Cancer research; Anti-inflammatories inhibit cancer growth—but how? SCIENCE 2001; 291:581-2; Elder et al., *Induction of apoptotic cell death in human colorectal carcinoma cell lines by a cyclooxygenase-2 (COX-2)-selective nonsteroidal anti-in-* flammatory drug: independence from COX-2 protein expression. CARCINOGENESIS (2001) 22:17-25; Jiang et al., Subtraction hybridization identifies a novel melanoma differentiation associated gene, mda-7, modulated during human melanoma differentiation, growth and progression. ONCOGENE (1995) 11:2477-86.

α-Lipoic Acid

Molecules containing a dithiolane moiety are widely investigated due to their antioxidant properties. α-Lipoic acid (thioctic acid, 1,2-dithiolane-3-pentanoic acid), which has dithiolane ring in its molecule, is a widely distributed natural substance which was originally discovered as a growth factor. Physiologically, it acts as a coenzyme of the oxidative decarboxylation of α-keto carboxylic acid (e.g., pyruvates) and as an antioxidant, and it is able to regenerate vitamin C, vitamin E, glutathione and coenzyme Q10. In pathological conditions, lipoic acid is applied in the treatment of diabetic polyneuropathy, liver cirrhosis and metal intoxications.

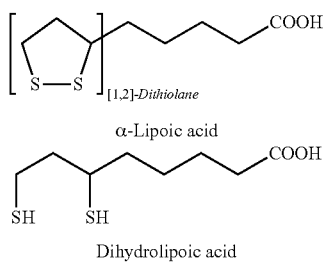

Lipoic acid and dihydrolipoic acid are capable of trapping a number of radicals both in a lipid and in an aqueous environment. Lipoic acid and dihydrolipoic acid act as antioxidants not only by direct radical trapping and/or metal chelation but also by recycling other antioxidants (e.g., vitamin C, vitamin E) and by reducing glutathione, which in turn recycles vitamin E. The two thiol groups present in [1,2]-dithiolane ring system confer it a unique antioxidant potential. The disulfides with a cyclic five-member ring such as lipoic acid have been found to be more effective in reductive and/or nucleophilic attack than open-chain derivatives such as cystine or glutathione.

The antioxidant potential of a compound may be evaluated based on the properties such as (1) specificity of free radical scavenging, (2) interaction with other antioxidants, (3) metal-chelating activity, (4) effects on gene expression, (5) absorption and bioavailability, (6) location (in aqueous or membrane domains, or both), and (7) ability to repair oxidative damage (Packer et al., FREE RADICAL BIOLOGY & MEDICINE. 19(2):227-250, 1995). According to the above criteria, the [1,2]-dithiolane containing lipoic acid/dihydrolipoic acid redox system has been regarded as a universal antioxidant.

There have been many attempts to develop lipoic acid derivatives or complexes having antioxidant activity. U.S. Pat. Nos. 6,090,842; 6,013,663; 6,117,899; 6,127,394; 6,150,358; 6,204,288; 6,235,772; 6,288,106; 6,353,011; 6,369,098; 6,387,945; 6,605,637; 6,887,891; 6,900,338; and 6,936,715 are some examples.

In many other U.S. patents, the natural and synthetic lipoic acid derivatives and their metabolites are disclosed for use in preventing skin aging and in the treatment of free radical mediated diseases, including inflammatory, proliferative, neurodegenerative, metabolic and infectious diseases.

Inhibitory Activity on NO-Synthase and Trapping the Reactive Oxygen Species (ROS)

Various conditions or disease conditions have demonstrated a potential role of nitric oxide (NO) and the ROS's and the metabolism of glutathione in their physiopathology. These conditions and disease conditions are characterized by an excessive production or a dysfunction of nitrogen monoxide and/or the metabolism of glutathione and of the redox status of the thiol groups (Duncan and Heales, Nitric Oxide and Neurological Disorders, MOLECULAR ASPECTS OF MEDICINE. 26:67-96, 2005; Kerwin et al., Nitric Oxide: A New Paradigm For Second Messengers, J. MED. CHEM. 38:4343-4362, 1995; Packer et al., FREE RADICAL BIOLOGY & MEDICINE. 19:227-250, 1995). U.S. Pat. Nos. 6,605,637, 6,887,891, and 6,936,715 disclose that lipoic acid derivatives inhibit the activity of NO-synthase enzymes producing nitrogen monoxide NO and regenerate endogenous antioxidants which trap the ROS and which intervene in a more general fashion in the redox status of thiol groups. U.S. Pat. Nos. 5,693,664, 5,948,810, and 6,884,420 disclose the use of racemic α-lipoic acid or their metabolites, salts, amides or esters for the synthesis of drugs for the treatment of diabetes mellitus of types I and II. U.S. Pat. No. 5,925,668 discloses a method of treating free radical mediated diseases, and/or reducing the symptoms associated with such diseases whereby the compounds with antioxidant activity contain 1,2-dithiolane, reduced or oxidized forms. U.S. Pat. No. 6,251,935 discloses methods for the prevention or treatment of migraine comprising the administration of an active ingredient selected from the group consisting of racemic alpha-lipoic acid, enantiomers and pharmaceutically acceptable salts, amides, esters or thioesters thereof. U.S. Pat. Nos. 6,472,432 and 6,586,472 disclose the treatment of a chronic inflammatory disorder rosacea by application of a composition containing lipoic acid and/or lipoic acid derivatives. There is also strong evidence that the neuroprotective effects of lipoic acid and dihydrolipoic acid are mediated by antioxidant and free radical scavenging mechanisms (Packer et al., FREE RADICAL BIOLOGY & MEDICINE. 22:359-378, 1997).

There is much interest in developing prodrugs that can be activated in response to stimuli and enable specific sustained drug release to reduce side effects (Friedrich et al., 1999; McKenzie et al., 2000; Rodrigues et al., 2003; Fattal et al., 2004; Ulbrich and Šubr, 2004). Stimuli-responsive materials have great potential in drug delivery when they are capable of forming vesicles allowing encapsulation or incorporation of drugs into their vesicular structures. Certain environmental stimuli, such as pH or oxidative molecules (Bellomo et al., 2004; Napoli et al., 2004), can destabilize vesicles allowing the release of drugs at the site of stimulation. This increases the selectivity of the drugs, improves therapeutic efficiency, and reduces adverse side effects. The prodrug strategy offers a similar advantage over parent drugs by introducing bioreversible bonds (Rautio et al., 2008). These bonds undergo selective enzymatic or chemical transformations in vivo and yield a significant reduction of adverse side effects.

Various prodrugs have been proposed which attempt to alleviate the NSAID's adverse side effects as well as to improve their delivery characteristics by masking the carboxylic acid groups through the formation of bioreversible bonds (Bonina et al., 2001; Chandrasekaran et al., 2006;

Siskou et al., 2007; Velázquez et al., 2007). However, there still exists a need to develop a new NSAID prodrug strategy which integrates enzymatic activation of prodrugs with the stimuli-responsiveness to increase the potential for site selective activation.

Described herein, are NSAID prodrugs that integrate enzymatic activation of prodrugs with the stimuli-responsiveness to increase the potential for site selective activation.

SUMMARY OF THE INVENTION

The following embodiments and aspects thereof are described and illustrated in conjunction with compositions and methods which are meant to be exemplary and illustrative, not limiting in scope.

The present invention also provides for a molecule having formula I:

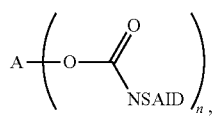

wherein the A may be selected from the group consisting of branched and unbranched alkyl, branched and unbranched alkenyl, branched and unbranched alkynyl, heteroatom-containing branched and unbranched alkyl, heteroatom-containing branched and unbranched alkenyl, heteroatom-containing branched and unbranched alkynyl, aryl, cyclic aliphatic, cyclic aromatic, heterocyclic, and aromatic heterocyclic groups; and n may be an integer of at least two.

In various embodiments, A may be a moiety that is formed by esterification of at least two free esterifiable hydroxyl groups on a polyol. In one embodiment, the polyol may be

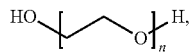

wherein n on the polyol may be an integer between 1 and 6. In another embodiment, the polyol may be

wherein n on the polyol may be an integer between 3 and 16.

In other embodiments, A may be formed from esterification of a polyol selected from group consisting of an ethylene glycol, diethylene glycol, triethylene glycol, tetraethylene glycol, pentaethylene glycol, hexaethylene glycol, 1,3-propanediol, and 1,4-butanediol.

In various embodiments, the NSAID may be selected from the group consisting of aspirin, ibuprofen, flurbiprofen, ketoprofen, fenoprofen, fenbufen, naproxen, indomethacin, diclofenac, ketorolac, tolmetin, flufenamic acid, mefenamic acid, tolfenamic acid, meclofenamic acid, niflumic acid, sulindac, sulindac sulfide and combinations thereof.

The present invention also provides a molecule having the formula II

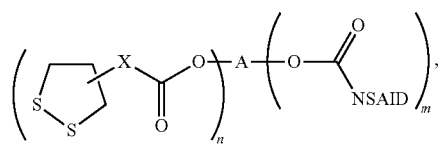

wherein X may be selected from the group consisting of a substituted, unsubstituted, branched or unbranched chain of carbon atoms and may optionally contain a heteroatom; A may be selected from the group consisting of branched and unbranched alkyl, branched and unbranched alkenyl, branched and unbranched alkynyl, heteroatom-containing branched and unbranched alkyl, heteroatom-containing branched and unbranched alkenyl, heteroatom-containing branched and unbranched alkynyl, aryl, cyclic aliphatic, cyclic aromatic, heterocyclic, and aromatic heterocyclic groups; n may be an integer of at least one; and m may be an integer of at least one.

In various embodiments, A may be a moiety that is formed by esterification of at least two free esterifiable hydroxyl groups on a polyol. In particular embodiments, the polyol may be

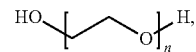

wherein n on the polyol may be an integer between 1 and 6, or

wherein n on the polyol may be an integer between 3 and 16.

In various embodiments, the NSAID may be selected from the group consisting of aspirin, ibuprofen, flurbiprofen, ketoprofen, fenoprofen, fenbufen, naproxen, indomethacin, diclofenac, ketorolac, tolmetin, flufenamic acid, mefenamic acid, tolfenamic acid, meclofenamic acid, niflumic acid, sulindac, sulindac sulfide and combinations thereof.

In one embodiment, the dithiolane moiety may be an α-lipoic acid ("ALA") and is represented by formula III:

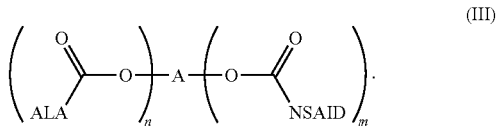

The present invention also provides for a nanosphere, comprising a molecule represented by formulas I, II or III.

The present invention also provides for a nanosphere, comprising a molecule represented by formulas I, II or III and a molecule represented by formula IV,

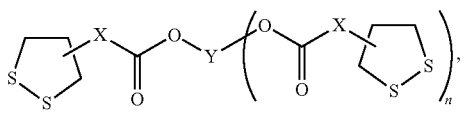

(IV)

wherein X may be selected from the group consisting of a substituted, unsubstituted, branched or unbranched chain of carbon atoms and may optionally contain a heteroatom; Y may be selected from the group consisting of branched and unbranched alkyl, branched and unbranched alkenyl, branched and unbranched alkynyl, heteroatom-containing branched and unbranched alkyl, heteroatom-containing branched and unbranched alkenyl, heteroatom-containing branched and unbranched alkynyl, aryl, cyclic aliphatic, cyclic aromatic, heterocyclic, and aromatic heterocyclic groups; and n may be an integer of at least one.

In one embodiment, Y may be a moiety that is formed by esterification of at least two free esterifiable hydroxyl groups on a polyol.

In another embodiment, the molecule represented by formula IV may be a molecule represented by formula V:

(V)

In further embodiment, the nanosphere may further comprise a tocopherol or a polymer. In various embodiments, the polymer may be selected from the group consisting of a hydrophobic polymer, amphiphilic polymer, and hydrophobically modified hydrophilic polymer. In other embodiments, the polymer may be selected from the group consisting of a polyanhydride, polyester, polyorthoester, polyesteramide, polyacetal, polyketal, polycarbonate, polyphosphoester, polyphosphazene, polyvinylpyrrolidone, polydioxanone, poly(malic acid), poly(amino acid), polymer of N-2-(hydroxypropyl)methacrylamide (HPMA), polymer of N-isopropyl acrylamide (NIPAAm), polyglycolide, polylactide, copolymer of glycolide and lactide, and combinations thereof.

In various embodiments, the polymer may contain a side group selected from the group consisting of a hydrophobic molecule, hydrophilic molecule, and amphiphilic molecule. In various embodiments, the side group may be a therapeutic or diagnostic agent. In particular embodiments, the therapeutic agent may be a chemotherapeutic selected from the group consisting of paclitaxel, doxorubicin, temozolomide, 5-fluorouracil, and camptothecin. In other embodiments, the therapeutic agent may be selected from the group consisting of a peptide, antisense nucleic acid, and protein. In additional embodiments, the polymer may contain a hydrophobic side groups selected from the group consisting of an aromatic group, amino acid alkyl ester, and aliphatic group.

The present invention also provides for a method of treating a disease condition in a subject in need thereof, comprising: providing a therapeutically effective quantity of a nanosphere of the present invention administering the therapeutically effective quantity to the subject.

The present invention also provides for a method of delivering a therapeutic agent, comprising: providing a composition comprising the therapeutic agent and a nanosphere of the present invention; and administering the composition to the subject.

The present invention also provides for a composition comprising: a nanosphere comprising a molecule of represented by formulas I, II or III; and a nanosphere comprising a molecule having the formula IV or V.

Other features and advantages of the invention will become apparent from the following detailed description, taken in conjunction with the accompanying drawings, which illustrate, by way of example, various features of embodiments of the invention.

BRIEF DESCRIPTION OF THE FIGURES

Exemplary embodiments are illustrated in referenced figures. It is intended that the embodiments and figures disclosed herein are to be considered illustrative rather than restrictive.

FIGS. 1A-1G depict $^1$H NMR spectra of NSAID derivatives in accordance with an embodiment of the present invention. FIG. 1A, ALA-TEG-OH; FIG. 1B, ALA-TEG-Ind; FIG. 1C, ALA-TEG-Ibu; FIG. 1D, ALA-TEG-Npx; FIG. 1E, Ind$_2$TEG; FIG. 1F, Ibu$_2$TEG; FIG. 1G, Npx$_2$TEG.

FIGS. 4A-4B depict enzymatic destabilization of nanoprodrugs in accordance with an embodiment of the present invention. The results are calculated as the percentage of OD with 100% equal to the OD prior to the addition of esterase. The results are the mean±S.D. of three experiments.

FIGS. 5A-5D depict the sequence of enzymatic hydrolysis in accordance with an embodiment of the present invention.

FIGS. 6A-6C depict enzymatic hydrolysis of NSAIDs from oxidized nanoprodrugs in accordance with an embodiment of the present invention. The results are the mean±S.D. of three experiments.

FIGS. 7A-7C depict the influence of oxidation on the rate (A) and sequence (B) of enzymatic hydrolysis in accordance with an embodiment of the present invention. The results are the mean±S.D. of three experiments.

FIGS. 16A-16E depict the effect of nanoprodrug prepared from Ibu$_2$TEG on cell death in U87-MG human glioma cell line by propidium iodide incorporation in accordance with an embodiment of the present invention. Representative pictures of: control culture (FIG. 16A); control culture treated with DMSO (FIG. 16B); cells treat with 200 μM ibuprofen dissolved in DMSO (FIG. 16C); cells treated with 50 μM (FIG. 16D) or 100 μM (FIG. 16E) of the nanoprodrug prepared from Ibu$_2$TEG.

DESCRIPTION OF THE INVENTION

Figure 1A:
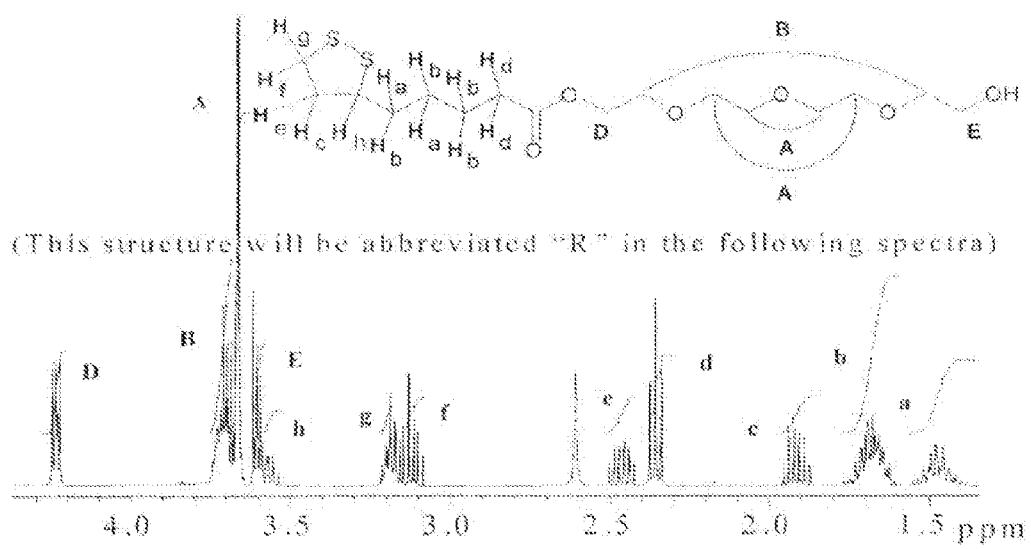
Figure 1B:
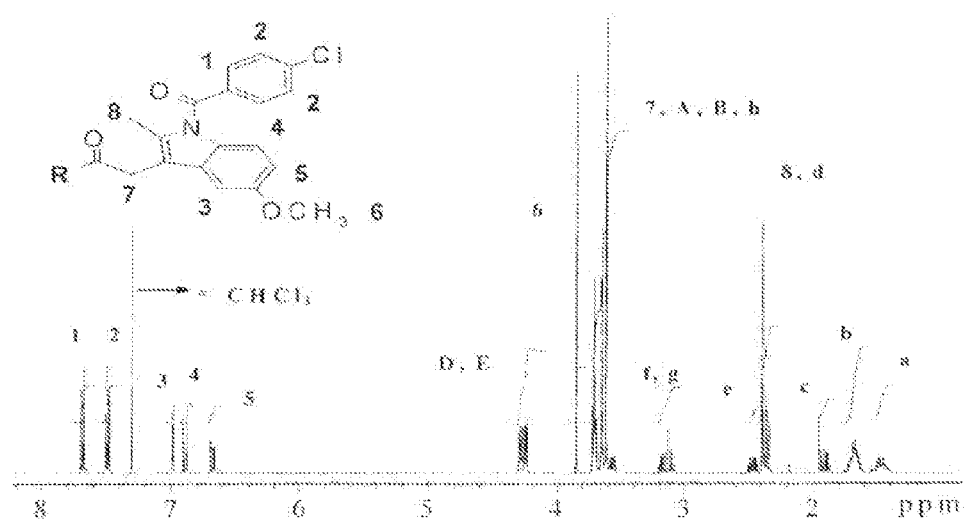
Figure 1E:
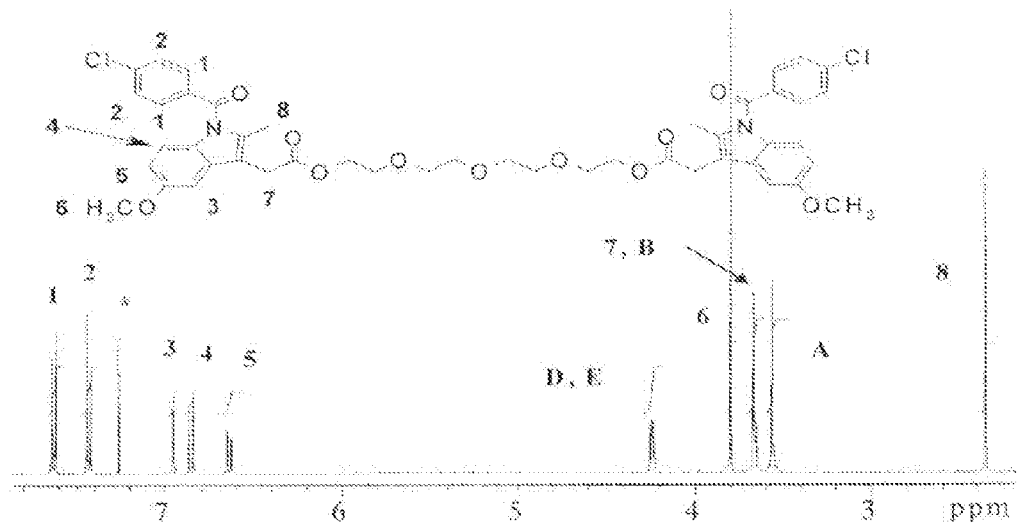
Figure 1F:
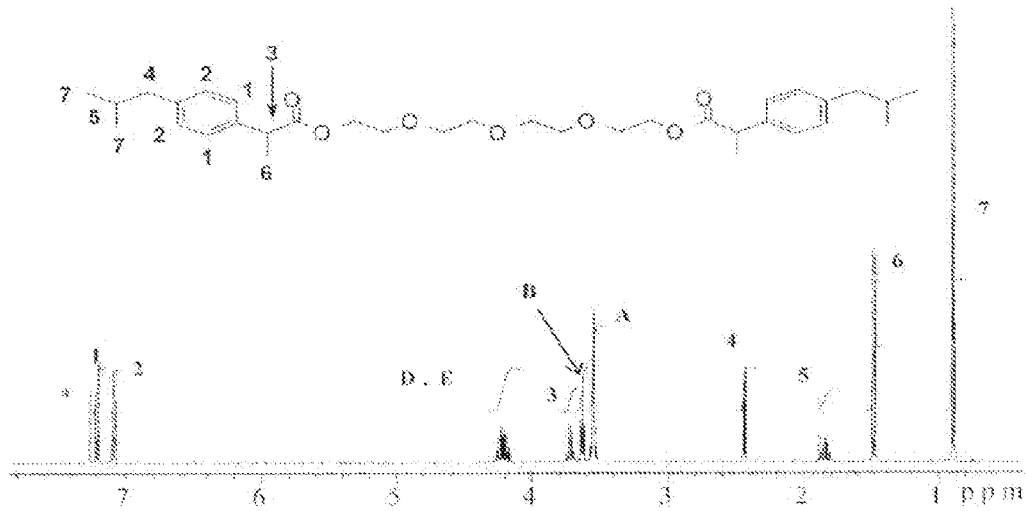
Figure 1G:
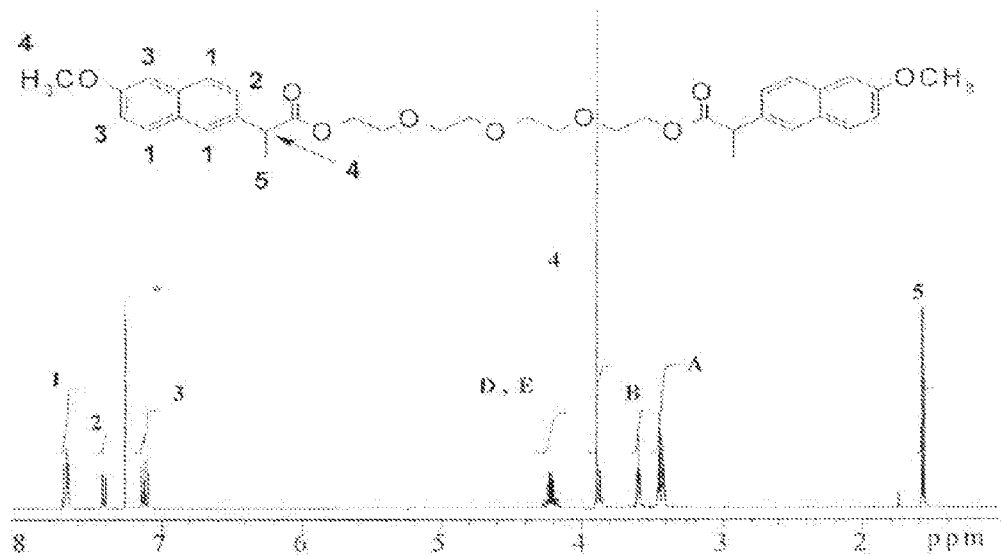

All references cited herein are incorporated by reference in their entirety as though fully set forth. Unless defined otherwise, technical and scientific terms used herein have the same meaning as commonly understood by one of ordinary skill in the art to which this invention belongs. Singleton et al., *Dictionary of Microbiology and Molecular Biology* 3$^{rd}$ ed., J. Wiley & Sons (New York, N.Y. 2001); March, *Advanced Organic Chemistry Reactions, Mechanisms and Structure* 5$^{th}$ ed., J. Wiley & Sons (New York, N.Y. 2001); and Sambrook and Russel, *Molecular Cloning: A Laboratory Manual* 3rd ed., Cold Spring Harbor Laboratory Press (Cold Spring Harbor, N.Y. 2001), provide one skilled in the art with a general guide to many of the terms used in the present application.

One skilled in the art will recognize many methods and materials similar or equivalent to those described herein, which could be used in the practice of the present invention. Indeed, the present invention is in no way limited to the methods and materials described. For purposes of the present invention, the following terms are defined below.

"Antineoplastic agent," as used herein, refers to a substance that decreases abnormal cell proliferation.

"Beneficial results" may include, but are in no way limited to, lessening or alleviating the severity of the disease condition, preventing the disease condition from worsening, curing the disease condition and prolonging a patient's life or life expectancy. The disease conditions may relate to or may be modulated by the central nervous system.

"Conditions" and "disease conditions," as used herein may include, but are in no way limited to conditions or disease conditions wherein the potential role of nitric oxide ("NO"), reactive oxygen species ("ROS") or the metabolism of glutathione have been demonstrated in their physiopathology, conditions or disease conditions caused by oxidative damage, or any form of neoplastic cell growth and proliferation, whether malignant or benign, pre-cancerous and cancerous cells and tissues.

Examples of conditions or disease conditions wherein the potential role of nitric oxide ("NO"), reactive oxygen species ("ROS") or the metabolism of glutathione have been demonstrated in their physiopathology and conditions or disease conditions caused by oxidative damage include but are not limited to cardiovascular and cerebrovasular disorders (e.g., atherosclerosis, migraine, arterial hypertension, septic shock, ischemic or hemorrhagic cardiac or cerebral infarctions, ischemias and thromboses); disorders of the central or peripheral nervous system (e.g., neurodegenerative nervous system); neurodegenerative diseases including cerebral infarctions, sub-arachnoid hemorrhaging, ageing, senile dementias (e.g., Alzheimer's disease), Huntington's chorea, Parkinson's disease, prion disease (e.g., Creutzfeld Jacob disease), amyotrophic lateral sclerosis, pain, cerebral and spinal cord traumas, addiction to opiates, alcohol and addictive substances, erective and reproductive disorders, cognitive disorders, encephalopathies, encephalopathies of viral or toxic origin, depression, anxiety, schizophrenia, epilepsy, sleeping disorders, eating disorders (e.g., anorexia, bulimia); disorders of the skeletal muscle and neuromuscular joints (e.g., myopathy, myositis), cutaneous diseases; proliferative and inflammatory diseases (e.g., atherosclerosis), pulmonary hypertension, respiratory distress, glomerulonephritis, cataracts, portal hypertension, psoriasis and rheumatoid arthritis, fibroses, amyloidoses, inflammations of the gastro-intestinal system (e.g., colitis, Crohn's disease) or of the pulmonary system and airways (e.g., asthma, sinusitis, rhinitis) as well as contact or delayed hypersensitivities; organ transplantation; auto-immune and viral diseases (e.g., lupus, AIDS, parasitic and viral infections), diabetes and its complications (e.g., retinopathies, nephropathies and polyneuropathies, multiple sclerosis, myopathies); cancer; autosomal genetic diseases (e.g., Unverricht-Lundborg disease); neurological diseases associated with intoxications (e.g., cadmium poisoning, inhalation of n-hexane, pesticides, herbicides), associated with treatments (e.g., radiotherapy) or disorders of genetic origin (e.g., Wilson's disease); and impotence linked to diabetes.

"Cancer" and "cancerous" refer to or describe the physiological condition in mammals that is typically characterized by unregulated cell growth. Examples of cancer include, but are not limited to, breast cancer, colon cancer, lung cancer, prostate cancer, hepatocellular cancer, gastric cancer, pancreatic cancer, cervical cancer, ovarian cancer, liver cancer, bladder cancer, cancer of the urinary tract, thyroid cancer, renal cancer, carcinoma, melanoma, head and neck cancer, and brain cancer; including, but not limited to, gliomas, glioblastomas, glioblastoma multiforme (GBM), oligodendrogliomas, primitive neuroectodermal tumors, low, mid and high grade astrocytomas, ependymomas (e.g., myxopapillary ependymoma, papillary ependymoma, subependymoma, anaplastic ependymoma), oligodendrogliomas, medulloblastomas, meningiomas, pituitary carcinomas, neuroblastomas, and craniopharyngiomas.

"Mammal" as used herein refers to any member of the class Mammalia, including, without limitation, humans and nonhuman primates such as chimpanzees and other apes and monkey species; farm animals such as cattle, sheep, pigs, goats and horses; domestic mammals such as dogs and cats; laboratory animals including rodents such as mice, rats and guinea pigs, and the like. The term does not denote a particular age or sex. Thus, adult and newborn subjects, as well as fetuses, whether male or female, are intended to be included within the scope of this term.

"Non-steroidal" as used herein distinguishes the anti-inflammatory drugs from steroids, which have a similar anti-inflammatory action.

"NSAID derivative" as used herein refers to a compound in which as least one NSAID molecule is coupled to a polyol; for example, through esterification.

"Therapeutic agent" as used herein refers to any substance used internally or externally as a medicine for the treatment, cure, prevention, slowing down, or lessening of a disease or disorder, even if the treatment, cure, prevention, slowing down, or lessening of the disease or disorder is ultimately unsuccessful.

"Therapeutically effective amount" as used herein refers to an amount which is capable of achieving beneficial results in a patient with a condition or a disease condition in which treatment is sought. A therapeutically effective amount can be determined on an individual basis and will be based, at least in part, on consideration of the physiological characteristics of the mammal, the type of delivery system or therapeutic technique used and the time of administration relative to the progression of the disease.

"Treatment" and "treating," as used herein refer to both therapeutic treatment and prophylactic or preventative measures, wherein the object is to prevent, slow down and/or alleviate the disease or disease condition even if the treatment is ultimately unsuccessful.

"Polyol" as used herein refers to a compound that contains at least two free esterifiable hydroxyl groups.

"Nanosphere" as used herein refers to a particle with a size, in at least one dimension, between about 10 nm to about 1000 nm; and may also include a nanoemulsion.

"NSAID nanosphere" as used herein refers to a nanosphere comprising molecules of Formula I.

"Antioxidant and NSAID nanosphere" and "NSAID nanosphere and Antioxidant nanosphere" as used herein refer to a nanosphere comprising molecules of Formula II and/or Formula III.

"Antioxidant nanosphere" as used herein refers to a nanosphere comprising molecules of Formula IV and/or V.

"NSAID/Antioxidant nanosphere combination" and "Antioxidant/NSAID nanosphere combination" as used herein refer to a nanosphere comprising molecules selected from Formula I, II or III, and molecules selected from Formula IV or V.

"NSAID nanosphere/Antioxidant nanosphere composition" and "Antioxidant nanosphere/NSAID nanosphere composition" as used herein refer to a composition comprising Antioxidant nanospheres in combination with NSAID nanospheres or Antioxidant and NSAID nanospheres.

"Nanoprodrug" is used interchangeably with "nanosphere" throughout the application.

Novel stimuli-responsive nanoprodrugs of NSAIDs were prepared by spontaneous emulsification of hydrophobic derivatives of NSAIDs. The inventors demonstrated their antioxidant activity, oxidant responsiveness and enzymatic activation. Despite the highly hydrophobic nature of the derivatives, NSAIDs were readily hydrolyzed enzymatically from the nanoprodrugs, and the hydrolysis was accelerated when the nanoprodrugs were destabilized upon ROS scavenging. The unique interaction between the oxidative destabilization and enzyme reactivity characterizes this novel family of ROS-sensitive anti-inflammatory nanoprodrugs. The nanoprodrugs may be used as anti-inflammatory and antioxidant drug delivery vehicles. Whenever the drug combination is favorable to the treatment of diseases, the antioxidant and anti-inflammatory properties of the nanoprodrugs may increase the therapeutic effect of the delivered drugs and reduce ROS-related adverse effects. Notably, the design and synthesis of water-insoluble hydrophobic prodrugs and their preparation into nanoprodrugs may create a new paradigm in the prodrug strategy.

NSAID Derivatives and Nanospheres

Various embodiments of the present invention provide for NSAID nanospheres comprising a hydrophobic derivative of an NSAID ("NSAID derivative"). In one embodiment, the NSAID nanospheres of the present invention are capable of releasing the NSAID derivatives during a prolonged period of time, and thus reduce adverse gastrointestinal side effects caused by NSAIDs.

The NSAID nanospheres comprise derivatives of NSAIDs ("NSAID derivative"). Hydrophobic NSAID derivatives of the present invention may be represented by Formula I:

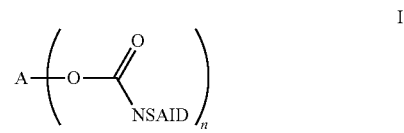

wherein the A is selected from the group consisting of branched and unbranched alkyl, branched and unbranched alkenyl, branched and unbranched alkynyl, heteroatom-containing branched and unbranched alkyl, heteroatom-containing branched and unbranched alkenyl, heteroatom-containing branched and unbranched alkynyl, aryl, cyclic aliphatic, cyclic aromatic, heterocyclic, and aromatic heterocyclic groups; and n is an integer of at least two, and in particular embodiments n may be an integer from 2-4. In various embodiments, A is a moiety that is formed by esterification of at least two free esterifiable hydroxyl groups on a polyol.

In various embodiments, polyols that are useful in the present invention include commercially available diols as follows:

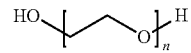

wherein n is an integer between 1 and 6.

wherein n is an integer between 3 and 16.

In other embodiments, the polyols may be selected from the commercial available polyols as shown below:

TABLE 1

| Compound | Structure |
|---|---|
| 1 | HO~~~OH |
| 2 | HO~~~O~~~OH |

TABLE 1-continued

| Compound | Structure |
|---|---|
| 3 | HO~O~O~OH |
| 4 | HO~O~O~O~OH |
| 5 | HO(CH2)6OH |
| 6 | 1,4-Benzenedimethanol |
| 7 | 1,2-Bis(2-hydroxyethyl)-piperazine |
| 8 | Glycerol (HOCH2-CHOH-CH2OH) |
| 9 | Triethanolamine |
| 10 | Triisopropanolamine |
| 11 | Pentaerythritol |
| 12 | (HOCH2)3C-N(CH2CH2OH)2 |
| 13 | 2,3-butanediol |
| 14 | 1,2-butanediol |
| 15 | 1,3-butanediol (with methyl) |
| 16 | 2,4-pentanediol |
| 17 | 1,3-pentanediol (with OH) |
| 18 | neopentyl glycol |
| 19 | 1,2-pentanediol branched |
| 20 | 1,2-hexanediol |
| 21 | 2,5-hexanediol |
| 22 | 3-methyl-1,5-pentanediol |
| 23 | 1,5-hexanediol (2-OH) |
| 24 | 2-ethyl-1,3-hexanediol type |
| 25 | 2-ethyl-2-propyl-1,3-propanediol |
| 26 | 1,5,6-hexanetriol type |
| 27 | 1,2-octanediol |
| 28 | 1,2-decanediol type |

TABLE 1-continued

| Compound | Structure |
|---|---|
| 29 | HO-CH2-CH(OH)-(CH2)12-CH3 (1,2-diol with long alkyl chain) |
| 30 | HOCH2-C(CH3)(CH2OH)-CH2OH |
| 31 | HOCH2-C(CH2OH)2-H (tris(hydroxymethyl)methane) |
| 32 | HO-(CH2)3-CH(OH)-CH2OH |
| 33 | HOCH2-C(CH2OH)(C2H5)-CH2OH |
| 34 | HOCH2-CH(OH)-CH(OH)-CH2OH |
| 35 | HOCH2-CH(OH)-(CH2)4-CH(OH)-CH2OH |
| 36 | [HOCH2-C(C2H5)(CH2OH)-CH2-]2O |
| 37 | 1,1-bis(hydroxymethyl)cyclopropane |
| 38 | 1,2-cyclopentanediol |
| 39 | 1,3-cyclopentanediol |
| 40 | 1,2-cyclohexanediol |
| 41 | 1,3-cyclohexanediol |
| 42 | 1,4-Cyclohexanediol |
| 43 | 1,3,5-cyclohexanetriol |
| 44 | 1,2-bis(hydroxymethyl)cyclohexane |
| 45 | 1,4-bis(hydroxymethyl)cyclohexane |
| 46 | 1,2-cyclooctanediol |
| 47 | 1,5-cyclooctanediol |
| 48 | 1,3-benzenedimethanol |
| 49 | 1-phenyl-1,2-ethanediol |
| 50 | 1,2-benzenedimethanol |

TABLE 1-continued

| Compound | Structure |
|---|---|
| 51 | 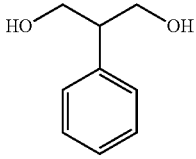 |
| 52 | 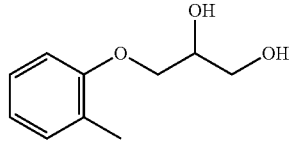 |
| 53 | 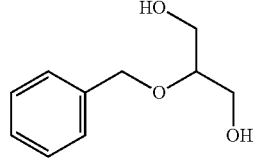 [SMILES: OCC(CO)OCc1ccccc1] |
| 54 | 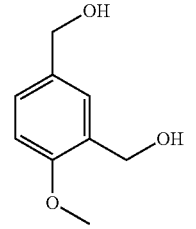 |
| 55 | 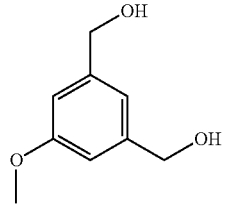 |
| 56 | 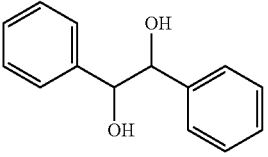 [SMILES: OC(c1ccccc1)C(O)c1ccccc1] |
| 57 | 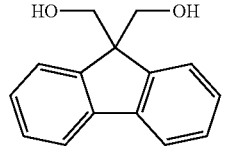 [SMILES: OCC1(CO)c2ccccc2-c2ccccc21] |
| 58 | 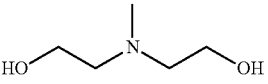 |
| 59 | 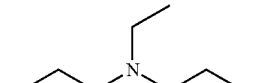 |
| 60 | 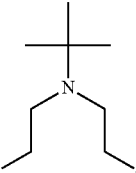 |
| 61 |  |
| 62 |  |
| 63 | 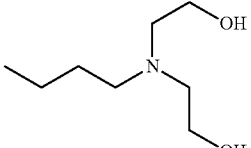 |
| 64 | 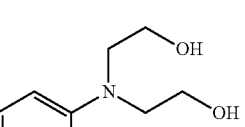 |
| 65 | 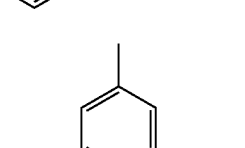 |

The NSAID may be a non-steroidal anti-inflammatory drug containing a carboxylic acid. NSAIDs are well known in the art and one of skill in the art will be able to readily choose an NSAID without undue experimentation. The carboxylic group of the NSAIDs is temporarily masked via hydrolysable bond, and may therefore act as a prodrug and reduce the side effect and also has advantage in the controlled and sustained release of the drugs.

Examples of NSAIDs include but are not limited to aspirin, ibuprofen, flurbiprofen, ketoprofen, fenoprofen, fenbufen, naproxen, indomethacin, diclofenac, ketorolac, tolmetin, flufenamic acid, mefenamic acid, tolfenamic acid, meclofenamic acid, niflumic acid, sulindac, and sulindac sulfide.

Aspirin

Ibuprofen

Naproxen

Indomethacin

Flufenamic acid

Sulindac

Sulindac sulfide

Flurbiprofen

Ketoprofen

Fenoprofen

Fenbufen

Diclofenac

Ketorolac

Tolmetin

-continued
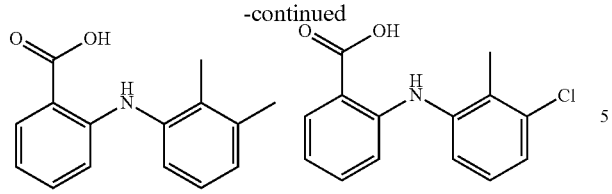
Mefenamic acid       Tolfenamic acid
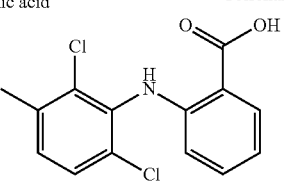
Meclofenac
-continued
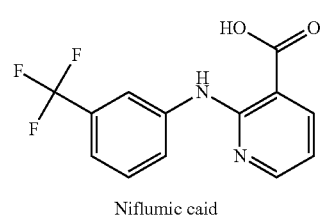
Niflumic caid
As such, examples of particularly useful hydrophobic derivatives of NSAIDs are represented by formulas as follows:
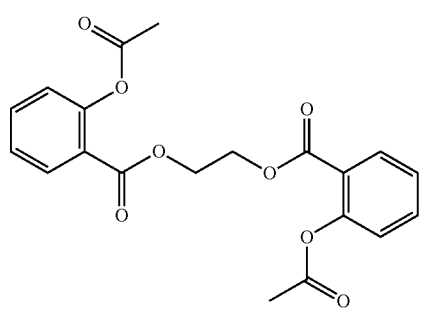
Ethylene glycol(aspirin)$_2$
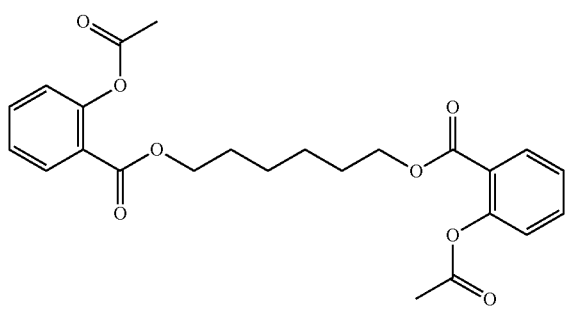
1,6-Hexanediol(aspirin)$_2$
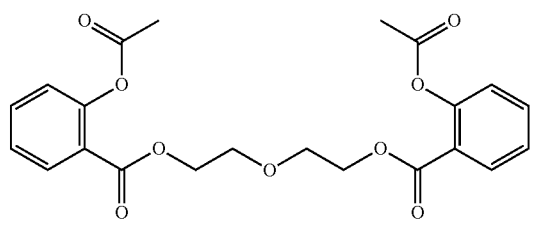
Diethylene glycol(aspirin)$_2$
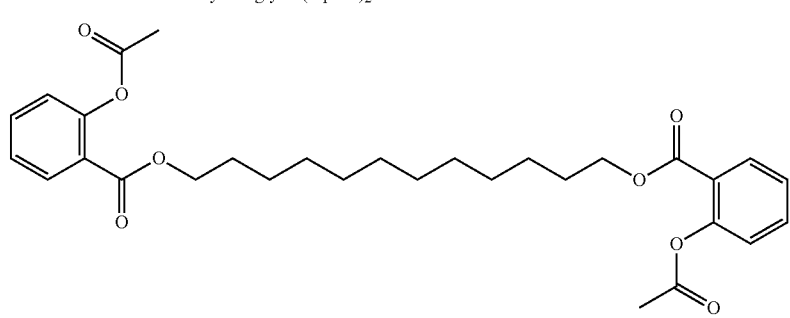
1,12-Dodecanediol(aspirin)$_2$
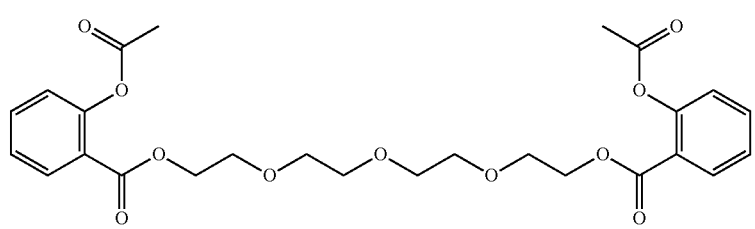
Tetraethylene glycol(aspirin)$_2$

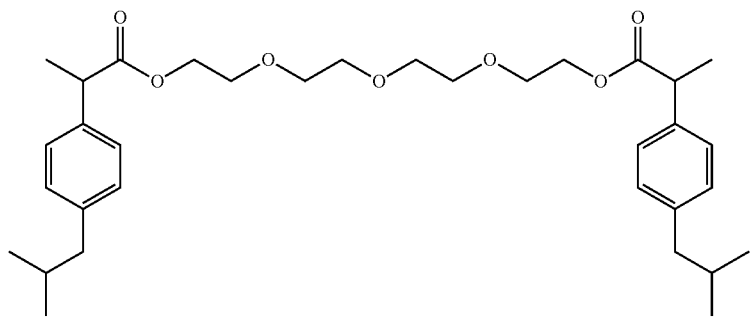
Tetraethylene glycol(ibuprofen)₂
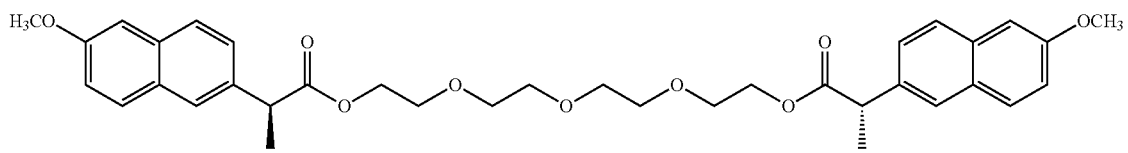
Tetraethylene glycol(naproxen)₂
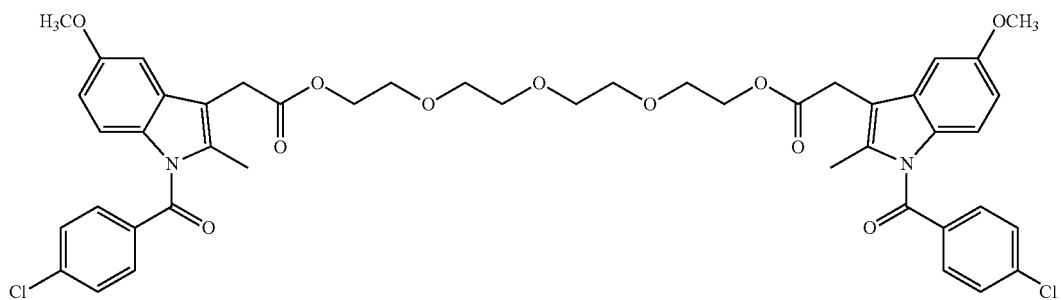
Tetraethylene glycol(indomethacin)₂
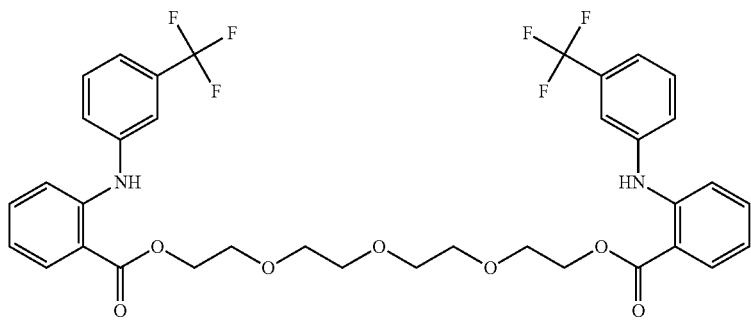
Tetraethylene glycol(flufenamic acid)₂
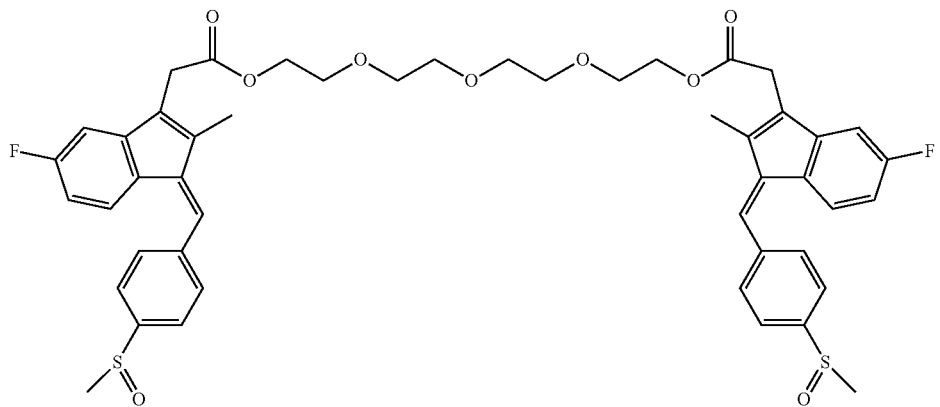
Tetraethylene glycol(sulindac)₂

-continued
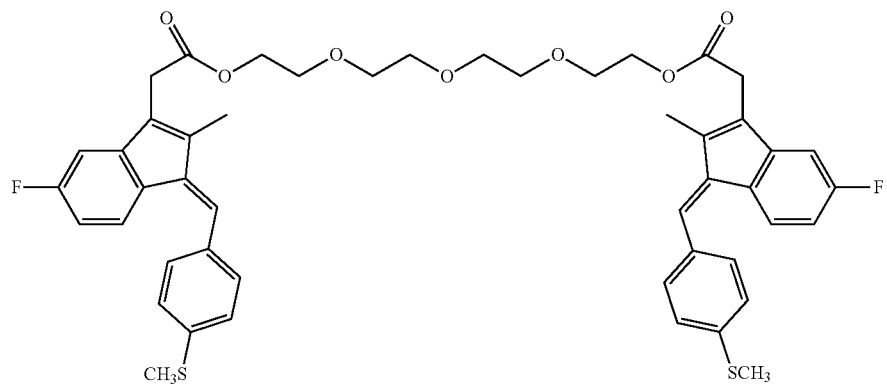
Tetraethylene glycol(sulindac sulfide)$_2$
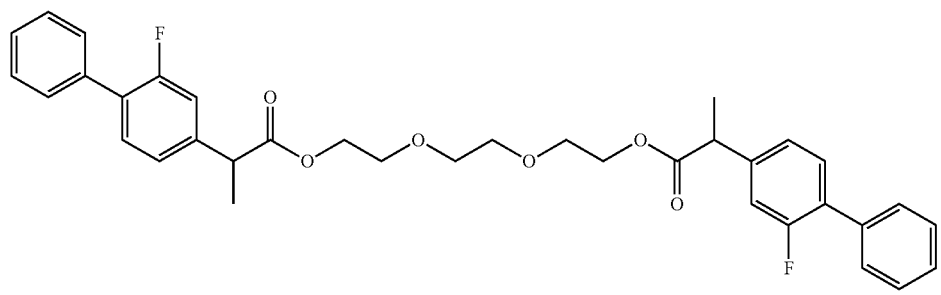
Tetraethylene glycol(flurbiprofen)$_2$
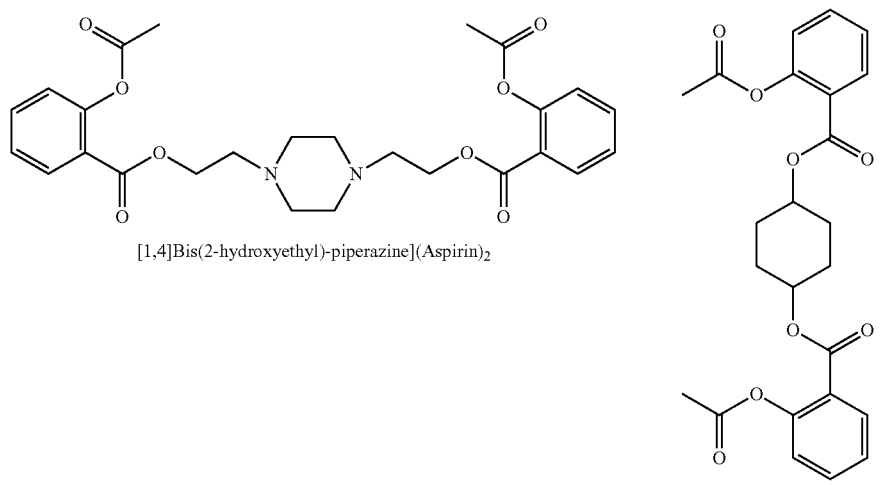
[1,4]Bis(2-hydroxyethyl)-piperazine](Aspirin)$_2$
1,4-Cyclohexanediol (Aspirin)$_2$

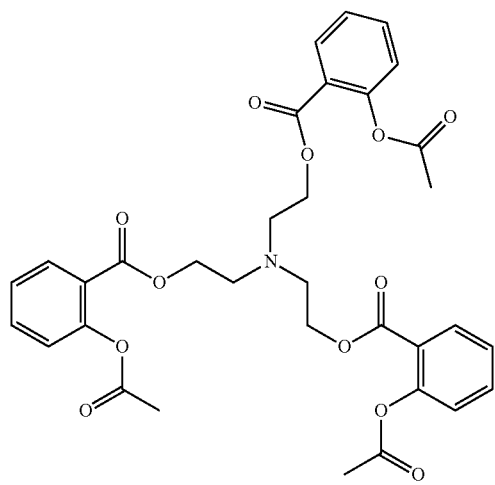

Triethanolamine (Aspirin)₂

A general scheme for the synthesis of the inventive multiple NSAID-containing hydrophobic compounds and preparation of the NSAID nanospheres are described in the ensuing examples. The synthetic procedures are both simple and versatile and lead to the synthesis of the inventive multiple NSAID-containing compounds varying in size and hydrophobicity. The inventive nanospheres showed sustained release of the free NSAIDs upon enzymatic hydrolysis by esterase.

Antioxidant and Anti-Inflammatory Derivatives and Nanospheres

Various embodiments of the present invention provide for antioxidant and NSAID nanospheres. In one embodiment, antioxidant and NSAID nanospheres of the present invention are capable of releasing the NSAIDs during a prolonged period of time.

Hydrophobic antioxidant and anti-inflammatory derivatives of an NSAID of the present invention may be represented by Formula II:

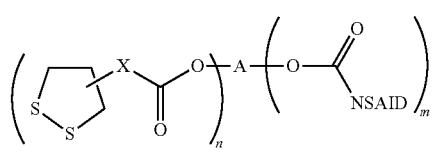

wherein X is selected from the group consisting of a substituted, unsubstituted, branched or unbranched chain of carbon atoms and may optionally contain a heteroatom; A is selected from the group consisting of branched and unbranched alkyl, branched and unbranched alkenyl, branched and unbranched alkynyl, heteroatom-containing branched and unbranched alkyl, heteroatom-containing branched and unbranched alkenyl, heteroatom-containing branched and unbranched alkynyl, aryl, cyclic aliphatic, cyclic aromatic, heterocyclic, and aromatic heterocyclic groups; n is an integer of at least one; and m is an integer of at least one. In one embodiment, X may be an unsubstituted, unbranched chain of 4 carbon atoms. In various embodiments, A is a moiety that is formed by esterification of at least two free esterifiable hydroxyl groups on a polyol. The polyol may be any polyol known in the art and as described above. The NSAID may be any NSAID known in the art and as described above In one embodiment, the [1,2]-dithiolane moieties are from α-lipoic acid ("ALA"), and thus, the antioxidant and NSAID derivatives of the present invention may be represented by Formula III:

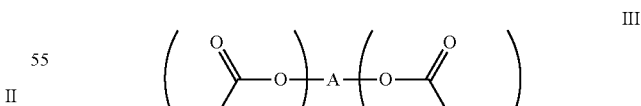

Accordingly, the antioxidant and NSAID nanospheres comprise a derivative of an NSAID and an α-lipoic acid.

Examples of particularly useful hydrophobic antioxidant and NSAID derivatives represented by formulas as follows:

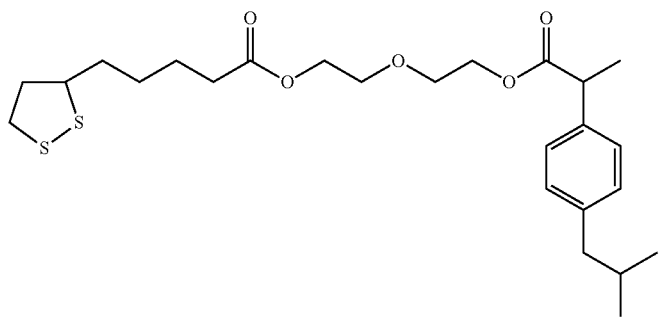
(α-Lipoic acid)-diethylene glycol(ibuprofen)
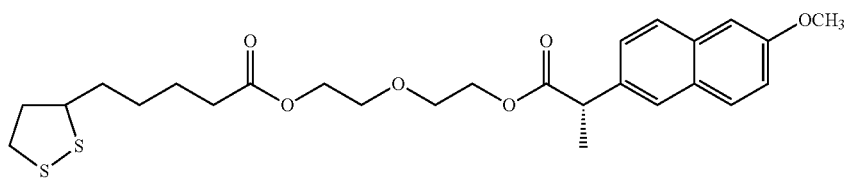
(α-Lipoic acid)-diethylene glycol(naproxen)
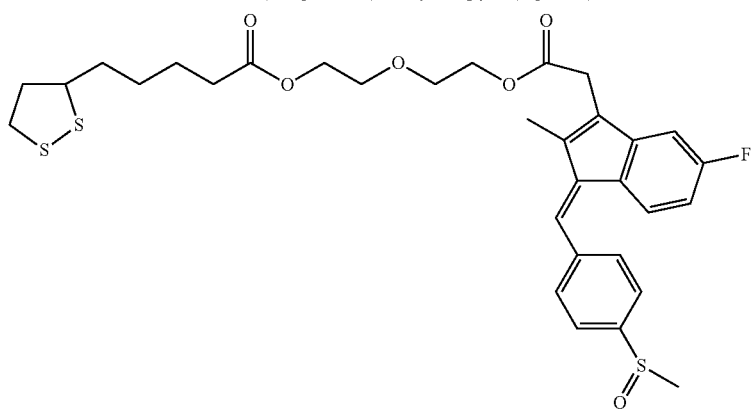
(α-Lipoic acid)-diethylene glycol(sulindac)
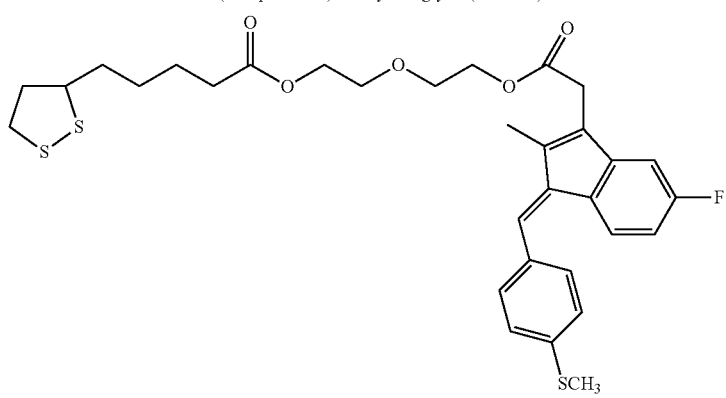
(α-Lipoic acid)-diethylene glycol(sulindac sulfide)
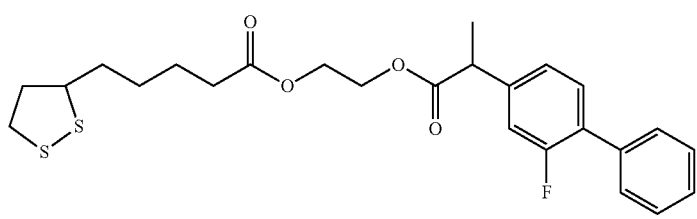
(α-Lipoic acid)-diethylene glycol(flurbiprofen)

-continued
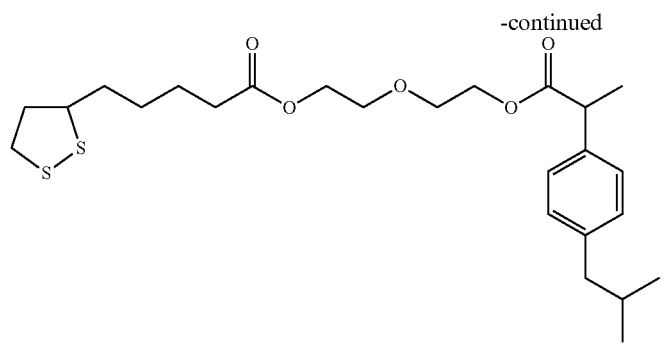
(α-Lipoic acid)-diethylene glycol(ibuprofen)
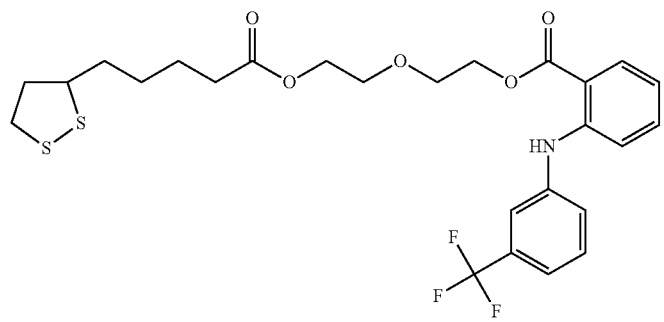
(α-Lipoic acid)-diethylene glycol(flufenamic acid)
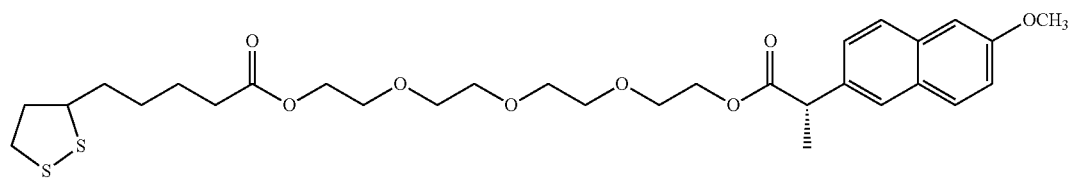
(α-Lipoic acid)-tetraethylene glycol(naproxen)
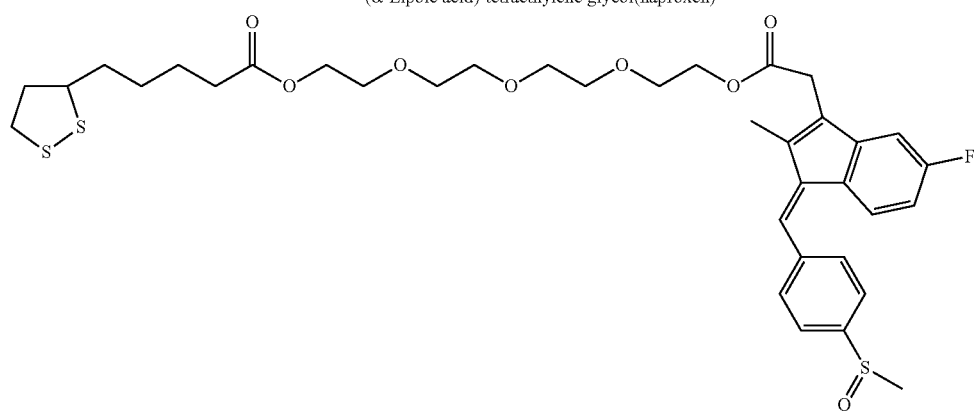
(α-Lipoic acid)-tetraethylene glycol(sulindac)

-continued

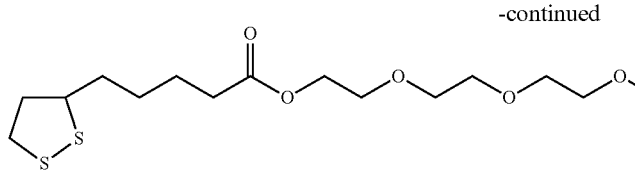
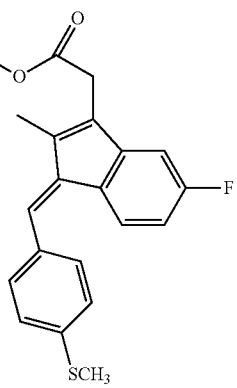

(α-Lipoic acid)-tetraethylene glycol(sulindac sulfide)

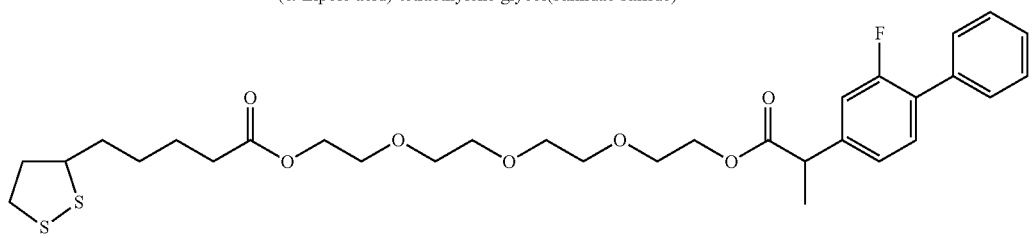

(α-Lipoic acid)-tetraethylene glycol(flurbiprofen)

A general scheme for the synthesis of the inventive α-lipoic acid and NSAID-containing hydrophobic compounds and preparation of the inventive antioxidant and NSAID nanospheres are described in the ensuing examples. The synthetic procedure is both simple and versatile and leads to the synthesis of the inventive α-lipoic acid and NSAID-containing hydrophobic compounds varying in size and hydrophobicity. The antioxidant activity of the inventive nanospheres has been demonstrated by HOCl scavenging assay.

Nanospheres Prepared from Mixture of the Inventive NSAID Derivatives and Polymers and/or Oils Various embodiments of the present invention also provide for a nanosphere comprising an NSAID derivative and a polymer and/or oily product. The NSAID derivatives may be ones as described above. Examples of polymers include, but not limited to, polyanhydrides, polyesters, polyorthoesters, polyesteramides, polyacetals, polyketals, polycarbonates, polyphosphoesters, polyphosphazene, polyvinylpyrrolidone, polydioxanones, poly(malic acid), poly(amino acids), polymers of N-2-(hydroxypropyl)methacrylamide (HPMA), polymers of N-isopropyl acrylamide (NIPAAm), polyglycolide, polylactide, copolymers of glycolide and lactide, and blends thereof. Examples of oily products include, but not limited to, vegetable oils, mineral oils, vitamins, esters of carboxylic acids and combinations thereof.

NSAID Nanospheres Combined with Antioxidant Nanospheres

Various embodiments of the present invention also provide for a composition comprising Antioxidant nanospheres in combination with NSAID nanospheres or Antioxidant and NSAID nanospheres ("NSAID nanosphere/antioxidant nanosphere composition"). The NSAID nanospheres and the Antioxidant and NSAID nanospheres may be ones as described above. The antioxidant nanospheres may be ones as described in International Application No. PCT/US08/88541, incorporated herein by references as though fully set forth.

Briefly, the antioxidant nanospheres comprise an antioxidant molecule represented by the Formula IV:

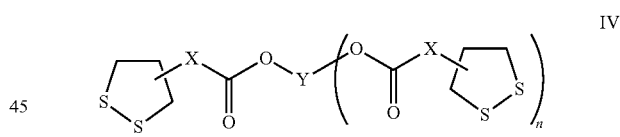

wherein X is selected from the group consisting of a substituted, unsubstituted, branched or unbranched chain of carbon atoms and may optionally contain a heteroatom; Y is selected from the group consisting of branched and unbranched alkyl, branched and unbranched alkenyl, branched and unbranched alkynyl, heteroatom-containing branched and unbranched alkyl, heteroatom-containing branched and unbranched alkenyl, heteroatom-containing branched and unbranched alkynyl, aryl, cyclic aliphatic, cyclic aromatic, heterocyclic, and aromatic heterocyclic groups; and n is an integer and is at least one. In various embodiments, Y is a moiety that is formed by esterification of at least two free esterifiable hydroxyl groups on a polyol. In one embodiment, the [1,2]-dithiolane moieties are from α-lipoic acid, and the antioxidants molecules are generally represented by the formula V:

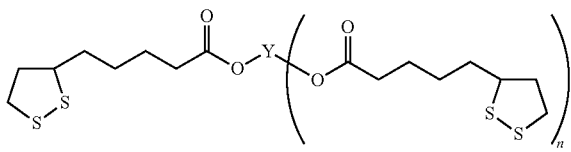

In this embodiment, at least two α-lipoic acids are linked to a polyol via ester bonds. The polyols may be ones known in the art and as described above.

NSAID/Antioxidant Nanosphere Combination

Various embodiments of the present invention also provide for a nanosphere comprising molecules selected from Formula I, II or III as described above, and molecules selected from Formula IV or V as described above ("NSAID/antioxidant nanosphere combination").

In various embodiments, the present invention provides pharmaceutical compositions including a pharmaceutically acceptable excipient along with a therapeutically effective amount of the NSAID nanospheres of the present invention, the antioxidant and NSAID nanospheres of the present invention, the NSAID nanosphere/antioxidant nanosphere composition of the present invention, or NSAID/antioxidant nanosphere combination of the present invention. "Pharmaceutically acceptable excipient" means an excipient that is useful in preparing a pharmaceutical composition that is generally safe, non-toxic, and desirable, and includes excipients that are acceptable for veterinary use as well as for human pharmaceutical use. Such excipients may be solid, liquid, semisolid, or, in the case of an aerosol composition, gaseous.

In various embodiments, the pharmaceutical compositions according to the invention may be formulated for delivery via any route of administration. "Route of administration" may refer to any administration pathway known in the art, including but not limited to aerosol, nasal, oral, transmucosal, transdermal or parenteral. "Parenteral" refers to a route of administration that is generally associated with injection, including intraorbital, infusion, intraarterial, intracapsular, intracardiac, intradermal, intramuscular, intraperitoneal, intrapulmonary, intraspinal, intrasternal, intrathecal, intrauterine, intravenous, subarachnoid, subcapsular, subcutaneous, transmucosal, or transtracheal. Via the parenteral route, the compositions may be in the form of solutions or suspensions for infusion or for injection, or as lyophilized powders.

The pharmaceutical compositions according to the invention can also contain any pharmaceutically acceptable carrier. "Pharmaceutically acceptable carrier" as used herein refers to a pharmaceutically acceptable material, composition, or vehicle that is involved in carrying or transporting a compound of interest from one tissue, organ, or portion of the body to another tissue, organ, or portion of the body. For example, the carrier may be a liquid or solid filler, diluent, excipient, solvent, or encapsulating material, or a combination thereof. Each component of the carrier must be "pharmaceutically acceptable" in that it must be compatible with the other ingredients of the formulation. It must also be suitable for use in contact with any tissues or organs with which it may come in contact, meaning that it must not carry a risk of toxicity, irritation, allergic response, immunogenicity, or any other complication that excessively outweighs its therapeutic benefits.

The pharmaceutical compositions according to the invention can also be encapsulated, tableted or prepared in an emulsion or syrup for oral administration. Pharmaceutically acceptable solid or liquid carriers may be added to enhance or stabilize the composition, or to facilitate preparation of the composition. Liquid carriers include syrup, peanut oil, olive oil, glycerin, saline, alcohols and water. Solid carriers include starch, lactose, calcium sulfate, dihydrate, terra alba, magnesium stearate or stearic acid, talc, pectin, acacia, agar or gelatin. The carrier may also include a sustained release material such as glyceryl monostearate or glyceryl distearate, alone or with a wax.

The pharmaceutical preparations are made following the conventional techniques of pharmacy involving milling, mixing, granulation, and compressing, when necessary, for tablet forms; or milling, mixing and filling for hard gelatin capsule forms. When a liquid carrier is used, the preparation will be in the form of a syrup, elixir, emulsion or an aqueous or non-aqueous suspension. Such a liquid formulation may be administered directly p.o. or filled into a soft gelatin capsule.

The pharmaceutical compositions according to the invention may be delivered in a therapeutically effective amount. The precise therapeutically effective amount is that amount of the composition that will yield the most effective results in terms of efficacy of treatment in a given subject. This amount will vary depending upon a variety of factors, including but not limited to the characteristics of the therapeutic compound (including activity, pharmacokinetics, pharmacodynamics, and bioavailability), the physiological condition of the subject (including age, sex, disease type and stage, general physical condition, responsiveness to a given dosage, and type of medication), the nature of the pharmaceutically acceptable carrier or carriers in the formulation, and the route of administration. One skilled in the clinical and pharmacological arts will be able to determine a therapeutically effective amount through routine experimentation, for instance, by monitoring a subject's response to administration of a compound and adjusting the dosage accordingly. For additional guidance, see Remington: The Science and Practice of Pharmacy (Gennaro ed. 20th edition, Williams & Wilkins PA, USA) (2000).

Typical dosages of an effective amount of the NSAID nanospheres of the present invention, the antioxidant and NSAID nanospheres of the present invention, the NSAID nanosphere/antioxidant nanosphere composition of the present invention, or NSAID/antioxidant nanosphere combination of the present invention can be in the ranges recommended by the manufacturer where known therapeutic compounds are used, and also as indicated to the skilled artisan by the in vitro responses or responses in animal models. Such dosages typically can be reduced by up to about one order of magnitude in concentration or amount without losing the relevant biological activity. Thus, the actual dosage will depend upon the judgment of the physician, the condition of the patient, and the effectiveness of the therapeutic method based, for example, on the in vitro responsiveness of the relevant primary cultured cells or histocultured tissue sample, such as biopsied malignant tumors, or the responses observed in the appropriate animal models, as previously described.

Methods of Using the Nanospheres

Additional embodiments of the present invention provide for methods of using the NSAID nanospheres of the present invention, the antioxidant and NSAID nanospheres of the present invention, the NSAID nanosphere/antioxidant nanosphere composition of the present invention, or NSAID/antioxidant nanosphere combination of the present invention. These nanospheres may be used for treating inflammation or diseases or disease conditions that are caused by or related to inflammation in subjects in need thereof. The method comprises providing a composition comprising the NSAID nanospheres of the present invention, the antioxidant and NSAID nanospheres of the present invention, the NSAID nanosphere/antioxidant nanosphere composition of the present invention, or NSAID/antioxidant nanosphere combination of the present invention, and administering a therapeutically effective amount of the composition to the subject in need thereof.

In one particular embodiment, the NSAID nanospheres of the present invention, the antioxidant and NSAID nanospheres of the present invention, the NSAID nanosphere/antioxidant nanosphere composition of the present invention, or NSAID/antioxidant nanosphere combination of the present invention are used to treat Alzheimer's disease in a subject in need thereof. The method comprises providing a composition comprising the NSAID nanospheres of the present invention, the antioxidant and NSAID nanospheres of the present invention, the NSAID nanosphere/antioxidant nanosphere composition of the present invention, or NSAID/antioxidant nanosphere combination of the present invention and administering a therapeutically effective amount of the composition to the subject.

In one particular embodiment, the NSAID nanospheres of the present invention, the antioxidant and NSAID nanospheres of the present invention, the NSAID nanosphere/antioxidant nanosphere composition of the present invention, or NSAID/antioxidant nanosphere combination of the present invention are used to treat a disorder of abnormal cell proliferation (e.g., cancer, tumors) in a subject in need thereof. The method comprises providing a composition comprising the NSAID nanospheres of the present invention, the antioxidant and NSAID nanospheres of the present invention, the NSAID nanosphere/antioxidant nanosphere composition of the present invention, or NSAID/antioxidant nanosphere combination of the present invention and administering a therapeutically effective amount of the composition to the subject.

In another embodiment, the NSAID nanospheres of the present invention, the antioxidant and NSAID nanospheres of the present invention, the NSAID nanosphere/antioxidant nanosphere composition of the present invention, or NSAID/antioxidant nanosphere combination of the present invention may be used as a carrier of a therapeutic agent. In one embodiment, the therapeutic agent is a chemotherapeutic agent that is useful for cancer treatment. Accordingly, the present invention provides for a composition comprising the NSAID nanospheres of the present invention, the antioxidant and NSAID nanospheres of the present invention, the NSAID nanosphere/antioxidant nanosphere composition of the present invention, or NSAID/antioxidant nanosphere combination of the present invention and a therapeutic agent.

In another embodiment, the NSAID nanospheres of the present invention, the antioxidant and NSAID nanospheres of the present invention, the NSAID nanosphere/antioxidant nanosphere composition of the present invention, or NSAID/antioxidant nanosphere combination of the present invention may also be used as pharmaceutical and/or drug delivery vehicles to deliver small molecules, peptides, oligonucleotides, polynucleotides, proteins, antigens, chemotherapeutics, antisense nucleic acid molecules and the like, to tissue, organ, cell, etc.

In another embodiment, the present invention provides for a method to enhance the cytotoxicity of an antineoplastic drug for treatment of a disorder of abnormal cell proliferation (e.g., cancer, tumors). The method comprises providing a composition comprising an amount of the NSAID nanospheres of the present invention, the antioxidant and NSAID nanospheres of the present invention, the NSAID nanosphere/antioxidant nanosphere composition of the present invention, or NSAID/antioxidant nanosphere combination of the present invention; and administering a therapeutically effective amount of the composition and the antineoplastic drug to a subject in need of the treatment. Antineoplastic drugs are known to one skilled in the art. Examples include but are not limited to paclitaxel, camptothecin and temozolomide.

Methods of Preparing the Nanospheres

In another embodiment, the present invention provides for a method of preparing NSAID nanospheres comprising an NSAID derivative of the present invention. The method comprises providing an NSAID derivative of formula I and processing the NSAID derivative in a spontaneous emulsification process.

In another embodiment, the present invention provides for a method of preparing the NSAID/antioxidant nanosphere combination of the present invention. The antioxidant nanosphere may be a molecule as described by International Application No. PCT/US08/88541, which is incorporated herein by reference in its entirety as though fully set forth (e.g., formulas IV and V). The method comprises providing an NSAID derivative of formula I and an antioxidant molecule of formula IV or V and processing the NSAID derivative and antioxidant molecule in a spontaneous emulsification process. In another embodiment the method comprises providing molecules of Formula II and/or Formula III and an antioxidant molecule of formula IV or V and processing the molecules of Formula II and/or Formula and antioxidant molecule in a spontaneous emulsification process In another embodiment, the present invention provides for a method of preparing the antioxidant and NSAID nanospheres. The method comprises providing a molecule of formula II or formula III and processing the molecule in a spontaneous emulsification process.

Kits

The present invention is also directed to kits to treat inflammation, a disease or disease condition caused by inflammation or related to inflammation, a disease or disease condition caused by or related to reactive oxygen species. The kit is an assemblage of materials or components, including at least one of the inventive compositions. Thus, in some embodiments the kit contains a composition including the NSAID nanospheres of the present invention, the antioxidant and NSAID nanospheres of the present invention, the NSAID nanosphere/antioxidant nanosphere composition of the present invention, or NSAID/antioxidant nanosphere combination of the present invention as described above.

The exact nature of the components configured in the inventive kit depends on its intended purpose. In one embodiment, the kit is configured particularly for the purpose of treating mammalian subjects. In another embodiment, the kit is configured particularly for the purpose of treating human subjects. In further embodiments, the kit is configured for veterinary applications, treating subjects such as, but not limited to, farm animals, domestic animals, and laboratory animals.

Instructions for use may be included in the kit. "Instructions for use" typically include a tangible expression describing the technique to be employed in using the components of the kit to effect a desired outcome, such as to treat inflammation, a disease or disease condition caused by or related to inflammation, a disease or disease condition cause by or related to reactive oxygen species, or to treat cancer. Optionally, the kit also contains other useful components, such as, diluents, buffers, pharmaceutically acceptable carriers, syringes, catheters, applicators, pipetting or measuring tools, bandaging materials or other useful paraphernalia as will be readily recognized by those of skill in the art.

The materials or components assembled in the kit can be provided to the practitioner stored in any convenient and suitable ways that preserve their operability and utility. For example the components can be in dissolved, dehydrated, or lyophilized form; they can be provided at room, refrigerated or frozen temperatures. The components are typically contained in suitable packaging material(s). As employed herein, the phrase "packaging material" refers to one or more physical structures used to house the contents of the kit, such as inventive compositions and the like. The packaging material is constructed by well known methods, preferably to provide a sterile, contaminant-free environment. The packaging materials employed in the kit are those customarily utilized in the treatment of inflammation, a disease or disease condition caused by inflammation or related to inflammation, a disease or disease condition caused by or related to reactive oxygen species. As used herein, the term "package" refers to a suitable solid matrix or material such as glass, plastic, paper, foil, and the like, capable of holding the individual kit components. Thus, for example, a package can be a glass vial used to contain suitable quantities of the NSAID nanospheres of the present invention, the antioxidant and NSAID nanospheres of the present invention, the NSAID nanosphere/antioxidant nanosphere composition of the present invention, or NSAID/antioxidant nanosphere combination of the present invention. The packaging material generally has an external label which indicates the contents and/or purpose of the kit and/or its components.

EXAMPLES

The following examples are provided to better illustrate the claimed invention and are not to be interpreted as limiting the scope of the invention. To the extent that specific materials are mentioned, it is merely for purposes of illustration and is not intended to limit the invention. One skilled in the art may develop equivalent means or reactants without the exercise of inventive capacity and without departing from the scope of the invention.

Example 1

General Procedures and Materials

Unless otherwise noted, solvents and chemicals were obtained as highest purity from Sigma-Aldrich Chemical Co. (St Louis, Mo., USA) and used without further preparation. Esterase (code E3019) was obtained from Sigma-Aldrich Chemical Co. Myeloperoxidase was obtained from Calbiochem (code 475911). Chromatographic purification of all newly synthesized compounds was performed using silica gel (60 Å, 200-400 mesh). The compounds were analyzed by thin layer chromatography (TLC): silicagel plates (Merck 60 F254); compounds were visualized by irritation by treatment with a solution of 1.5 g of $KMnO_4$, 10 g $K_2CO_3$, and 1.25 mL 10% NaOH in 200 mL of $H_2O$, followed by gentle heating. HPLC analysis was performed on Merck-Hitachi analytical LaChrom D-7000 HPLC/UV detector system with CAPCELL PAK, Type SG 120 (phenomenex) $C_{18}$ reversed phase column (250/4.6 mm, 5 µm). The derivatives of NSAIDs were visualized under UV light. $^1H$ and $^{13}C$ NMR spectra were conducted on a Varian 400 MHz spectrometer and chemical shifts (δ) were given in ppm relative to TMS. The spectra were recorded with the solvent $CDCl_3$ at room temperature.

Example 2

Synthesis of Bifunctional Derivatives of α-Lipoic Acid and NSAIDs

α-Lipoic acid (ALA, 10 mmol) and tetraethylene glycol (TEG, 30 mmol) in 50 ml of anhydrous dichloromethane (DCM) were reacted with 4-(dimethylamino)-pyridine (DMAP, 15 mmol) in the presence of a molecular sieve (Fluka, 3 Å, 10-20 mesh beads) for 10 min at room temperature. N-(3-Dimethylaminopropyl)-N-ethylcarbodiimide hydrochloride (EDCI, 10 mmol) was added portionwise over 10 min and the reaction mixture was stirred for 5 h at room temperature in the dark, filtered, and then concentrated under vacuum to reduce the volume. The product ALA-TEG-OH and dimeric byproduct ALA-TEG-ALA were purified using column chromatography by loading the concentrated reaction mixture on the column without prior preparation and characterized as described above. Mono-ALA derivatives of TEG (3.8 mmol) and NSAIDs (4.1 mmol, indomethacin: Ind, ibuprofen: Ibu, naproxen: Npx) in 20 ml of anhydrous DCM were reacted with DMAP (4.1 mmol) in the presence of molecular sieve for 10 min at room temperature. EDCI (4.1 mmol) was added portionwise over 10 min and the reaction mixture was stirred for 5 h at room temperature in the dark, filtered, and then concentrated under vacuum at room temperature. The products were purified using column chromatography and characterized as described above.

ALA-TEG-OH: The column chromatography on silica gel ($CHCl_3$:MeOH 50:1) gave the compound as a yellow oil (63%). TLC ($CHCl_3$:MeOH 50:0.5) $R_f$ 0.19; $^1H$ NMR (400 MHz, $CDCl_3$): δ=1.47 (m, 2×H, $H_a$), 1.68 (m, 4×H, $H_b$), 1.91 (m, 1×H, $H_c$), 2.36 (t, 2×H, $H_d$), 2.46 (m, 1×H, $H_e$), 2.61 (s, 1×H, —OH), 3.11 (m, 1×H, $H_f$), 3.18 (m, 1×H, $H_g$), 3.56 (m, 1×H, $H_h$), 3.61 (m, 2×H, $H_E$), 3.67 (s, 8×H, $H_A$), 3.71 (m, 4×H, $H_B$), 4.24 (m, 2×H, $H_D$). $^{13}C$ NMR (100 MHz, $CDCl_3$): δ=24.55, 28.67, 33.86, 34.54, 38.45, 40.19, 56.31, 61.6, 63.37, 69.11, 70.19, 70.43, 70.45, 70.56, 173.47.

ALA-TEG-ALA: The column chromatography on silica gel ($CHCl_3$:MeOH 90:1) gave the compound as a yellow oil. TLC ($CHCl_3$:MeOH 100:0.5) $R_f$ 0.12; $^1H$ NMR (400 MHz, $CDCl_3$): δ=1.47 (m, 4H, 2×Ha), 1.68 (m, 8H, 2×Hb), 1.91 (m, 2H, 2×Hc), 2.35 (t, J=7.5 Hz, 4H, 2×Hd), 2.46 (m, 2H, 2×He), 3.15 (m, 4H, 2×Hf+Hg), 3.57 (m, 2H, 2×Hh), 3.65 (s, 8H, O—$CH_2$—$CH_2$—O), 3.70 (t, J=4.8 Hz, 4H, 2×O—$CH_2$—$CH_2$—OCO), 4.23 (t, J=4.8 Hz, 4H, 2×CO—O—

CH$_2$—). $^{13}$C NMR (100 MHz, CDCl$_3$): δ=24.56, 28.71, 33.94, 34.56, 38.5, 40.22, 56.33, 63.44, 69.16, 70.56, 173.36.

ALA-TEG-Ind: The column chromatography on silica gel (CHCl$_3$:MeOH 100:0.5) gave the compound as a yellow oil (73%). TLC (CHCl$_3$:MeOH 50:0.5) R$_f$ 0.33; $^1$H NMR (400 MHz, CDCl$_3$): δ=1.48 (m, 2×H, H$_a$), 1.69 (m, 4×H, H$_b$), 1.92 (m, 1×H, H$_c$), 2.33-2.43 (m, 5×H, H$_8$+H$_d$), 2.47 (m, 1×H, H$_e$), 3.15 (m, 2×H, H$_f$+H$_g$), 3.54-3.75 (m, 15×H, H$_7$+H$_A$+H$_B$+H$_h$), 3.86 (s, 3×H, H$_6$), 4.27 (m, 4×H, H$_D$+H$_E$), 6.68 (q, 1×H, H$_5$), 6.95 (d, 1×H, H$_4$), 6.99 (d, 1×H, H$_3$), 7.49 (m, 2×H, H$_2$), 7.68 (m, 2×H, H$_1$). $^{13}$C NMR (100 MHz, CDCl$_3$): δ=13.4, 24.6, 28.7, 30.2, 33.9, 34.6, 38.5, 40.2, 55.71, 56.3, 63.4, 64.1, 69.1, 69.16, 70.53, 70.58, 101.39, 111.59, 112.50, 114.92, 129.12, 130.65, 130.78, 131.18, 133.91, 135.98, 139.20, 156.03, 168.24, 170.77, 173.41.

ALA-TEG-Ibu: The column chromatography on silica gel (CHCl$_3$:MeOH 100:0.5) gave the compound as a yellow oil (69%). TLC (CHCl$_3$:MeOH 50:0.5) R$_f$ 0.37; $^1$H NMR (400 MHz, CDCl$_3$): δ=0.86 (d, 6×H, H$_7$), 1.37-1.48 (m, 5×H, H$_6$+H$_a$), 1.64 (m, 4×H, H$_b$), 1.85-1.95 (m, 2×H, H$_5$+H$_c$), 2.32 (t, 2×H, H$_d$), 2.38-2.45 (m, 3×H, H$_4$+H$_e$), 3.04-3.18 (m, 2×H, H$_g$+H$_f$) 3.50-3.73 (m, 14×H, H$_3$+H$_A$+H$_B$+H$_h$), 4.20 (m, 4×H, H$_D$+H$_E$), 7.05 (d, 2×H, H$_2$), 7.18 (d, 2×H, H$_1$). $^{13}$C NMR (100 MHz, CDCl$_3$): δ=18.59, 22.41, 24.6, 28.71, 30.16, 33.91, 34.58, 38.47, 40.20, 44.98, 45.01, 56.31, 63.43, 63.85, 69.05, 69.16, 70.54, 70.59, 127.18, 129.27, 137.67, 140.44, 173.38, 174.62.

ALA-TEG-Npx: The column chromatography on silica gel (CHCl$_3$:MeOH 100:0.5) gave the compound as a yellow oil (65%). TLC (CHCl$_3$:MeOH 50:0.5) R$_f$ 0.33; $^1$H NMR (400 MHz, CDCl$_3$): δ=1.44 (m, 2×H, H$_a$), 1.54-1.71 (m, 7×H, H$_5$+H$_b$), 1.88 (m, 1×H, H$_c$), 2.33 (t, 2×H, H$_d$), 2.43 (m, 1×H, H$_e$), 3.05-3.19 (m, 2×H, H$_f$+H$_g$), 3.39-3.67 (m, 13×H, H$_4$+H$_B$+H$_h$), 3.88 (m, 4×H, H$_4$), 4.21 (m, 4×H, H$_D$+H$_E$), 7.12 (m, 2×H, H$_3$), 7.40 (q, 1×H, H$_2$), 7.68 (m, 3×H, H$_1$). $^{13}$C NMR (100 MHz, CDCl$_3$): δ=18.57, 24.61, 28.73, 33.93, 34.57, 38.48, 40.12, 45.33, 55.32, 56.33, 63.44, 63.96, 69.03, 69.14, 70.53, 105.57, 118.97, 125.99, 126.28, 127.11, 128.91, 129.28, 133.68, 135.63, 157.63, 173.44, 174.59.

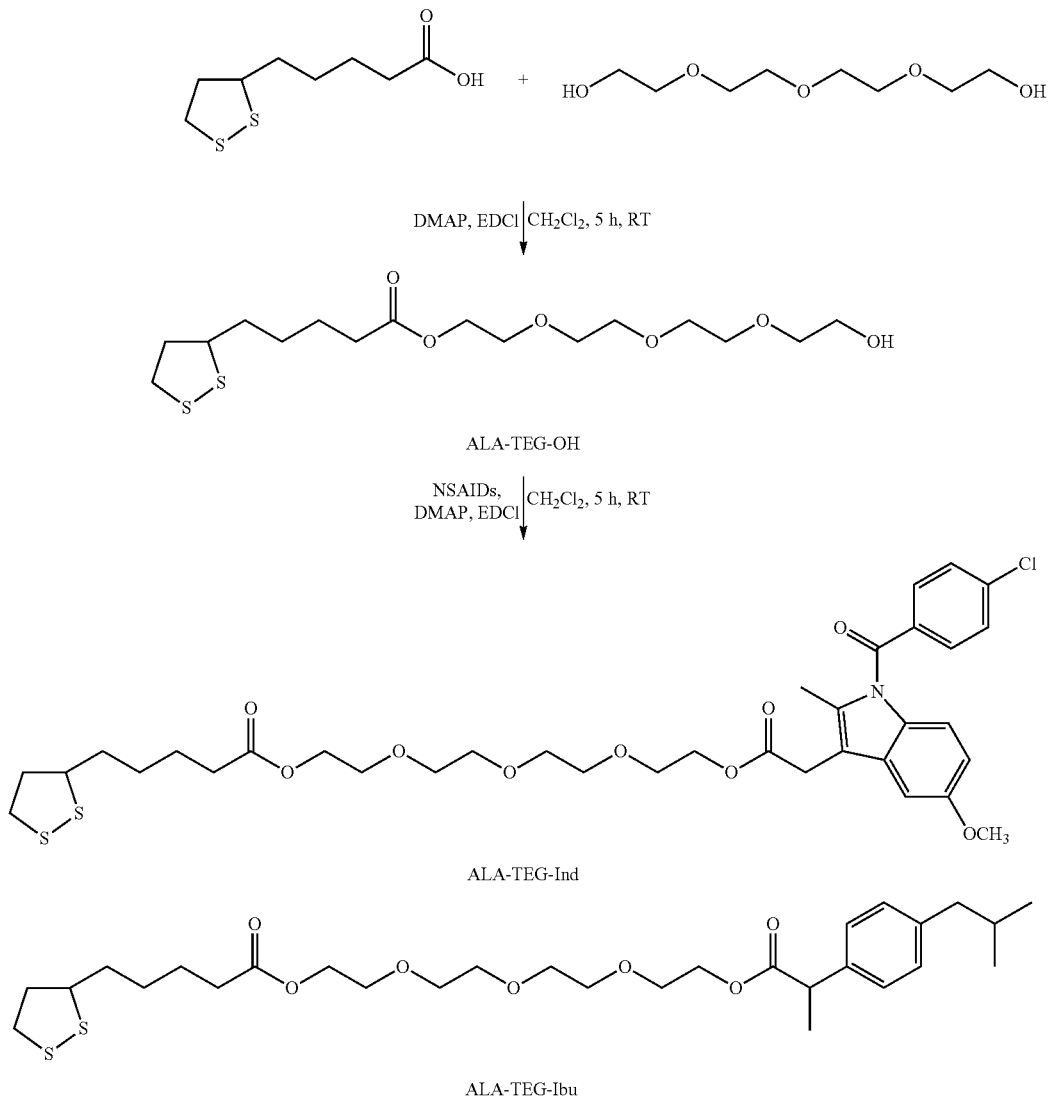

Scheme 1

-continued
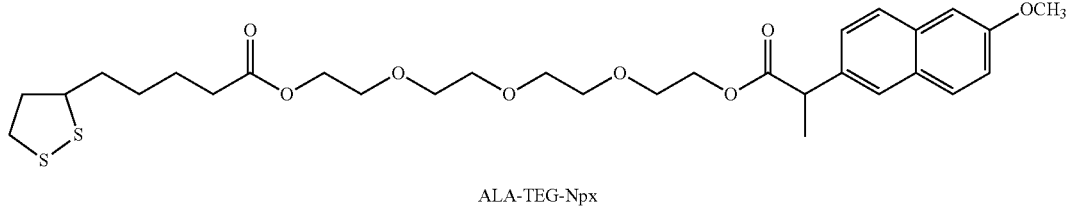
ALA-TEG-Npx
The same procedure, except that diethylene glycol was used instead of tetraethylene glycol, was used for the synthesis of the following compounds:
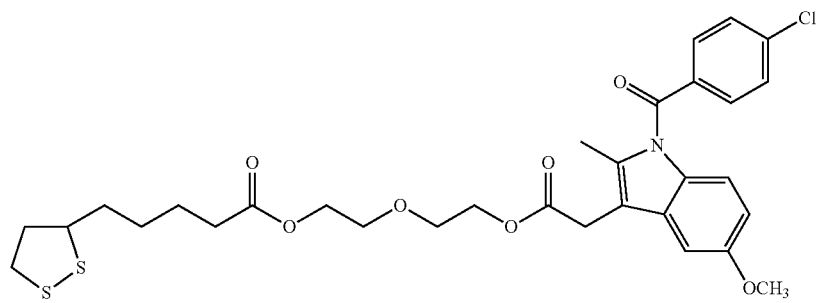
(α-Lipoic acid)-diethylene glycol(indomethacin)
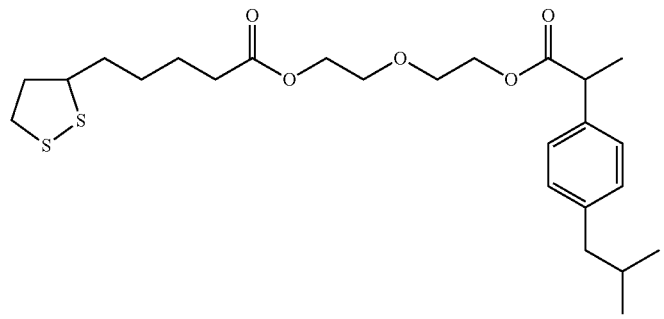
(α-Lipoic acid)-diethylene glycol(ibuprofen)
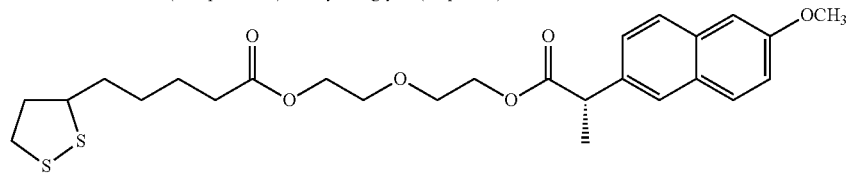
(α-Lipoic acid)-diethylene glycol(naproxen)
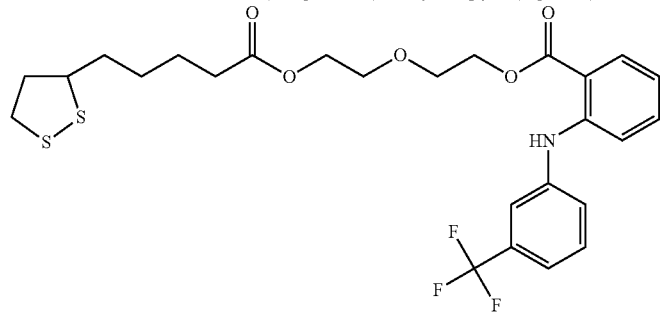
(α-Lipoic acid)-diethylene glycol(flufenamic acid)

Example 3

Synthesis of Dimeric Derivatives of NSAIDs

NSAIDs (6 mmol) and TEG (2.5 mmol) in 40 ml of anhydrous DCM were reacted with DMAP (6 mmol) in the presence of molecular sieve for 10 min at room temperature. EDCI (6 mmol) was added portionwise over 10 min and the reaction mixture was stirred for 5 h at room temperature in the dark, filtered, and then concentrated under vacuum. The products were purified (column chromatography, 100:0.5 $CH_3Cl$: MeOH) and characterized as described above.

$Ind_2TEG$: The column chromatography on silica gel ($CHCl_3$:MeOH 100:0.5) gave the compound as a yellow oil (78%). TLC ($CHCl_3$:MeOH 50:0.5) $R_f$ 0.25; $^1H$ NMR (400 MHz, $CDCl_3$): δ=2.35 (s, 6×H, $H_8$), 3.56 (m, 8×H, $H_A$), 3.64-3.70 (m, 8×H, $H_7+H_B$), 3.80 (s, 6×H, $H_6$), 4.25 (t, 4×H, $H_D+H_E$), 6.64 (q, 2×H, $H_5$), 6.86 (d, 2×H, $H_4$), 6.95 (d, 2×H, $H_3$), 7.43 (m, 4×H, $H_2$), 7.62 (m, 4×H, $H_1$). $^{13}C$ NMR (100 MHz, $CDCl_3$): δ=13.4, 30.19, 55.69, 64.13, 69.07, 70.52, 70.57, 101.4, 111.58, 112.51, 114.93, 129.11, 130.66, 130.79, 131.18, 133.93, 135.98, 139.18, 156.04, 168.22, 170.77.

$Ibu_2TEG$: The column chromatography on silica gel ($CHCl_3$:MeOH 100:0.5) gave the compound as a colorless oil (83%). TLC ($CHCl_3$:MeOH 50:0.5) $R_f$ 0.54; $^1H$ NMR (400 MHz, $CDCL_3$): δ=0.90 (d, 12×H, $H_7$), 1.49 (d, 6×H, $H_6$), 1.84 (m, 2×H, $H_5$), 2.44 (d, 4×H, $H_4$), 3.55 (m, 8×H, $H_A$), 3.63 (m, 4×H, $H_B$), 3.73 (q, 2×H, $H_3$), 4.22 (m, 4×H, $H_D+H_E$), 7.08 (m, 4×H, $H_2$), 7.21 (m, 4×H, $H_1$). $^{13}C$ NMR (100 MHz, $CDCl_3$): δ=18.60, 22.42, 30.19, 45.02, 45.04, 63.87, 69.08, 70.57, 70.61, 127.20, 129.29, 137.70, 140.48, 174.67.

$Npx_2TEG$: The column chromatography on silica gel ($CHCl_3$:MeOH 100:0.5) gave the compound as a colorless oil (75%). TLC ($CHCl_3$:MeOH 50:0.5) $R_f$ 0.46; $^1H$ NMR (400 MHz, $CDCl_3$): δ=1.58 (d, 6×H, $H_5$), 3.44 (m, 8×H, $H_A$), 3.60 (m, 4×H, $H_B$), 3.90 (m, 8×H, $H_4$), 4.22 (m, 4×H, $H_D+H_E$), 7.12 (m, 4×H, $H_3$), 7.41 (q, 2×H, $H_2$), 7.68 (m, 6×H, $H_1$). $^{13}C$ NMR (100 MHz, $CDCl_3$): δ=18.56, 45.33, 55.29, 63.95, 69.02, 70.44, 70.47, 105.56, 118.96, 125.96, 126.27, 127.11, 128.91, 129.27, 133.68, 135.62, 157.63, 174.60.

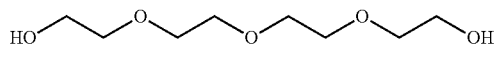

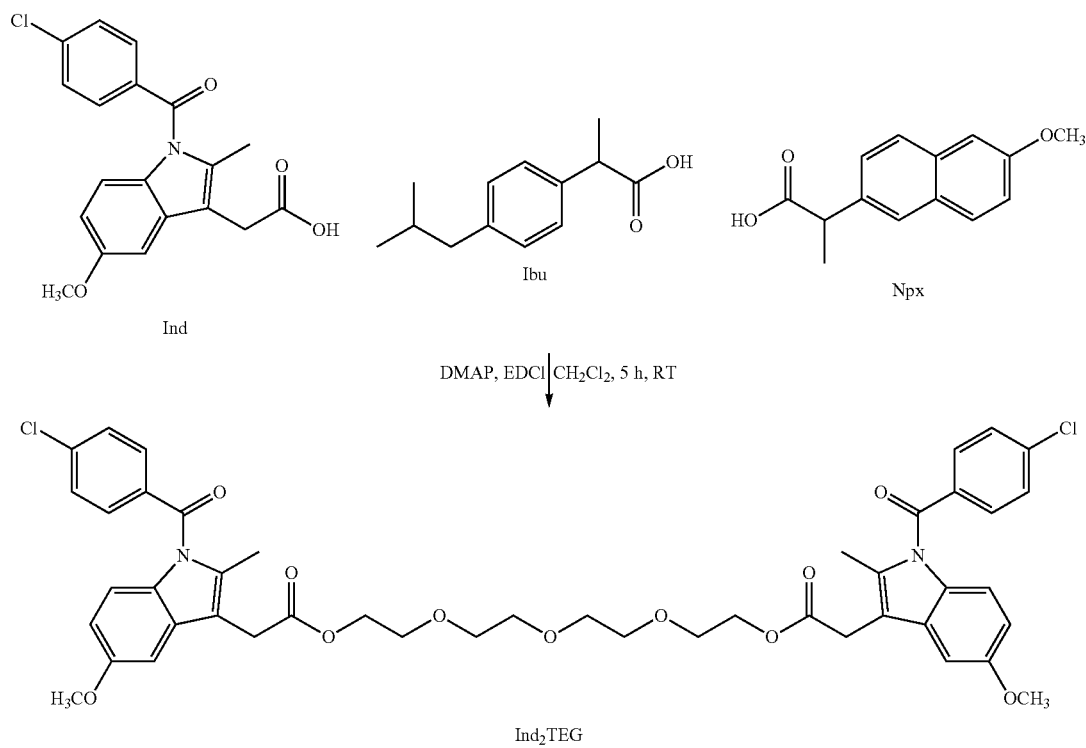

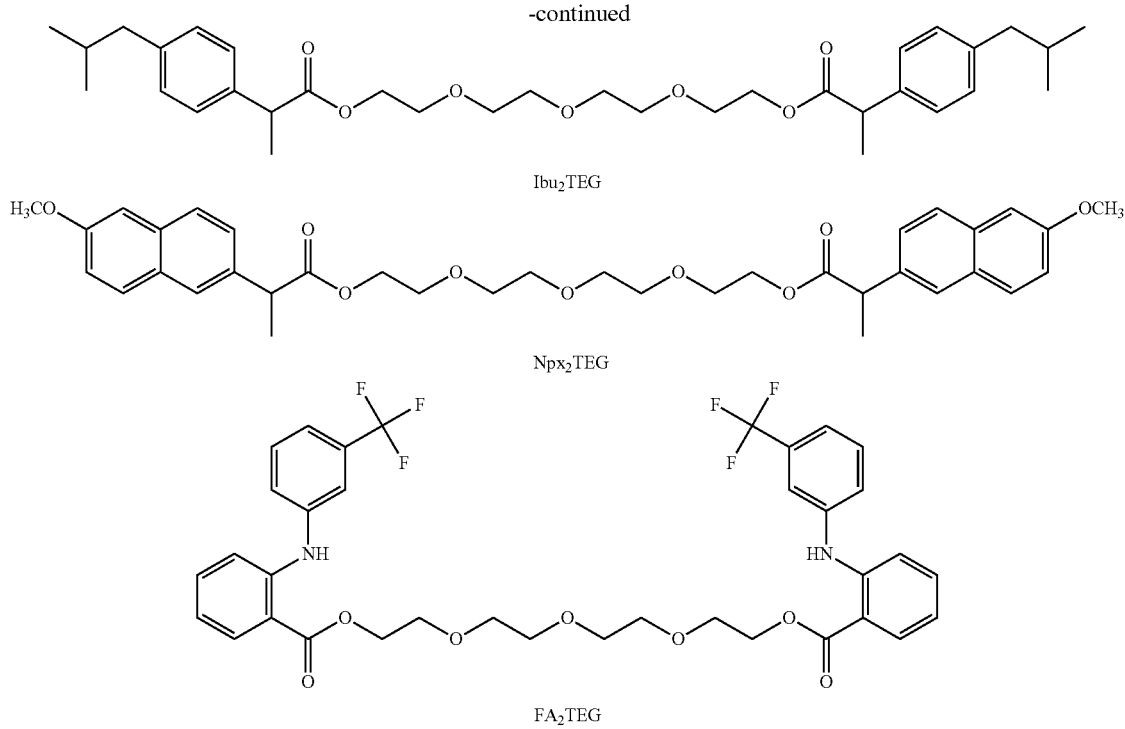

Ibu2TEG

Npx2TEG

FA2TEG

Example 4

High Performance Liquid Chromatography

RP-HPLC with UV detection was chosen as a simple, fast and effective method for quantification of many NSAID prodrugs and parent drugs (Bundgaard and Nielsen, 1988; Bonina et al., 1996; Redden et al., 1999; Mendes et al., 2002; Zhao et al., 2006). HPLC analysis was performed on a Merck-Hitachi analytical LaChrom D-7000 HPLC/UV detector system (Merck, Darmstadt, Germany) with a CAP-CELL PAK, Type SG 120 (phenomenex, Torrance, Calif., USA) $C_{18}$ reversed phase column (250/4.6 mm, 5 µm). The composition of the mobile phase (acetonitrile/water mixture containing 0.1% (v/v) trifluoroacetic acid) was adjusted for prodrugs and NSAIDs in order to provide an appropriate retention time and separation.

Linearity of the calibration curves was tested in the range of 6.25-2000 µg/ml for Ibu2TEG, Npx2TEG, Ind2TEG and ALA-TEG-Ind, 12.5-2000 µg/ml for ALA-TEG-Npx and 25-2000 µg/ml for ALA-TEG-Ibu with good linear relationships ($r^2 > 0.99$). Within this concentration range the amount of the prodrugs could be determined reproducibly.

Example 5

Determination of Partition Coefficients

Partition coefficients of the NSAID derivatives were studied using the shake flask method (Hansch and Elkins, 1971). Briefly, a known amount of NSAID derivatives (2 mg) was partitioned between water-saturated n-octanol (2 ml) and n-octane-saturated water (2 ml) and the mixture was stirred continuously with a magnetic bar for 24 h at room temperature. Following separation of the two phases, concentrations of the NSAID derivatives in the n-octane and water phase were analyzed using RP-HPLC (Section 2.4). The separation was performed under isocratic condition with an 80/20 mixture of acetonitrile/water (0.1% TFA, v/v) at a flow rate of 1 ml/min. The detection was carried out at 220 nm for Ibu-TEG-Ibu, at 254 nm for Npx-TEG-Npx and ALA-TEG-Ibu and at 330 nm for Ind2TEG, ALA-TEG-Npx and ALA-TEG-Ind.

Example 6

Spontaneous Emulsification

Nanoprodrugs were prepared according to the method using spontaneous emulsification (Bouchemal et al., 2004b). Briefly, 25 mg of the compounds were dissolved in acetone (5 ml) containing polysorbate 80 (0.1% w/v). The organic solution was poured under moderate stirring on a magnetic plate into an aqueous phase prepared by dissolving 25 mg of Pluronic F68 in 10 ml distilled water (0.25% w/v). Following 15 min of magnetic stirring, the acetone was removed under reduced pressure at room temperature. The suspensions were filtered through 0.8 µm hydrophilic syringe filter (Corning, Part No. 431221, Fisher Scientific Co., Pittsburgh, Pa., USA) and stored at 4° C.

Example 7

Size Measurements

The hydrodynamic size measurement and size distribution of the nanoprodrugs were performed by the dynamic light scattering (DLS) using a Coulter N4-Plus Submicron Particle Sizer (Coulter Corporation, Miami, Fla., USA). The nanoprodrugs were diluted in deionized water and the analysis was performed at a scattering angle of 90° and at a temperature of 25° C. Three separate preparations were analyzed for each nanoprodrug. For each preparation mean diameter and mean polydispersity index (P.I.) of three determinations were calculated. The mean diameter±standard deviation (S.D.) and P.I.±S.D. were calculated from the three mean diameters and mean P.I.'s of the three separate preparations.

TABLE 2A

Size and polydispersity index (P.I.) of the nanoprodrugs (n = 3, ±S.D.)

| NSAIDs derivatives | Size (nm) | P.I. |
|---|---|---|
| ALA-TEG-Ind | 253 ± 25 | 0.09 ± 0.05 |
| ALA-TEG-Ibu | 251 ± 13 | 0.10 ± 0.03 |
| ALA-TEG-Npx | 298 ± 6 | 0.05 ± 0.01 |
| Ind$_2$TEG | 159 ± 10 | 0.06 ± 0.03 |
| Ibu$_2$TEG | 186 ± 11 | 0.13 ± 0.02 |
| Npx$_2$TEG | 259 ± 9 | 0.06 ± 0.02 |

TABLE 2B

Hydrodynamic Size and Polydispersity Index (P.I.) of additional Nanospheres

| ALA-containing NSAID compounds | Size (nm) | P.I. |
|---|---|---|
| (α-Lipoic acid)-diethylene glycol(indomethacin) ALA-DEG-IND | 187 ± 54 | 0.13 |
| (α-Lipoic acid)-diethylene glycol(ibuprofen) ALA-DEG-Ibu | 210 ± 53 | 0.09 |
| (α-Lipoic acid)-diethylene glycol(naproxen) ALA-DEG-Npx | 274 ± 56 | 0.05 |
| (α-Lipoic acid)-tetraethylene glycol(flufenamic acid) ALA-TEG-FA | 149 ± 36 | 0.08 |

TABLE 2C

Size and Polydispersity Index (P.I.) of another NSAID nanosphere

| NSAID-containing hydrophobic compounds | Size (nm) | P.I. |
|---|---|---|
| Tetraethylene glycol(flufenamic acid)$_2$ (FA)$_2$TEG | 118 ± 32 | 0.11 |

Example 8

Stability of Nanoprodrugs in Simulated Gastric Fluid and Simulated Intestinal Fluid The stability of the nanoprodrugs was assessed in simulated gastric fluid (SGF, pH 1.2) and simulated intestinal fluid (SIF, pH 6.8). Briefly, 1 ml of freshly prepared nanoprodrugs was dispersed in 10 ml of freshly prepared SGF and SIF and incubated at 37° C. on a rotatory shaker for 3 days. SGF and SIF were prepared as described in Carafa et al. (2006): SGF was composed of 0.2% (w/v) sodium chloride, 0.32% pepsin (w/v) and 0.7% (w/v) hydrochloric acid. SIF was composed of 0.067 M mixed sodium and potassium phosphate buffer (Na$_2$HPO$_4$.7H$_2$O/KH$_2$PO$_4$—Sorensen's buffer). The stability of the nanoprodrugs was evaluated on the basis of the size and quantification of the intact prodrugs after 3 days. The recovery yield of the NSAIDs prodrugs was assessed by RP-HPLC as follows: the suspensions of nanoprodrugs were sedimented by centrifugation at 20,000×g for 10 min, the pellets were dissolved in acetonitrile and analyzed using RP-HPLC as described above. The recovery yield was calculated as follows:

$$\text{Recovery yield (\%)} = \frac{\text{Amount of prodrugs after incubation}}{\text{Amount of prodrugs before incubation}} \times 100$$

Example 9

Oxidative Destabilization of Nanoprodrugs

The nanoprodrugs were purified by centrifuging three times at 20,000×g for 10 min at 25° C. and resuspending each time in the same volume of deionized water. The purified nanoprodrugs were resuspended in phosphate buffered saline (PBS, pH 7.4) to give the final concentration of 250 μM NSAID derivatives. The concentration of HOCl in the diluted commercial sodium hypochlorite solution was determined spectrophotometrically ($\epsilon_{292}$=350 M$^{-1}$ cm$^{-1}$) (Morris, 1966). HOCl was added to the suspension of nanoprodrugs to give the final concentration of 25-1000 μM and the reduction in turbidity was measured immediately using ultraviolet/visible spectrometer (Bio-Rad SmartSpec™ 3000, Hercules, Calif., USA) at room temperature with a wavelength λ=500 nm.

Example 10

Assay for HOCl Scavenging

HOCl scavenging was monitored according to 5,5'-dithiobis(2-nitrobenzoic acid) (DTNB) assay as described (Ching et al., 1994). Briefly, 2-nitro-5-thiobenzoate (TNB) was formed by raising the pH of a 0.5 mM aqueous solution of DTNB to 10 and then readjusting it to 7.4 (Riddles et al., 1983). After 2 min of HOCl treatment, the nanoprodrugs were centrifuged at 20,000×g for 10 min. The supernatant (50 μl) was added to a reaction tube containing 950 μl of TNB solution (70 μM). After 5 min, the absorbance at 412 nm was measured. The absorbance of TNB after addition of 0-25 μM HOCl served as control.

Example 11

Enzymatic Destabilization of Nanoprodrugs

The nanoprodrugs were purified as described above and suspended in PBS (pH 7.4) to give the final concentration of 500 μM NSAID derivatives. Esterase (porcine liver, Sigma, code E3019) was added to the final concentration of 5 U/ml. For the nanoprodrugs from the three bifunctional prodrugs, ALA-TEG-Ibu, ALA-TEG-Npx and ALA-TEG-Ind, the reduction in turbidity was monitored using ultraviolet/visible spectrometer (Bio-Rad SmartSpec™ 3000) for 60 min at room temperature with a wavelength λ=500 nm and 1 min acquisition interval. For the nanoprodrugs from the three dimeric prodrugs, Ibu$_2$TEG, Npx$_2$TEG and Ind$_2$TEG, the samples were taken during the incubation for 12 h at room temperature with appropriate time interval and the reduction in turbidity was measured.

To determine the amount of enzymatically hydrolyzed NSAIDs, samples were centrifuged for 10 min at 20,000×g and the supernatants were analyzed by RP-HPLC using a C$_{18}$ reversed phase column (Section 2.5). The separation was performed under isocratic condition with a 60/40 mixture of acetonitrile/water (0.1% TFA, v/v) at a flow rate of 1 ml/min and the hydrolyzed NSAIDs were detected at 254 nm for indomethacin and naproxen and at 220 nm for ibuprofen.

The concentration of the NSAIDs was determined using calibration curves generated in the concentration range of 25-500 µM. Error bar represents ±S.D. calculated from triplicate determinations. The stability of the nanoprodrugs under the experimental conditions in the absence of esterase was evaluated as follows. The purified nanoprodrugs were suspended in PBS (pH 7.4) and incubated for 12 h at room temperature. The amount of the intact prodrugs was determined using RP-HPLC as described above.

Example 12

Sequence of Enzymatic Hydrolysis

Sequence of the enzymatic hydrolysis of ALA and NSAIDs from the nanoprodrugs was evaluated by measuring NSAIDs and other hydrolyzed species in the supernatant using RP-HPLC. The nanoprodrug containing 500 µM of ALA-TEG-Ibu, ALA-TEG-Npx or ALA-TEG-Ind (PBS, pH 7.4) was incubated in the presence of esterase (5 U/ml) at room temperature for 5 min and removed by centrifugation for 10 min at 20,000×g. The separation of the hydrolyzed species in the supernatant was performed under isocratic condition at a flow rate of 1 ml/min with a 60/40 mixture of acetonitrile/water (0.1% TFA, v/v) for ALA-TEG-Ibu, with a 50/50 mixture for ALA-TEG-Ind and a 35/65 mixture for ALA-TEG-Npx. NSAIDs were detected at 254 nm for indomethacin and naproxen and at 220 nm for ibuprofen. The supernatant was incubated for 30 min and analyzed as described above.

Example 13

Recovery of Intact Prodrugs from Oxidized Nanoprodrugs

The recovery yield of intact prodrugs was determined for oxidized and non-oxidized nanoprodrugs. The nanoprodrugs prepared from ALA-TEG-Ibu, ALA-TEG-Npx and ALA-TEG-Ind (250 µM in PBS, pH 7.4) were incubated in the presence of HOCl (500 µM) for 2 min. The nanoprodrugs were sedimented by centrifugation at 20,000×g for 10 min and the pellets were dissolved in acetonitrile and analyzed for intact prodrugs using RP-HPLC.

Example 14

Recovery of NSAIDs from Oxidized Nanoprodrugs

The recovery yield of NSAIDs was determined for oxidized and non-oxidized nanoprodrugs. The nanoprodrugs prepared from ALA-TEG-Ibu, ALA-TEG-Npx and ALA-TEG-Ind (250 µM in PBS, pH 7.4) were incubated in the presence and absence of HOCl (500 µM) for 2 min. Esterase (2 U/ml) was added and mixed by pipetting up and down. In order to determine the total amount of available NSAIDs from the oxidized and non-oxidized nanoprodrugs, the hydrolysis was carried out overnight at 37° C. The reaction mixture was centrifuged for 10 min at 20,000×g and the hydrolyzed NSAIDs in the supernatant were quantified using RP-HPLC. Error bar represents ±S.D. calculated from triplicate determinations.

Example 15

Effect of Nanoprodrug Oxidation on the Rate of Enzymatic Hydrolysis

In order to evaluate the effect of prodrug oxidation on the rate of enzymatic hydrolysis, the initial hydrolysis rate of NSAIDs from the oxidized and non-oxidized nanoprodrugs was determined. The nanoprodrugs prepared from ALA-TEG-Ibu, ALA-TEG-Npx and ALA-TEG-Ind (250 µM in PBS, pH 7.4) were incubated in the absence and presence of HOCl (500 µM) for 2 min. Esterase (2 U/ml) was added and mixed by pipetting up and down. The reaction mixture was centrifuged immediately after addition of esterase and the supernatant was quickly transferred into a new tube and incubated further to complete hydrolysis. The hydrolyzed NSAIDs in the supernatant were quantified using RP-HPLC as described above. Error bar represents ±S.D. calculated from triplicate determinations.

To evaluate the sequence of hydrolysis after oxidation, the nanoprodrugs were incubated in presence of HOCl (500 µM) for 2 min and esterase (2 U/ml) was added. The reaction mixture was mixed by pipetting up and down and immediately centrifuged for 10 min at 20,000×g. The supernatant was analyzed using RP-HPLC as described above.

Example 16

Statistical Analysis

The results were analyzed and expressed as mean±standard deviation (S.D.). Statistical analysis of the results was carried out using Student's t-test. For all tests, differences with a $p<0.05$ were considered to be significant.

Example 17

Synthesis and Characterization of Hydrophobic Derivatives of NSAIDs

Since the overproduction of reactive oxygen species (ROS) is associated with the inflammatory conditions and pathophysiology of many diseases (Finkei and Holbrook, 2000), NSAIDs prodrugs would be exceptionally valuable if they could scavenge ROS. Gastrointestinal ulceration is the major undesired side effect of almost all NSAIDs which is related mainly to the suppression of prostaglandin synthesis via inhibition of cyclooxygenase activity. In addition, it has been shown that the production of ROS is increased after NSAIDs treatment and the resulting oxidative damage has been also considered to be an important pathogenic component of gastrointestinal ulceration (Kusuhara et al., 1999; Basivireddy et al., 2004; Asensio et al., 2007). Meanwhile, it has been evidenced that the combination of antioxidant and anti-inflammatory activity could benefit the treatment of various inflammatory diseases by reducing ROS related side effects (Hassan et al., 1998; Kourounakis et al., 2000; Detsi et al., 2007; Ineu et al., 2008).

In order to combine the concept of prodrug, antioxidant, and stimuli-responsiveness, the inventors have made use of nanometer-sized prodrugs (nanoprodrugs). Design and synthesis of hydrophobic NSAIDs prodrug molecules that are capable of forming stable nanoprodrugs, scavenging ROS, and being degraded to the parent drugs, were central to obtaining oxidant-responsive nanoprodrugs. To achieve sensitivity to oxidation, a series of hydrophobic derivatives containing α-lipoic acid (ALA) and NSAIDs were designed.

Due to its potent antioxidant activity and beneficial effects on the prevention and treatment of oxidative stress-related diseases (Packer et al., 1995; Biewenga et al., 1997), ALA provides a rational foundation to the development of a new antioxidant and oxidation-responsive prodrug. The bifunctional compounds which combine ALA and NSAIDs into one molecule were synthesized using a two-step synthesis as described in Scheme 1. Tetraethylene glycol (TEG) was converted to a mono-ALA derivative (ALA-TEG-OH), which was followed by the esterification of NSAIDs. To reduce the formation of dimeric byproduct of ALA (ALA-TEG-ALA), a 3-fold molar excess of TEG was used. Due to its more hydrophobic nature, the dimeric byproduct was easily separated by column chromatography. The dimeric byproduct was identified as ALA-TEG-ALA using $^1$H and $^{13}$C NMR. The dimeric derivatives of NSAIDs consist of a core diol molecule TEG and two NSAID molecules (indomethacin: Ind, ibuprofen: Ibu, naproxen: Npx) which are coupled to the diol through esterification (Scheme 2). The structures were confirmed by $^1$H (FIGS. 1A-1G) and $^{13}$C NMR spectroscopy. The $^1$H NMR data indicate that the resulting spectra are essentially a composite of the NSAIDs and the core molecule. The integration values of the protons of α-lipoic acid and NSAIDs relative to those of the core molecule allow us to unambiguously identify the compounds.

The synthetic method presented here provides a simple and reproducible procedure to prepare large quantities of diverse hydrophobic compounds from NSAIDs and ALA. The purity of each synthesized compound was analyzed by thin layer chromatography (TLC) and RP-HPLC (Table 3).

TABLE 3

RP-HPLC retention time of the derivatives of NSAIDs

| NSAIDs derivatives | Retention time (min) | Detection (nm) |
|---|---|---|
| ALA-TEG-Ind | 7.84 | 330 |
| ALA-TEG-Ibu | 9.63 | 254 |
| ALA-TEG-Npx | 6.51 | 330 |
| Ind$_2$TEG | 10.3 | 330 |
| Ibu$_2$TEG | 17.2 | 220 |
| Npx$_2$TEG | 6.80 | 254 |

Example 18

Partition Coefficient Determinations

Partition coefficient determination using the shake-flask method was not successful for all the six NSAID derivatives, as they were too hydrophobic for distribution in the aqueous phase to be measured with HPLC.

Example 19

Nanoprodrug Formation Through Spontaneous Emulsification

The nanoprodrugs were prepared using the spontaneous emulsification mechanism developed for the formation of stable nanocapsules (Bouchemal et al., 2004a,b). The hydrophobic derivatives of NSAIDs in organic solvents spontaneously formed nanometer-sized prodrugs (nanoprodrugs) upon the addition of their organic solvents into an aqueous solution containing hydrophilic surfactants. The principle of nanocapsule formation by a spontaneous emulsification process is well described in publications (Chouinard et al., 1991; Bouchemal et al., 2004a,b). The size of nanocapsules depends on multiple factors, such as the nature and concentration of the compounds in organic solvents, the nature and concentration of surfactants in organic and aqueous phase, the ratio of organic solvent to water, and the rate of diffusion of organic phase into aqueous phase (Fessi et al., 1989; Chouinard et al., 1991; Bouchemal et al., 2004b).

In the experiments conducted, formulation parameters were kept constant as described above to evaluate the influence of the different NSAIDs derivatives on the size and stability of the nanoprodrugs. Six nanoprodrugs from the three bifunctional derivatives of ALA and NSAIDs and from the three dimeric NSAID derivatives were prepared. Upon addition of the solutions of the derivatives in acetone into the aqueous phase, nanoprodrugs formed spontaneously. The hydrodynamic size was within the range of 150 and 300 nm and found to be compound specific (Table 2A). The size of the nanoprodrugs was significantly larger when prepared from the naproxen derivatives (p<0.05). The size of the nanoprodrugs from the dimeric derivatives was significant smaller (p<0.01) than the size of the nanoprodrugs from the bifunctional derivatives, suggesting that a more compact steric arrangement of the symmetrical dimeric derivatives led to the formation of the smaller nanoprodrugs. It was also found that, except for the nanoprodrug from Ind$_2$TEG, the size decreased with increasing retention time in RP-HPLC (Table 3), suggesting a dependence of the size on the hydrophobicity of the prodrug molecules. The retention time in RP-HPLC may be useful to assess the hydrophobicity of the compounds (Hammers et al., 1982; Hafkenscheid and Tomlinson, 1984). Considering the combined results of the retention time in RP-HPLC and size measurement, it can be assumed that the size decreases with increasing hydrophobicity of the compounds, probably due to an even stronger hydrophobic interaction between the molecules.

Example 20

Stability of Nanoprodrugs in SGF and SIF

Figure 2A:
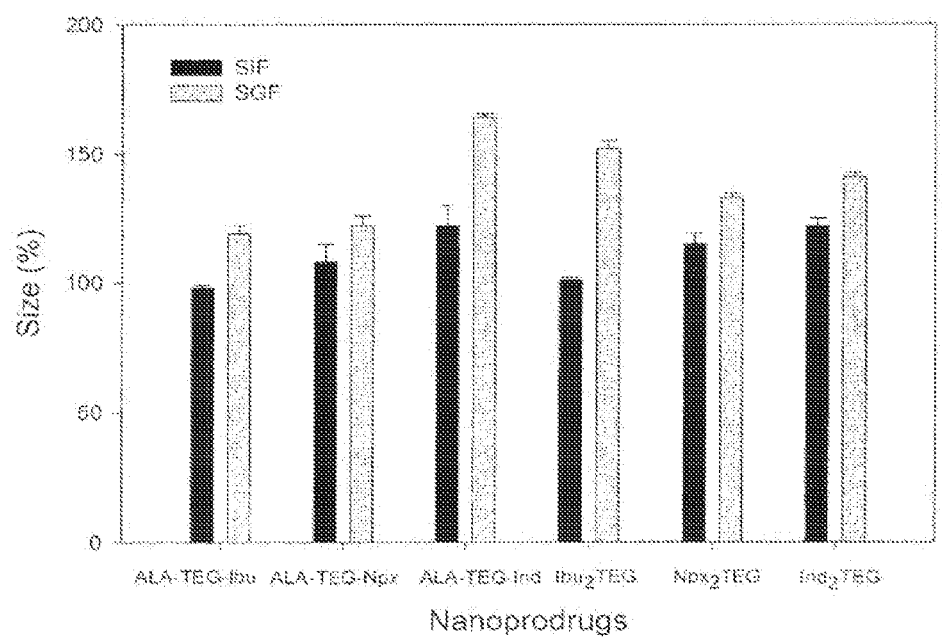
FIGS. 2A-2B depict the stability of nanoprodrugs in SIF pH 6.8 and SGF pH 1.2 in accordance with an embodiment of the present invention. The results are calculated as the percentage of size (FIG. 2A) and prodrugs (FIG. 2B) with 100% equal to the size and amount of prodrugs before incubation. The results are the mean±S.D. of three experiments.
Figure 2B:
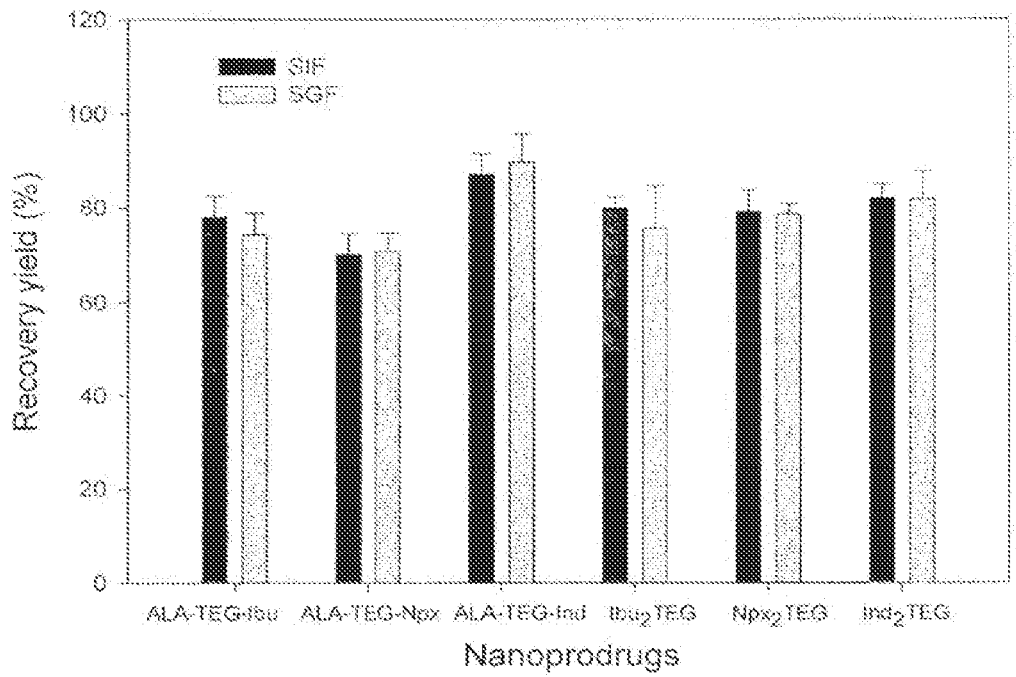

The stability of all the nanoprodrugs studied was examined in SGF and SIF. The samples were incubated at 37° C. on a rotatory shaker for three days. To evaluate the stability, the hydrodynamic size and amount of intact prodrugs were measured after three days. In SIF at pH 6.8, the size slightly increased except for the nanoprodrugs from ALA-TEG-Ibu and Ibu$_2$TEG (FIG. 2A). In SGF at pH 1.2, the increases were significant larger than those in SIF (p<0.05). Nevertheless, the size of the nanoprodrugs increased in both SIF and SGF, indicating that the nanoprodrugs tend to swell rather than disintegrate.

In order to maintain the antioxidant activity and oxidation responsiveness of the nanoprodrugs, the dithiolane ring moiety of the α-lipoic acid should remain intact. It has been reported that the reactivity and instability of the 1,2-dithiolane moiety of α-lipoic acid result in a considerable intermolecular polymerization (Wagner et al., 1956). Thus, the maintained functionality of the dithiolane ring moieties along with the physical stability of the nanoprodrugs is the basis for the development of the antioxidant and stimuli-responsive nanoprodrugs. The amount of the intact prodrug molecules was quantified after 3 days of incubation in SIF and SGF. As shown in FIG. 2B, 70-90% of the compounds remained intact after the incubation. The difference between SIF and SGF was not significant (p>0.05). In the supernatant, no prodrugs were detected, which is in agreement with the observed insolubility of the prodrugs in aqueous solution. Considering the results of the size measurement and chemical stability, it is concluded that the method of spontaneous emulsification produces nanoprodrugs that are stable in SIF and SGF. It is believed that the observed chemical and physical stability of the nanoprodrugs can be ascribed to the strong assembly of the hydrophobic prodrug molecules which reduces the interaction with water, consequently increasing the structural integrity of the nanoprodrugs and thus decreasing the chemical degradation of the prodrugs in the aqueous environment.

Example 21

Oxidative Destabilization of Nanoprodrugs

The antioxidant properties and oxidation-responsiveness of the nanoprodrugs are attributed to the dithiolane ring system of ALA. The ring system can scavenge a variety of ROS, which leads to the formation of thiosulfinate and thiosulfonate (Biewenga et al., 1994; Trujillo and Radi, 2002). Therefore, it was expected that the oxidation would make the ALA-containing NSAID prodrugs less hydrophobic, which would lead to the destabilization of the nanoprodrugs.

In this study, hypochlorous acid (HOCl) was used as the oxidant to elucidate the antioxidant properties and oxidative destabilization of the nanoprodrugs. In the presence of physiological concentration of chloride ions, $H_2O_2$ is efficiently halogenated by the inflammatory enzyme myeloperoxidase (MPO) to yield HOCl (Krasowska and Konat, 2004; Malle et al., 2007). $H_2O_2$ is not particularly toxic as it is not acutely reactive against many biologically important molecules, but the cytotoxicity was greatly enhanced by converting of up to 80% of the $H_2O_2$ generated by activated neutrophils into the highly reactive HOCl (Weiss et al., 1982; Foote et al., 1983; Babior, 2000; Hussien et al., 2002). HOCl is by far the most abundant oxidant generated by activated phagocyte cells and is a powerful oxidizing agent that can react with many biological molecules (Winterbourn, 2002; Krasowska and Konat, 2004; Messner et al., 2006; Spickett, 2007; Yap et al., 2007). It has been also reported that HOCl can be easily converted into a hydroxyl radical (.OH) by a reaction with superoxide radical ($O_2.^-$) and ferrous iron ($Fe^{2+}$) (Candeias et al., 1993).

To demonstrate the antioxidant properties and oxidative destabilization of the nanoprodrugs, the optical density of the nanoprodrug suspension (250 µM) was measured in the presence of HOCl (25-1000 µM) at 500 nm (OD). In the absence of HOCl, no changes in OD were observed during an incubation for 24 h (data not shown). In addition, the nanoprodrugs lacking ALA ($Ind_2TEG$, $Ibu_2TEG$, and $Npx_2TEG$) did not show any changes in OD (data not shown).

Figure 3A:
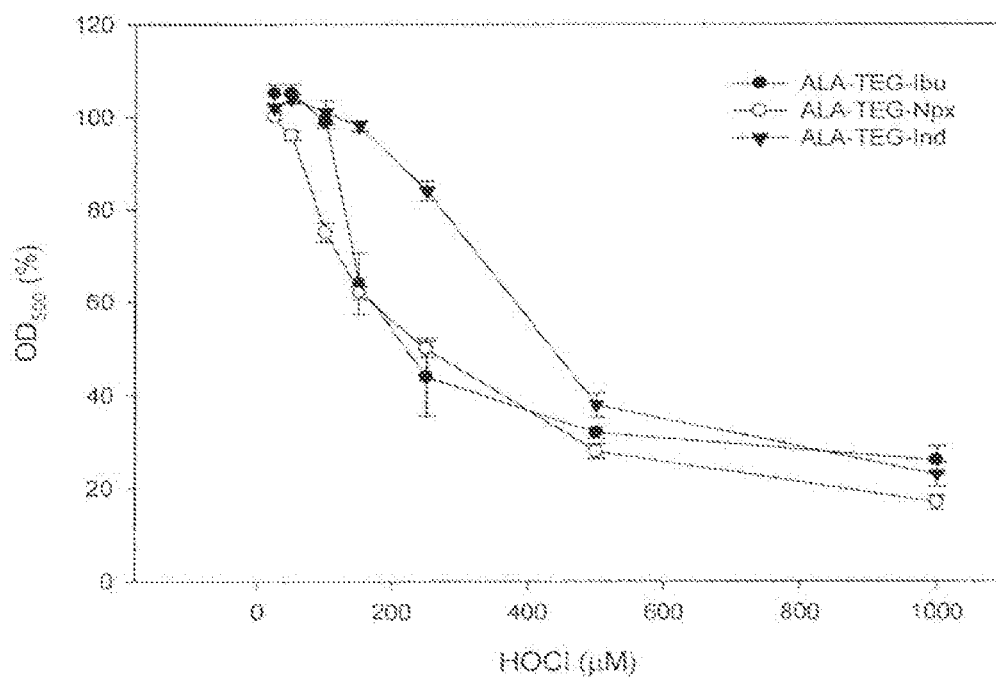
FIGS. 3A-3B depict oxidative destabilization of nanoprodrugs in accordance with an embodiment of the present invention. The results are calculated as the percentage of prodrugs with 100% equal to the amount of prodrugs prior to the addition of HOCl. The results are the mean±S.D. of three experiments.
Figure 3B:
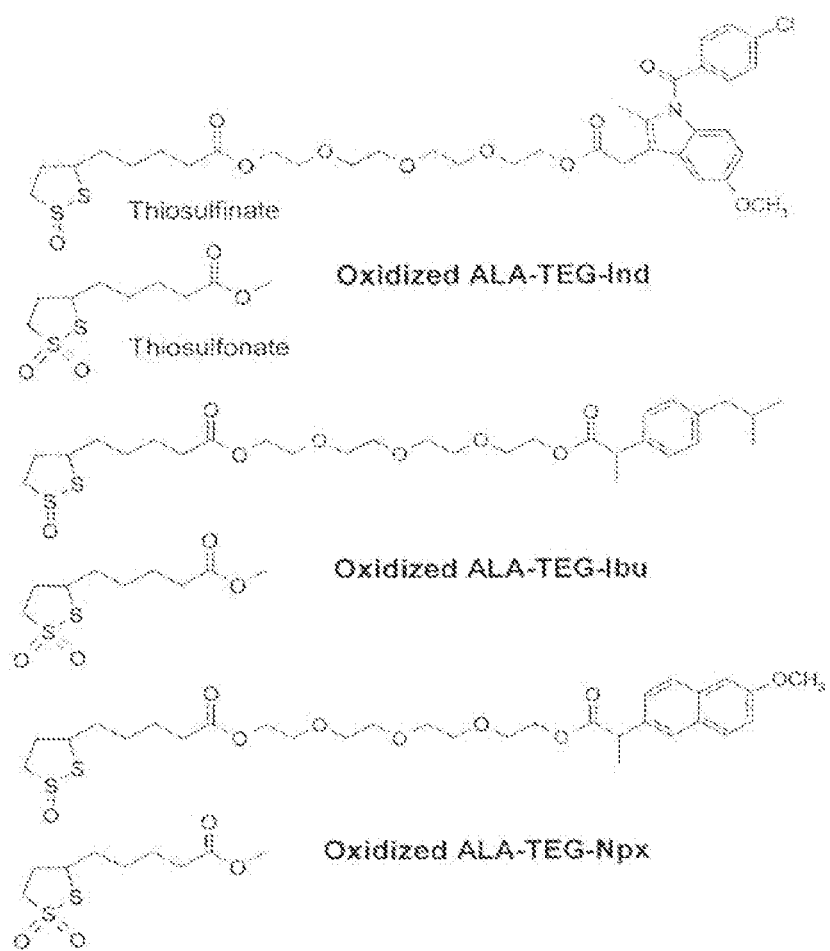

As expected, because of the oxidation of the dithiolane ring system of ALA unit in the bifunctional derivatives of NSAIDs a concentration-dependent reduction in turbidity was observed (FIG. 3A). At lower HOCl concentrations, the reduction was smaller, progressing to a stronger reduction in the higher HOCl concentrations. This can be explained by an induction phase in which the prodrug molecules on the surface scavenge HOCl, which is not sufficient to elicit a destabilization of the nanoprodrugs. After the induction phase, the nanoprodrugs begin to destabilize as the surface molecules scavenge further HOCl to become more and more hydrophilic. The increase in hydrophilicity is ascribed to the formation of thiosulfinate and thiosulfonate after scavenging one and two HOCl molecules per dithiolane ring system, respectively (Biewenga et al., 1994; Napoli et al., 2004). FIG. 3B shows the proposed structures of the oxidized prodrugs. The formation of thiosulfinate would increase the hydrophilicity, which may be not enough to destabilize the nanoprodrugs. Upon scavenging the second HOCl molecule and formation of the thiosulfonate, the more increased hydrophilicity and modified molecular structure of the prodrugs may cause a rapid disintegration of the oxidized prodrugs from the surface, accounting for the burst effect observed after the induction phase.

The amount of HOCl for the three nanoprodrugs to overcome the induction phase was increased in the order of ALA-TEG-Npx, ALA-TEG-Ibu, and ALA-TEG-Ind. The induction phase is less apparent for the nanoprodrug of ALA-TEG-Npx and a rapid reduction was observed after each additional HOCl. This may be ascribed to the relatively lower hydrophobicity of ALA-TEG-Npx which can be assessed from the retention time in RP-HPLC (Table 3). However, comparing the two nanoprodrugs prepared from ALA-TEG-Ibu and ALA-TEG-Ind, the nanoprodrug of ALA-TEG-Ind showed the longest induction phase and the overall reduction in turbidity was less and slower, although it showed a shorter retention time in RP-HPLC and thus, was assessed to be less hydrophobic. This is not in agreement with the assumption that the nanoprodrug prepared from less hydrophobic prodrug may destabilize more quickly upon oxidation.

The oxidative destabilization process may involve the disintegration of the oxidized prodrugs from the surface of nanoprodrugs. The additional increase in hydrophilicity after each oxidation is assumed to be the same for all the three prodrugs. Therefore, in order to explain the observed discrepancy, the steric nature of the oxidized and non-oxidized prodrugs has been taken into account. As shown in FIG. 3B, the structural changes of the prodrugs are related to the formation of thiosulfinate and thiosulfonate, which may cause a steric hindrance and thus enhance the disintegration process of the oxidized prodrugs. Although the same structural changes are introduced to the prodrugs and thus the changes in their steric nature are of same magnitude, the relative effect of these changes could be different between the prodrugs because of the different structure of the NSAIDs. While not wishing to be bound by any particular theory, based on this consideration, the inventors believe that the slower destabilization in case of ALA-TEG-Ind may be due to a smaller relative increase in steric hindrance which can be ascribed to the dominant contribution of the bulkier indomethacin to the steric nature of the molecule, making the effect of the ALA oxidation less pronounced (FIG. 3B).

Example 22

Hydrolytic Activation of Nanoprodrugs

In order to evaluate potential applications of the NSAIDs prodrugs as nanoprodrugs, the water-insoluble hydrophobic prodrugs were formed into nanoprodrugs and the enzymatic reconversion of the prodrugs into the parent drugs was investigated. The formation into the nanoprodrugs may generate a large surface area on which the interaction between hydrolytic enzymes and prodrugs can take place (Huang et. al., 2003; Heckert, et. al., 2008). This interaction would be otherwise impossible due to the insolubility of the prodrugs in aqueous media.

According to the molecular design based on ester bonds, the derivatives were expected to be degraded by enzymatic hydrolysis. However, due to the water-insolubility of the compounds, enzymatic hydrolysis could not be measured in an aqueous solution. A key feature of the nanoprodrugs is that water-insoluble prodrugs can be transported through the aqueous physiological environment once transformed into stable nanoprodrugs.

The inventors expected that the NSAIDs would be released by enzymatic ester hydrolysis of the prodrugs from the surface, which would erode the nanoprodrugs gradually, and ultimately destabilize the nanoprodrugs. Porcine liver esterase was used to establish the in vitro susceptibility of the prodrugs because it is stable and capable of hydrolyzing a wide range of esters (Foroutan and Watson, 1999). This enzyme has been widely used to estimate the in vitro enzymatic activation of ester prodrugs of NSAIDs (Redden et al., 1999; Bonina et al., 2001; Velázquez et al., 2007).

In order to demonstrate the enzymatic hydrolysis, the changes in OD of the nanoprodrug suspensions from the three bifunctional derivatives of ALA and NSAIDs and from the three dimeric derivatives of NSAIDs were monitored. The amount of released drugs was determined at the end of the incubation using RP-HPLC as described above. Because of the different structures of the three prodrugs, a different rate of enzymatic hydrolysis and changes in OD were expected. As shown in FIG. 4A, the nanoprodrug from the indomethacin derivative was more stable compared with the nanoprodrugs prepared from the derivatives of ibuprofen and naproxen. The concentrations of the released drugs were 194 µM, 417 µM and 454 µM for the nanoprodrugs containing ALA-TEG-Ind, ALA-TEG-Ibu and ALA-TEG-Npx, respectively, corresponding to 39%, 83% and 91% in drug release. This relationship was repeated in the nanoprodrugs from the three dimeric derivatives of NSAIDs (FIG. 4B). The rates of hydrolysis for the relatively smaller prodrugs of ibuprofen and naproxen were greater than the rate of hydrolysis for the bulkier indomethacin prodrugs, indicating that steric hindrance was important (Redden et al., 1999).

Interestingly, the enzymatic destabilization of the nanoprodrugs from $Npx_2TEG$ and $Ibu_2TEG$ (FIG. 4B) was much slower when compared to those of the nanoprodrugs from ALA-TEG-Npx and ALA-TEG-Ibu (FIG. 4A), suggesting that the replacement of one ibuprofen and naproxen with ALA has a profound effect on the enzymatic hydrolysis. After al h incubation, less than 10% of parent drugs were hydrolyzed from the nanoprodrugs of $Npx_2TEG$ and $Ibu_2TEG$. In comparison, approximately 90% of drugs were released from the nanoprodrugs of ALA-TEG-Npx and ALA-TEG-Ibu. After a12 h incubation, the concentrations of the released drugs from $Npx_2TEG$ and $Ibu_2TEG$ were comparable with those from ALA-TEG-Npx and ALA-TEG-Ibu after a 1 h incubation. According to the assessment of the hydrophobicity based on the retention time in RP-HPLC (Table 3), the dimeric derivatives are more hydrophobic than the bifunctional derivatives. Therefore, the increased rate of hydrolysis may be attributed to the less hydrophobic nature of the bifunctional prodrugs (Hey et al., 1997).

The stability of all the nanoprodrugs studied was examined in the absence of the enzyme to determine whether the nanoprodrugs were subjected to non-enzymatic degradation or auto-oxidation. The nanoprodrugs were incubated and analyzed under the same condition except for the omission of enzyme. All the nanoprodrugs were found to be stable for the length of the assay (data not shown). Considering the combined results of the enzymatic destabilization and the stability in SIF, SGF and PBS, it can be concluded that the prodrugs are considerably resistant to chemical degradation in aqueous solutions, and enzyme-mediated activation might be required to generate a significant level of parent drugs in vivo.

Example 23

Sequence of Enzymatic Hydrolysis

In order to elucidate the different rates of hydrolysis between the nanoprodrugs observed in FIGS. 4A-4B, the sequence of enzymatic hydrolysis from the nanoprodrugs was studied. While not wishing to be bound by any particular theory, the inventors believe that the increased rate of hydrolysis may be due to the less hydrophobic nature of the bifunctional derivatives.

The sequence of the enzymatic hydrolysis was evaluated by measuring the released NSAIDs and other hydrolyzed species in the supernatant using RP-HPLC. The total amount of NSAIDs and thus the peak intensity were kept constant in the first and second chromatogram by separating the intact nanoprodrugs from the reaction mixture and taking the first and second chromatogram from the same supernatant with an interval of 30 min. In this way, the obtained chromatograms showed a comparable peak intensity and, more importantly, the further hydrolytic degradation of the same set of hydrolyzed species could be analyzed.

Figure 5C:
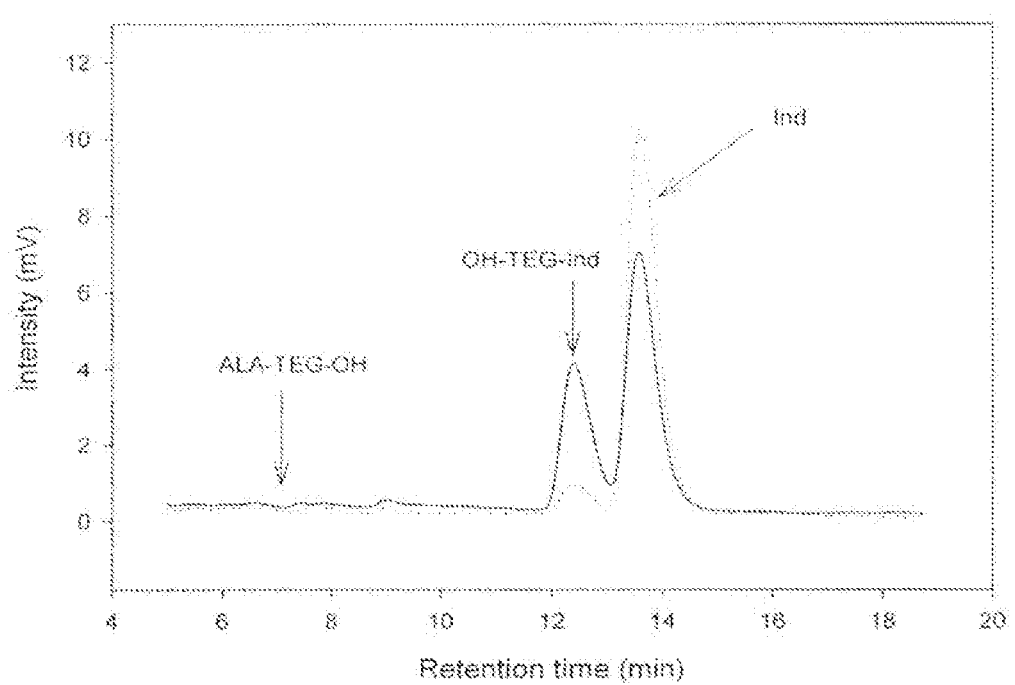

In FIG. 5A-C, the first chromatograms (solid line) were taken from the supernatant after incubation for 5 min and separation of the intact nanoprodrugs from the reaction mixture. The composition of the supernatant is similar to the original mixture except for the hydrolyzed species and omission of the intact nanoprodrugs. After the first chromatogram was taken, the supernatant was incubated for an additional 30 min and the second chromatogram (dotted lines) was taken. As depicted schematically in FIG. 5D, ALA was hydrolyzed first (Pathway B) followed by ibuprofen, naproxen and indomethacin, indicating that ALA is more accessible to the enzymes. The results suggest that the replacement one NSAID molecule with ALA leads to the increase in hydrophilicity and decrease in steric hindrance towards the enzymes, consequently increasing the rate of hydrolysis of the prodrugs (Hey et al., 1997; Redden et al., 1999)

Example 24

Recovery of NSAIDs from Oxidized Nanoprodrugs

After the oxidative and enzymatic destabilization of the nanoprodrugs were studied separately, the inventors evaluated the influence of the oxidation of nanoprodrugs on the enzymatic prodrug activation. First, the inventors examined the chemical stability of the NSAID prodrugs in the presence of HOCl. The oxidative degradation of the prodrugs was determined by measuring the amount of intact prodrugs after HOCl treatment. After treatment of the nanoprodrugs with a two-fold molar excess of HOCl in PBS (pH 7.4), no intact prodrugs were detected by RP-HPLC. HOCl scavenging by the nanoprodrugs occurred instantaneously and completely as evidenced by DTNB assay. After incubation for 2 min with a two-fold molar excess of HOCl, no remaining HOCl was detected, indicating that one ALA moiety scavenged at least two molecules of HOCl (Biewenga et al., 1994). To see whether these completely oxidized prodrugs are still available as prodrugs of the NSAIDs, the HOCl-treated nanoprodrugs were incubated in the presence of esterase. In comparison with non-oxidized controls, the released parent drugs from the oxidized nanoprodrugs were 80% (p<0.05), 87% (p<0.01) and 71% (p<0.001) for the nanoprodrugs from ALA-TEG-Ibu, ALA-TEG-Npx and ALA-TEG-Ind, respectively (FIGS. 5A-5C). This study shows that the ALA-containing derivatives of NSAIDs can serve as prodrugs even after the ALA moieties have been oxidized completely.

Example 25

Effect of Nanoprodrug Oxidation on the Rate of Enzymatic Hydrolysis

The oxidation of the prodrugs results in the destabilization of the nanoprodrugs, which is attributed to the decreased hydrophobicity of the oxidized prodrugs, consequently increasing the solubility in an aqueous environment. It can be hypothesized that the oxidation of the prodrugs on the surface and their increased hydrophilicity may lead to an expulsion of the oxidized prodrugs and make the otherwise tightly assembled surface structure loose. This may change the morphology and surface structure of the nanoprodrugs, which strongly influences the interaction between the oxidized prodrugs and hydrolytic enzymes.

Figure 7A:
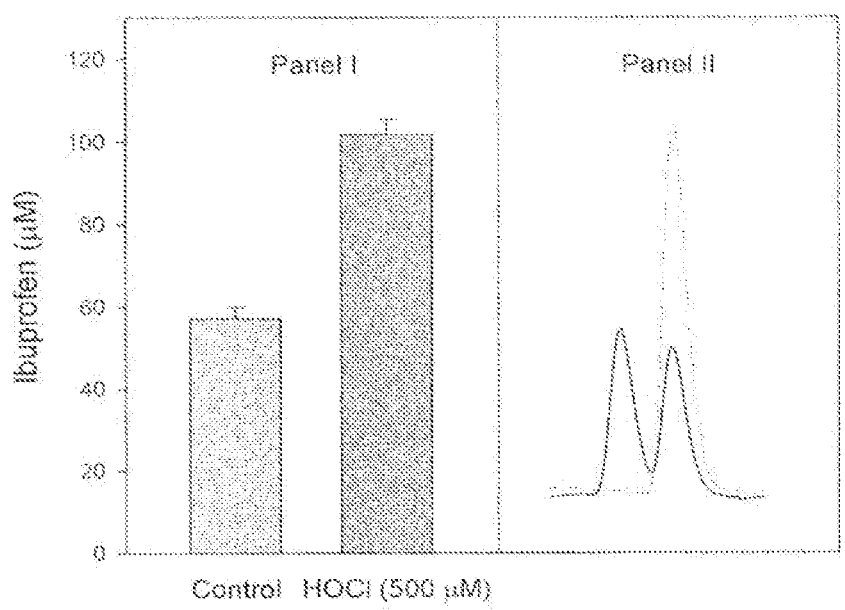
Figure 7B:
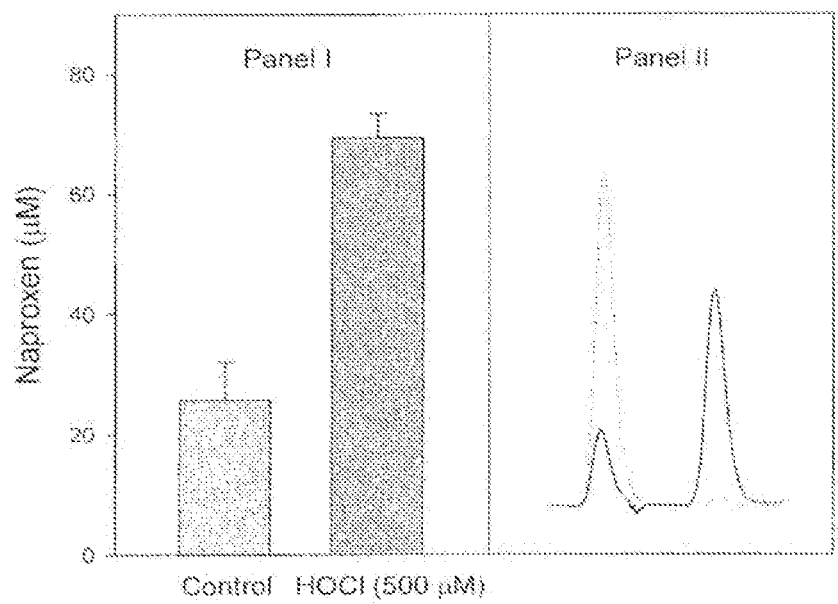

The effect of oxidation on the rate of enzymatic hydrolysis is shown in FIGS. 7A-7C. Although the total amount of available prodrugs was higher in the non-oxidized nanoprodrugs (FIGS. 6A-6C), the amount of hydrolyzed drugs from the oxidized nanoprodrugs was significant higher when it was determined immediately after the addition of esterase and separation of the intact nanoprodrugs from the reaction mixture. The amount of hydrolyzed drugs was increased approximately two, three and four times for ALA-TEG-Ibu (p<0.001), ALA-TEG-Npx (p<0.001) and ALA-TEG-Ind (p<0.01), respectively. Noteworthy, the selectivity for the oxidized nanoprodrugs increased with the decreasing rate of hydrolysis for the non-oxidized nanoprodrugs. The amount of hydrolyzed drugs from the non-oxidized nanoprodrug of ALA-TEG-Ind is about 10 and 25 times less than those of ALA-TEG-Ibu and ALA-TEG-Npx, respectively, which makes the effect of the oxidation more pronounced for ALA-TEG-Ind. It has been also found that the sequence of hydrolysis was similar to those of the non-oxidized prodrugs (Panel II).

These findings confirm the previous assumption that the oxidation of the ALA-containing prodrugs supports the enzymatic hydrolysis probably by making the oxidized prodrugs more accessible to the enzymes, which can be attributed to the increased hydrophilicity and water-solubility (Napoli et al., 2004) and less compact assembling of the oxidized prodrugs.

It should be noted that the observed pattern and rate of the hydrolysis under the in vitro condition may not reflect in vivo fate of the nanoprodrugs. Considering the rate of hydrolysis in the absence of the oxidant, it can be expected that a considerable amount of nanoprodrugs might be hydrolyzed before they have reached the site where ROS are overproduced. In this regard, the more selective nanoprodrug of ALA-TEG-Ind would be an appropriate candidate for in vivo study. The results also provide a rational approach for further development of prodrugs, based on the hydrophobicity, in order to obtain nanoprodrugs with desired stability, rate of hydrolysis and selectivity.

Example 26

Synthesis of Antioxidant Compounds

α-Lipoic acid (2.48 g, 12 mmol, 1.2 equiv.) and the compounds containing two hydroxyl groups (1,12-dodecanediol ("1,12-DD")) (10 mmol OH, 1.0 equiv.) in 20 mL of anhydrous dichloromethane (DCM) were reacted with 4-(dimethylamino)-pyridine (DMAP, 1.47 g, 12 mmol, 1.2 equiv.) in the presence of molecular sieve (60 Å, 10-20 mesh beads) for 10 min at room temperature. N-(3-Dimethylaminopropyl)-N-ethylcarbodiimide hydrochloride (EDCI, 2.3 g, 12 mmol, 1.2 equiv.) was added portionwise over 10 min and the reaction mixture was stirred for 12 h at room temperature in the dark, filtered, and then concentrated under vacuum to reduce the volume. The resulting reaction mixture was purified using silica gel by direct loading onto the column without further preparation. The solvent was removed under reduced pressure to give the products. See also International Application No. PCT/US08/88541, which is incorporated herein by reference in its entirety as though fully set forth.

Scheme 3

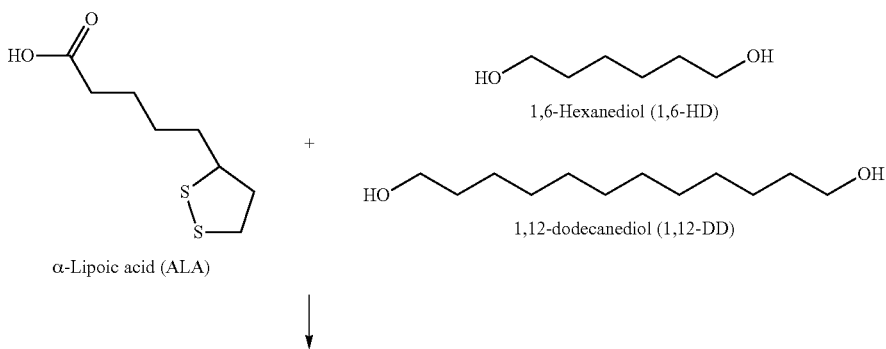

-continued

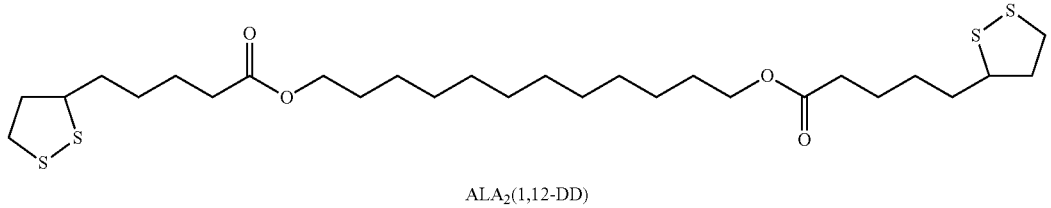

ALA₂(1,12-DD)

Example 27

Preparation of Nanospheres from the Mixture of the Hydrophobic NSAIDs Derivatives and Poly(Lactide-Co-Glycolide)(PLGA)

Nanospheres were prepared according to the method described above using spontaneous emulsification from a mixture of the hydrophobic derivatives of NSAIDs (25 mg) with PLGA (100 mg) (Sigma, P2191, lactide:glycolide 50:50, mol. wt 40,000-75,000), α-tocopherol (25 mg).

TABLE 5

Size and Polydispersity Index (P.I.)

| NSAID-containing hydrophobic compounds | Second components | Size (nm) | P.I. |
|---|---|---|---|
| 25 mg Tetraethylene glycol(ibuprofen)₂ | 100 mg PLGA | 155 ± 48 | 0.16 |
| 25 mg Tetraethylene glycol(ibuprofen)₂ | 25 mg α-tocopherol | 189 ± 55 | 0.13 |
| 20 mg Tetraethylene glycol(ibuprofen)₂ | 50 mg ALA₂(1,12-DD) | 204 ± 62 | 0.145 |

Example 28

Enzymatic Hydrolysis of the Antioxidant and NSAID Nanospheres

To the suspensions of nanospheres prepared from the 50:50 mixture of the derivative of NSAIDs (Ibu₂TEG and Npx₂TEG) and the antioxidant compound ALA₂(1,6-HD) in phosphate buffered saline (pH 7.4) containing 300 µM NSAIDs unit, esterase was added to a final concentration of 2 U/mL. The reaction mixture was incubated at 25° C. To determine the amount of enzymatically hydrolyzed NSAIDs, samples were taken with predetermined time interval, centrifuged for 10 min at 20.000×g, and the supernatants were analyzed by RP-HPLC using C18 column. The separation was performed under isocratic condition with 60-65% acetonitrile containing 0.1% TFA, and naproxen (Npx) was detected at 254 nm and ibuprofen (Ibu) was detected at 220 nm.

To the suspensions of nanospheres prepared from the 50:50 mixture of the derivative of NSAIDs (Ibu₂TEG) and the two antioxidant compounds (ALA₂(1,6-HD) or ALA₂(1,12-DD) in phosphate buffered saline (pH 7.4) containing 300 µM NSAIDs unit, esterase was added to a final concentration of 2 U/mL. The reaction mixture was incubated at 25° C. To determine the amount of enzymatically hydrolyzed NSAIDs, samples were taken with predetermined time interval, centrifuged for 10 min at 20.000×g, and the supernatants were analyzed by RP-HPLC using C18 column. The separation was performed under isocratic condition with 60-65% acetonitrile containing 0.1% TFA, and ibuprofen (Ibu) was detected at 220 nm.

Example 29

HOCl Scavenging and Myeloperoxidase Inhibition by the Antioxidant and NSAID Nanospheres Compared with Those of the Antioxidant Nanosphere in the Myeloperoxidase Assay System The reaction mixture contained the following reagents in a final volume of 1 mL. 1.0 U of myeloperoxidase, 300 mM NaCl, 15 mM of taurine, 200 µM of $H_2O_2$, 2.5 U of esterase and nanospheres containing 100 µM of indomethacin. The assay was initiated by addition of $H_2O_2$. The reaction mixture was incubated for 15 min at 37° C. and a sample was taken. After addition of 100 µM of $H_2O_2$, the reaction mixture was incubated for an additional 15 min at 37° C. and second sample was taken. After the addition of 100 µM of $H_2O_2$, the reaction mixture was incubated for an additional 15 min at 37° C. and third sample was taken. To determine the chlorinating activity of the myeloperoxidase, the reaction was stopped by the addition of 30 µl of catalase (4U/µL) to 150 µL of the samples. The samples were centrifuged for 10 min at 20.000×g. After addition of 115 µL of 2-nitro-5-thio-benzoate (0.45 mM) and 905 µL of PBS to the clear supernatant of the samples, absorbance was measured at 412 nm.

Example 30

Anticancer and Antiproliferative Effects of the NSAID Nanoprodrugs: Cell Counting The U87-MG human glioma cell line was obtained from American Type Culture Collection (ATCC) (Rockville, Md., USA). The cells were grown and maintained in Minimum Essential Medium (MEM) (Invitrogen) containing antibiotics 100 U/mL penicillin (Invitrogen) and 100 µg/mL streptomycin (Invitrogen), and supplemented with 10% fetal bovine serum (FBS) (Invitrogen). Cells were kept at 37° C. in a humidified atmosphere including 5% $CO_2$.

Nanoprodrugs were prepared from the monomeric derivative Ibu₂TEG (25 mg) as described in Example 6 and dialyzed in phosphate buffered saline (PBS) over night. The human glioma cells (U87-MG) were seeded in a 25 cm² flask at 2.5×10⁵ cells/5 mL and allowed to grow for 24 h. The medium was changed and the cells were treated with nanoprodrugs at final concentration ranging from 10 to 100 µM for the monomeric derivative Ibu₂TEG. After a 3-day treatment, the medium was remove, cells were washed with PBS and 1 mL of 0.25% trypsin/EDTA (Gibco) was added to detach the cells. The cells were counted immediately in a hemacytometer (See FIG. 8). Control culture was treated with PBS.

Figure 8:
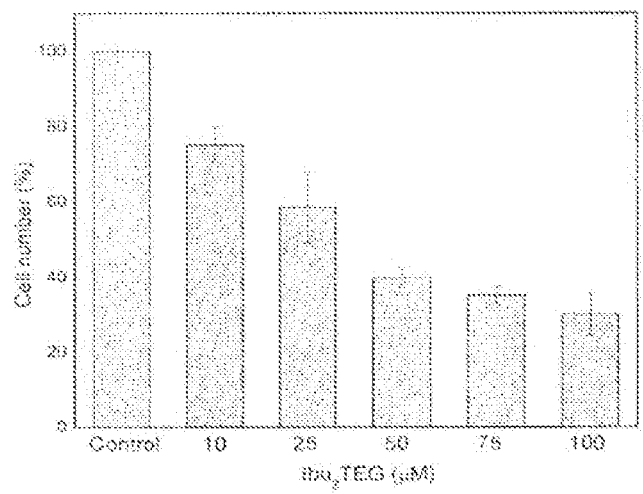
FIG. 8 depicts the effect of nanoprodrug prepared from Ibu$_2$TEG on cell proliferation of the human glioma cell line U87-MG in accordance with an embodiment of the present invention.

To investigate the effect of NSAID nanoprodrugs on cell growth of the human glioma cell line U87-MG, the cells were treated with the nanoprodrug prepared from Ibu$_2$TEG. Treatment of the cells for 3 days resulted in significant decrease in cell number when compared to the control culture (FIG. 8).

Example 31

Figure 9:
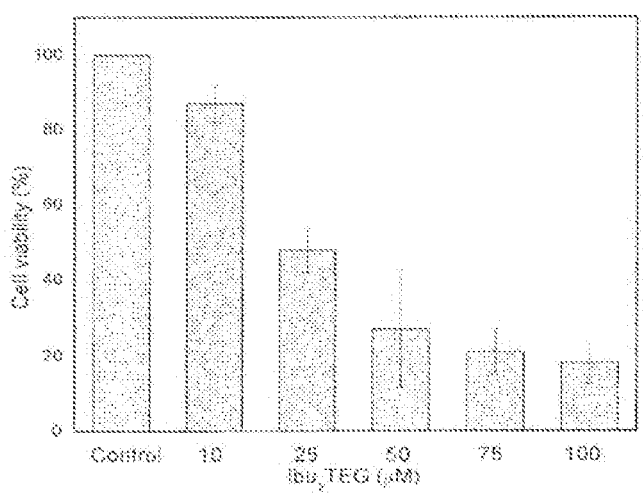
FIG. 9 depicts the effect of nanoprodrug prepared from Ibu$_2$TEG on cell viability of the human glioma cell line U87-MG in accordance with an embodiment of the present invention.
Figure 10:
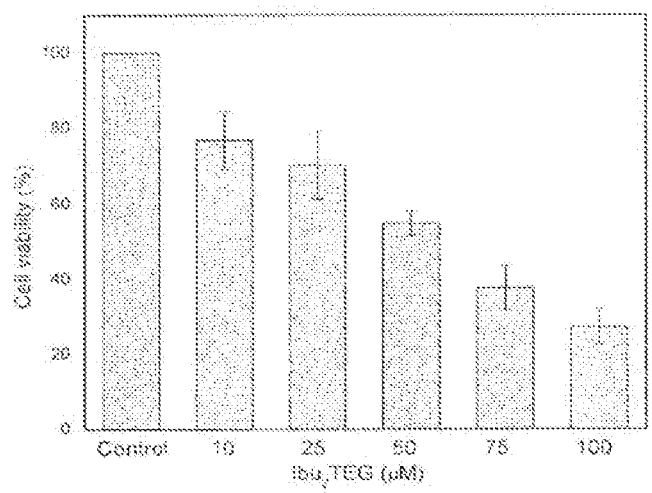
FIG. 10 depicts the effect of nanoprodrug prepared from Ibu$_2$TEG and α-tocopherol on cell viability of the human glioma cell line U87-MG in accordance with an embodiment of the present invention.
Figure 11:
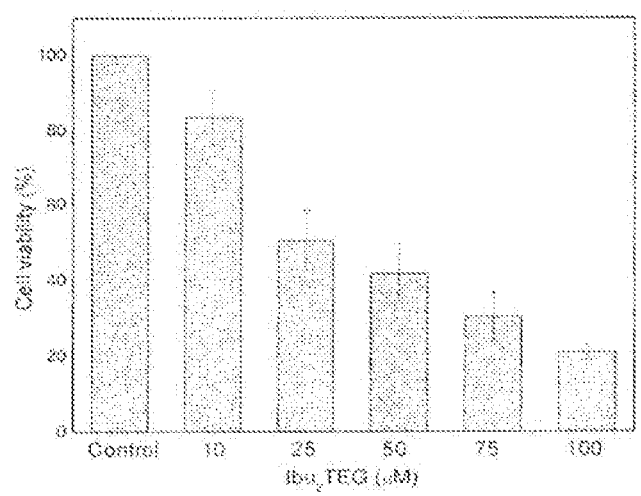
FIG. 11 depicts the effect of nanoprodrug prepared from Ibu$_2$TEG and PLGA on cell viability of the human glioma cell line U87-MG in accordance with an embodiment of the present invention.
Figure 12:
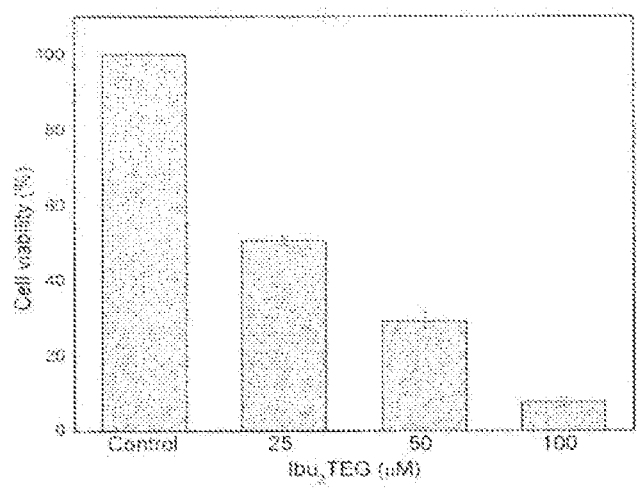
FIG. 12 depicts the effect of nanoprodrug prepared from Ibu$_2$TEG and ALA$_2$(1,12-DD) on cell viability of the human glioma cell line U87-MG in accordance with an embodiment of the present invention.
Figure 13:
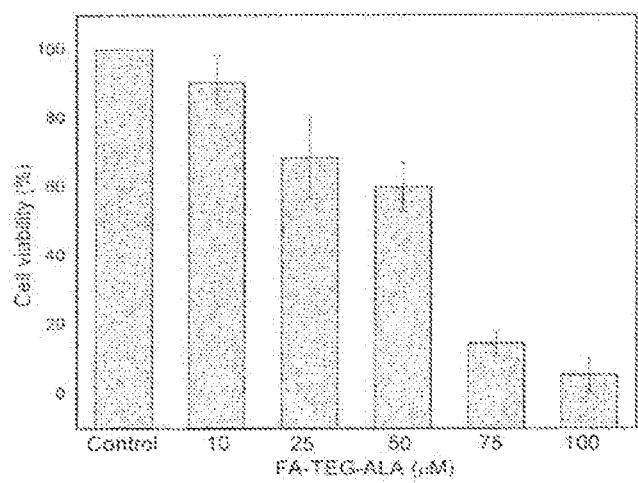
FIG. 13 depicts the effect of nanoprodrug prepared from FA-TEG-ALA on cell viability of the human glioma cell line U87-MG in accordance with an embodiment of the present invention.
Figure 14:
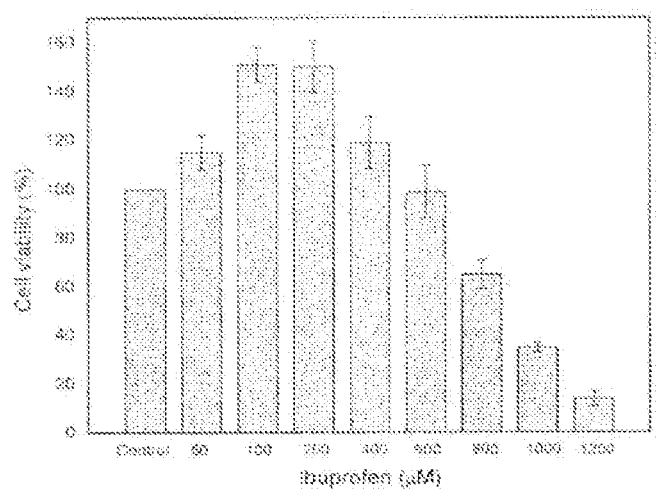
FIG. 14 depicts the effect of ibuprofen on cell viability of the human glioma cell line U87-MG in accordance with an embodiment of the present invention.

Anticancer and Antiproliferative Effects of the NSAID Nanoprodrugs 2: WST-1 Assay Growth inhibition was evaluated by the WST-1 (water-soluble tetrazolium salt) colorimetric assay (Boehringer Mannheim) according to the manufacturer's instructions. Nanoprodrugs were prepared from the monomeric derivative Ibu$_2$TEG or dimeric derivative FA-TEG-ALA (20 mg) as described in Example 6 and dialyzed in phosphate buffered saline (PBS) over night. The human glioma cells (U87-MG) were seeded on a 96-well microtiter plate at $2 \times 10^3$ cells/well for 24 h before treatment with drugs at final concentration ranging from 10 to 100 µM and 100 to 1000 µM for ibuprofen nanoprodrugs and ibuprofen, respectively. After 72 h of treatment, each culture medium containing the drugs was removed, cells were washed with 100 µL of PBS, and 90 µL of culture medium and 10 µL of WST-1 solution were added to each of the wells. Cells were incubated at 37° C. for 1-4 h, and the absorbance was read by an ELISA plate reader at 450 nm. The cell viability was calculated as follows: Cell viability (%)=(Abs$_s$/Abs$_c$)×100, where Abs$_s$ is the absorbance of cells treated with drugs and Abs$_c$ is the absorbance of control cells incubated with cell culture medium only (See FIG. 9).

In order to investigate the effect of NSAID nanoprodrugs on cell viability of human glioma cell line, the effects of three different formulation of the nanoprodrugs were studied. The nanoprodrugs were prepared from Ibu$_2$TEG or FA-TEG-ALA only, a mixture of Ibu$_2$TEG and polymer PLGA, a mixture of Ibu$_2$TEG and α-tocopherol, or a mixture of Ibu$_2$TEG and ALA$_2$DD. It is important to note that, regardless of how the nanoprodrugs were prepared, the three different nanoprodrug formulations showed a concentration-dependent effect on cell viability (see FIG. 10-FIG. 14). On the other hand, free ibuprofen did not show any significant effect up to 600 µM.

Example 32

Cytotoxic Effect of the NSAID Nanoprodrugs on Non-Tumorigenic Cell: WST-1 Assay

Figure 15:
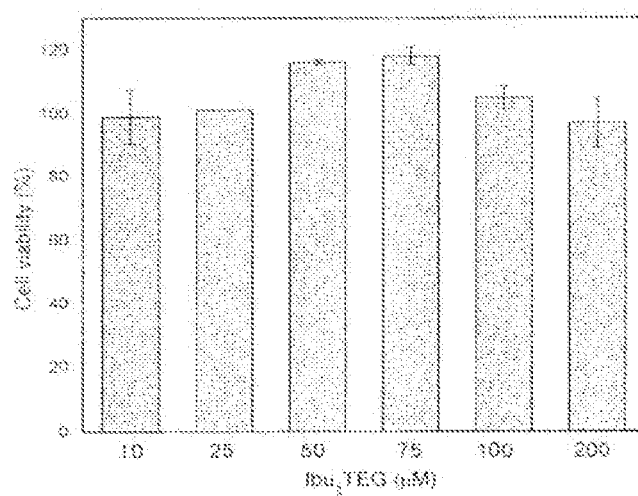
FIG. 15 depicts the cytotoxic effect of nanoprodrug prepared from Ibu$_2$TEG on the non-tumorigenic HBVEC in accordance with an embodiment of the present invention.

Cytotoxic effect of the nanoprodrug on a healthy cell line was evaluated by the WST-1 (water-soluble tetrazolium salt) colorimetric assay (Boehringer Mannheim) according to the manufacturer's instructions. Human brain vascular endothelial cell line (HBVEC) were seeded on a 96-well microtiter plate at $2 \times 10^3$ cells/well for 24 h before treatment with drugs at final concentration ranging from 10 to 100 µM and 100 to 1000 µM for ibuprofen nanoprodrugs and ibuprofen, respectively. After 72 h of treatment, each culture medium containing the drugs was removed, cells were washed with 100 µL of PBS, and 90 µL of culture medium and 10 µL of WST-1 solution were added to each of the wells. Cells were incubated at 37° C. for 1-4 h, and the absorbance was read by an ELISA plate reader at 450 nm. The cell viability was calculated as follows: Cell viability (%)=(Abs$_s$/Abs$_c$)×100, where Abs$_s$ is the absorbance of cells treated with drugs and Abs$_c$ is the absorbance of control cells incubated with culture medium only (See FIG. 15).

To asses whether the NSAID nanoprodrugs affect the cell viability of normal healthy cells, the cell viability of human brain vascular endothelial cell line (HBVEC) was measured after treatment with the nanoprodrugs. As observed, 200 µM of the nanoprodrug had no inhibitory effect on the cell viability of HBVEC.

Example 33

Anticancer and Antiproliferative Effects of the NSAID Nanoprodrug: Propidium Iodide Cell death was assessed by fluorescent image analysis of propidium iodide uptake (Macklis and Madison, (1990) *Progressive incorporation of propidium iodide in cultured mouse neurons correlates with declining electrophysiological status: a fluorescence scale of membrane integrity.* J. NEUROSCI. METHODS 31:43-46).

The human glioma cells (U87-MG) were seeded at $1 \times 10^5$ cells per well in 6-well plates, and allowed to grow for 24 h. The medium was changed and the cells were treated with 50 or 100 µM of nanoprodrug of Ibu$_2$TEG or 200 µM of ibuprofen dissolved in DMSO for 72 h. Control cultures were treated with DMSO or cell culture medium only. After the end of treatment, glioma cells were incubated with 5 µM of propidium iodide (Sigma) for 1 h. Propidium iodide fluorescence was excited at 515-560 nm using an inverted microscope fitted with a standard rhodamine filter.

To verify whether the NSAID nanoprodrugs could induce cell death, glioma cells were treated with a representative nanoprodrug for 3 days and then the cell death was analyzed by propidium iodide incorporation. Propidium iodide is excluded from healthy cells, but following cell death and loss of membrane integrity, propidium iodide enters cells, binds to DNA and becomes highly fluorescent (See FIGS. 16A-16E). When the cells were treated with 50 or 100 µM of nanoprodrugs, a significant amount of propidium iodide incorporation was observed, indicating an intense cell death, while the control cells and cells treated with 200 µM of ibuprofen showed no significant propidium iodide incorporation.

Various embodiments of the invention are described above in the Detailed Description. While these descriptions directly describe the above embodiments, it is understood that those skilled in the art may conceive modifications and/or variations to the specific embodiments shown and described herein. Any such modifications or variations that fall within the purview of this description are intended to be included therein as well. Unless specifically noted, it is the intention of the inventors that the words and phrases in the specification and claims be given the ordinary and accustomed meanings to those of ordinary skill in the applicable art(s).

The foregoing description of various embodiments of the invention known to the applicant at this time of filing the application has been presented and is intended for the purposes of illustration and description. The present description is not intended to be exhaustive nor limit the invention to the precise form disclosed and many modifications and variations are possible in the light of the above teachings. The embodiments described serve to explain the principles of the invention and its practical application and to enable others skilled in the art to utilize the invention in various embodiments and with various modifications as are suited to the particular use contemplated. Therefore, it is intended that the invention not be limited to the particular embodiments disclosed for carrying out the invention.

While particular embodiments of the present invention have been shown and described, it will be obvious to those skilled in the art that, based upon the teachings herein, changes and modifications may be made without departing from this invention and its broader aspects and, therefore, the appended claims are to encompass within their scope all such changes and modifications as are within the true spirit and scope of this invention. It will be understood by those within the art that, in general, terms used herein are generally intended as "open" terms (e.g., the term "including" should be interpreted as "including but not limited to," the term "having" should be interpreted as "having at least," the term "includes" should be interpreted as "includes but is not limited to," etc.).

What is claimed is:

1. A molecule having formula I:

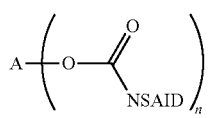

(I)

wherein the A is a moiety that is formed by esterification of at least two free esterifiable hydroxyl groups on a polyol selected from the group consisting of

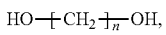

wherein n on the polyol is an integer between 3 and 16,

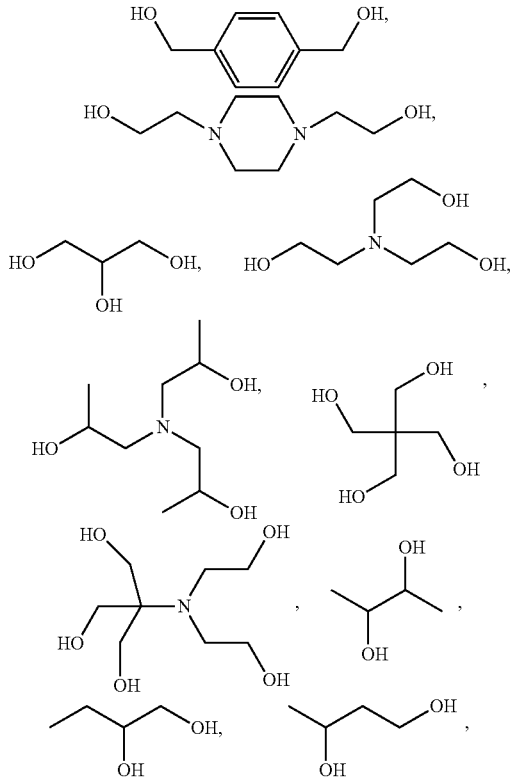

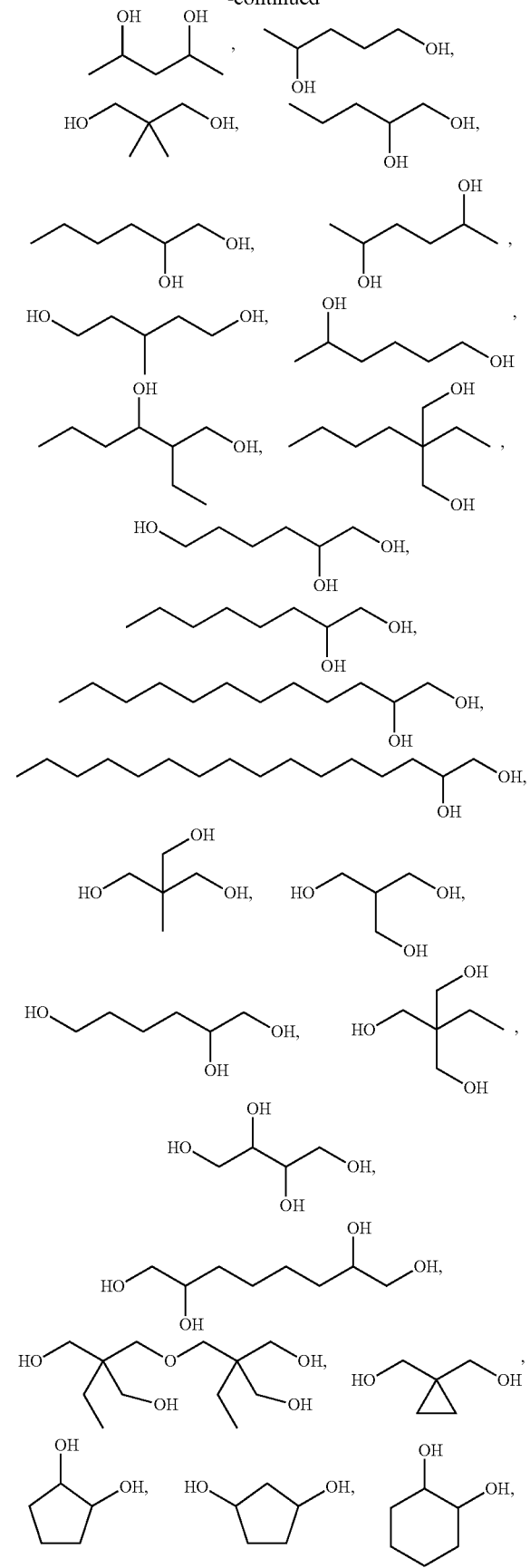

-continued

-continued

and n of Formula I is an integer of at least two, wherein the NSAID is selected from the group consisting of aspirin, ibuprofen, ketoprofen, fenoprofen, fenbufen, indomethacin, diclofenac, ketorolac, tolmetin, flufenamic acid, mefenamic acid, tolfenamic acid, meclofenamic acid, niflumic acid, sulindac, sulindac sulfide and combinations thereof.

2. The molecule of claim 1, wherein the polyol is

wherein n on the polyol is an integer between 3 and 16.

3. A nanosphere comprising a molecule of formula I:

$$A\text{---}\left(\text{---O---}\underset{\text{NSAID}}{\overset{\text{O}}{\text{C}}}\right)_n \quad \text{(I)}$$

wherein the A is selected from the group consisting of branched and unbranched alkyl, and heteroatom-containing branched and unbranched alkyl; and n of formula I is an integer of at least two, wherein the NSAID is selected from the group consisting of aspirin, ibuprofen, flurbiprofen, ketoprofen, fenoprofen, fenbufen, naproxen, indomethacin, diclofenac, ketorolac, tolmetin, flufenamic acid, mefenamic acid, tolfenamic acid, meclofenamic acid, niflumic acid, sulindac, sulindac sulfide and combinations thereof, wherein the nanosphere further comprises a molecule of formula IV,

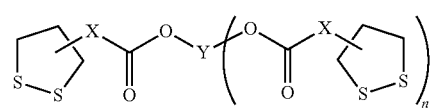
wherein X is a substituted, unsubstituted, branched or unbranched chain of carbon atoms;
Y is a moiety formed by esterification of the hydroxyl groups of a polyol selected from the group consisting of
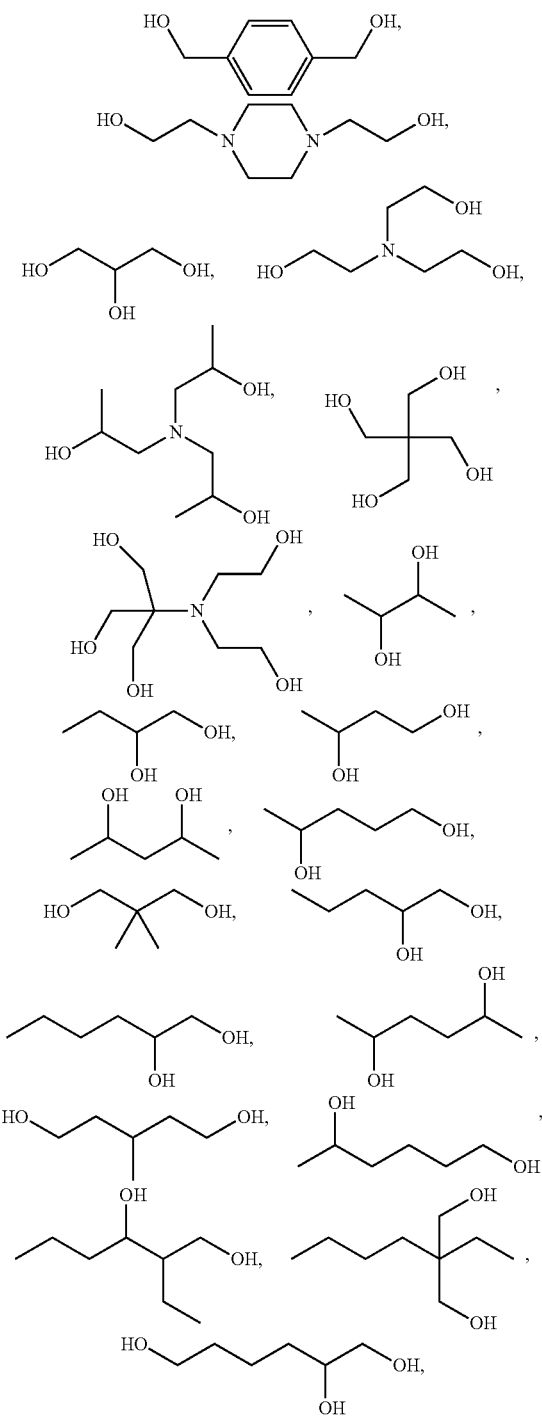

-continued

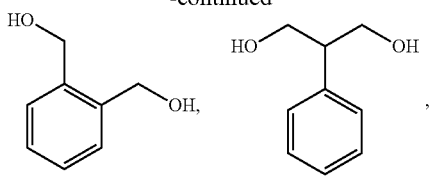, 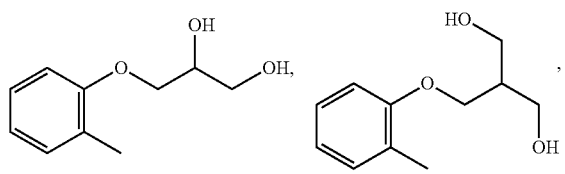,

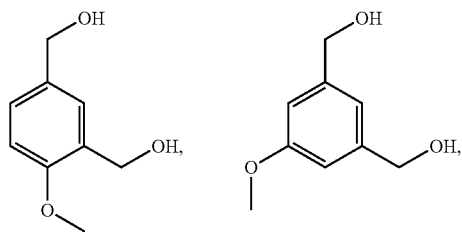,

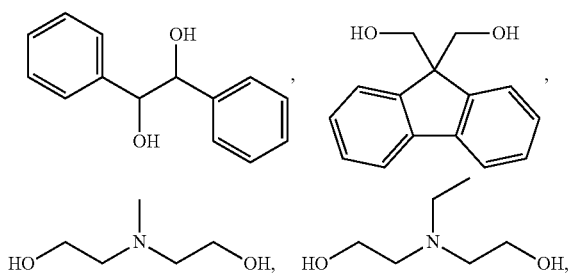,

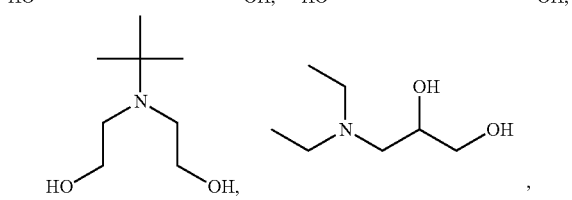,

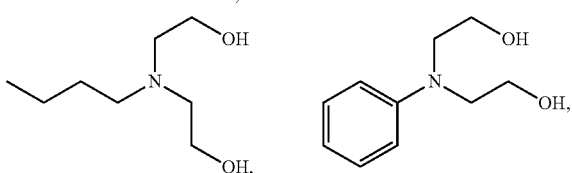,

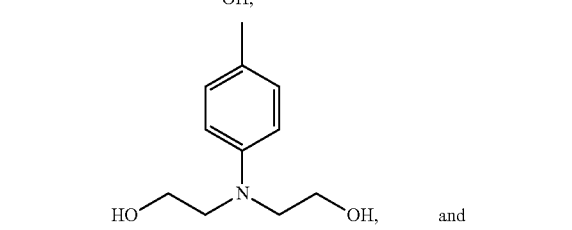 and

-continued

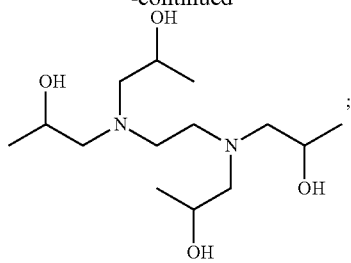;

and
n of formula (IV) is an integer of at least one.

4. The nanosphere of claim 3, wherein the molecule of formula IV is a molecule of formula V:

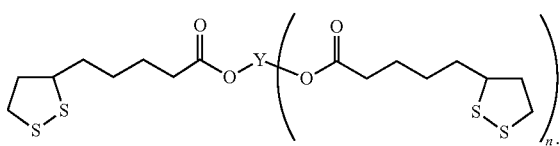

(V)

5. The nanosphere of claim 3, further comprising a tocopherol.

6. The nanosphere of claim 3, further comprising a polymer.

7. The nanosphere of claim 6, wherein the polymer is selected from the group consisting of a hydrophobic polymer, amphiphilic polymer, and hydrophobically modified hydrophilic polymer.

8. The nanosphere of claim 6, wherein the polymer is selected from the group consisting of a polyanhydride, polyester, polyorthoester, polyesteramide, polyacetal, polyketal, polycarbonate, polyphosphoester, polyphosphazene, polyvinylpyrrolidone, polydioxanone, poly(malic acid), poly(amino acid), polymer of N-2-(hydroxypropyl) methacrylamide (HPMA), polymer of N-isopropyl acrylamide (NIPAAm), polyglycolide, polylactide, copolymer of glycolide and lactide, and combinations thereof.

9. The nanosphere of claim 6, wherein the polymer contains a side group selected from the group consisting of a hydrophobic molecule, hydrophilic molecule, and amphiphilic molecule.

10. The nanosphere of claim 9, wherein the side group is a therapeutic or diagnostic agent.

11. The nanosphere of claim 10, wherein the therapeutic agent is a chemotherapeutic selected from the group consisting of paclitaxel, doxorubicin, temozolomide, 5-fluorouracil, and camptothecin.

12. The nanosphere of claim 10, wherein the therapeutic agent is selected from the group consisting of a peptide, antisense nucleic acid, and protein.

13. The nanosphere of claim 6, wherein the polymer contains a hydrophobic side group selected from the group consisting of an aromatic group, amino acid alkyl ester, and aliphatic group.

14. A method of treating a disease condition in a subject in need thereof, comprising:
providing a therapeutically effective quantity of the nanosphere of claim 3; and
administering the therapeutically effective quantity to the subject.

15. A method of delivering a therapeutic agent, comprising:
   providing a composition comprising the therapeutic agent and a nanosphere selected from the group consisting of:
   the nanosphere of claim 3,
   the nanosphere of claim 3, further comprising a tocopherol, and
   the nanosphere of claim 3, further comprising a polymer; and
   administering the composition to the subject.

16. A composition comprising:
   a nanosphere comprising a molecule of Formula (I); and
   a nanosphere comprising a molecule of formula IV, wherein Formula (I) is:

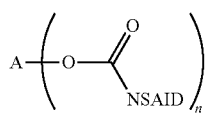
(I)

wherein the A is selected from the group consisting of branched and unbranched alkyl, and heteroatom-containing branched and unbranched alkyl; and n of formula I is an integer of at least two,
wherein the NSAID is selected from the group consisting of aspirin, ibuprofen, flurbiprofen, ketoprofen, fenoprofen, fenbufen, naproxen, indomethacin, diclofenac, ketorolac, tolmetin, flufenamic acid, mefenamic acid, tolfenamic acid, meclofenamic acid, niflumic acid, sulindac, sulindac sulfide and combinations thereof, and Formula (IV) is:

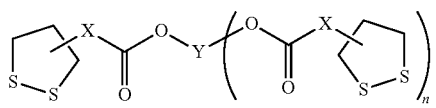
(IV)

wherein X is a substituted, unsubstituted, branched or unbranched chain of carbon atoms; Y is a moiety formed by esterification of the hydroxyl groups of a polyol selected from the group consisting of

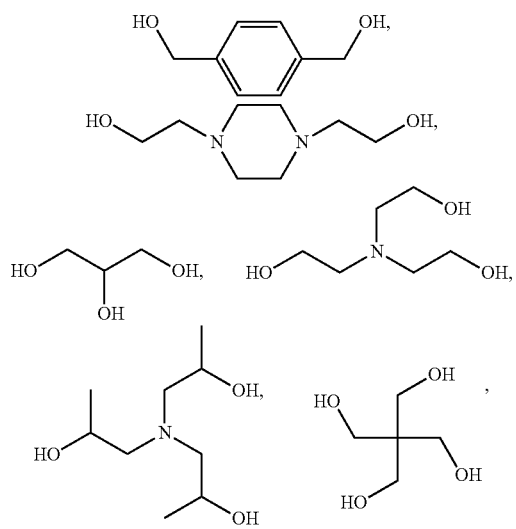

-continued

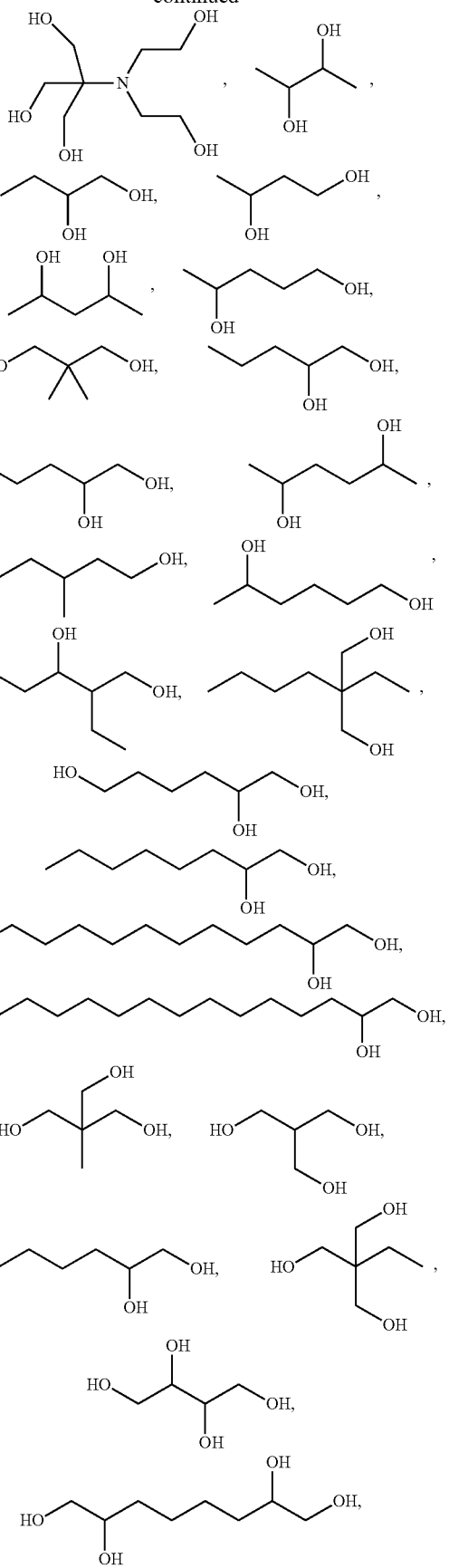

-continued
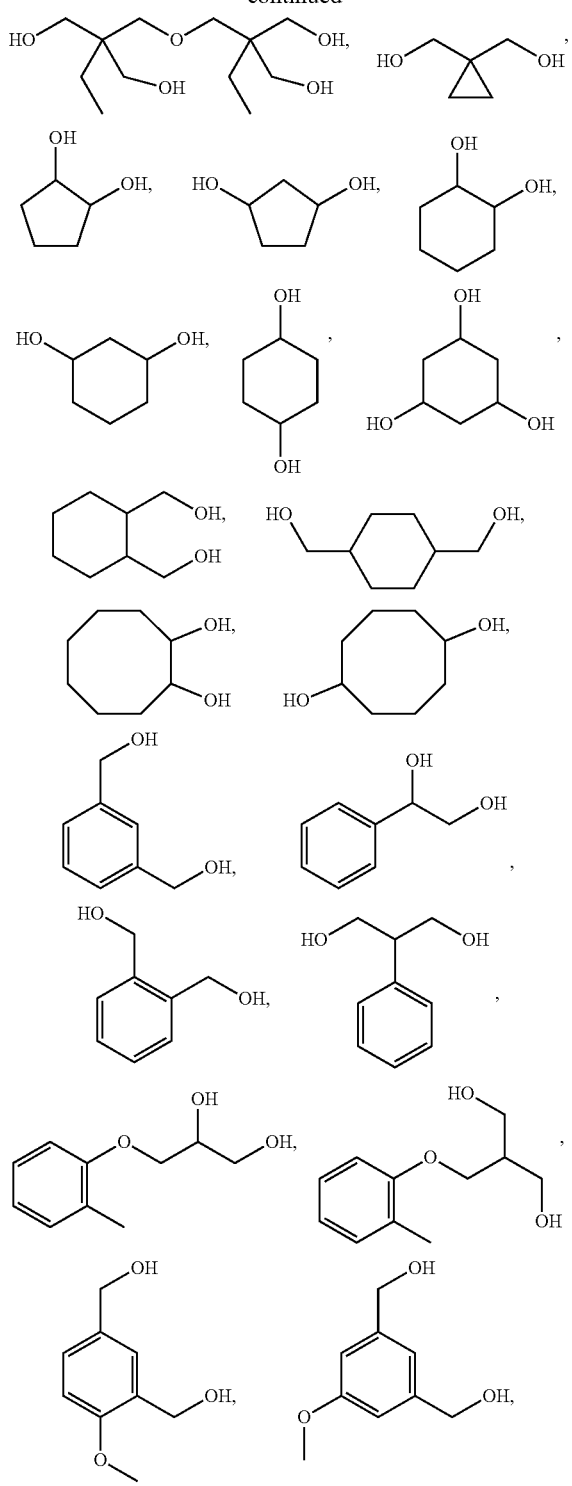
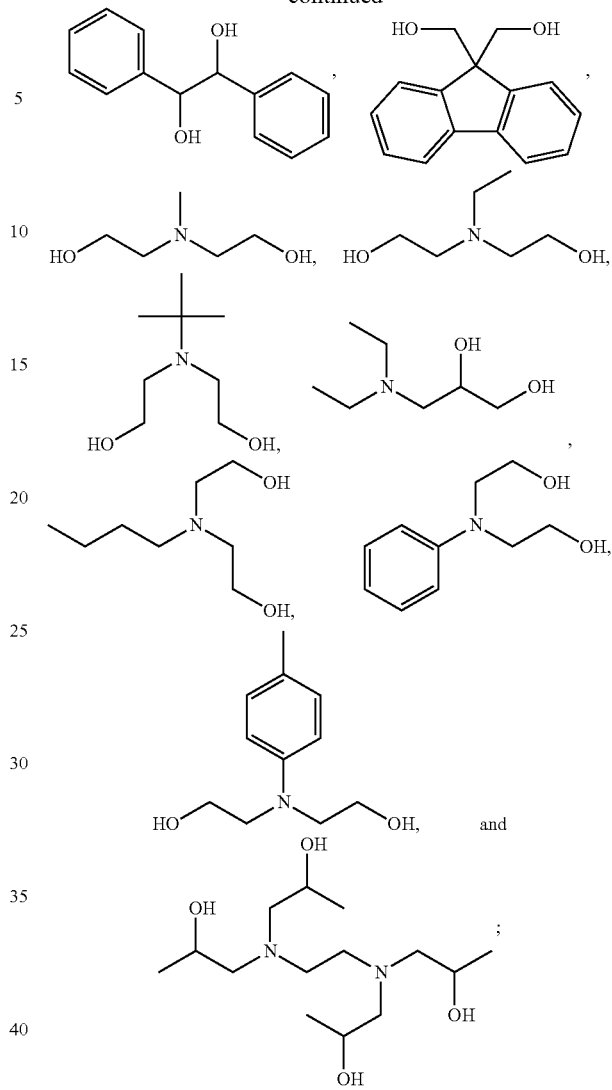
and n of formula IV is an integer of at least one.
17. The composition of claim 16, wherein the molecule of formula IV is a molecule of formula V:
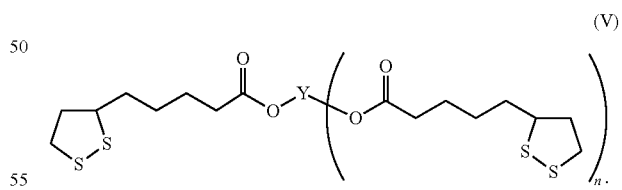
* * * * *